US012747238B2

(12) United States Patent
Coghlan et al.

(10) Patent No.: US 12,747,238 B2
(45) Date of Patent: Sep. 29, 2026

(54) COMPOUNDS FOR TREATMENT OF EXCITOTOXICITY

(71) Applicant: NYRADA PTY LTD, Sydney (AU)

(72) Inventors: Phillip Coghlan, Sydney (AU); Benny Evison, Sydney (AU); Jasneet Parmar, Sydney (AU)

(73) Assignee: NYRADA PTY LTD, Sydney (AU)

( * ) Notice: Subject to any disclaimer, the term of this patent is extended or adjusted under 35 U.S.C. 154(b) by 0 days.

(21) Appl. No.: 19/460,795

(22) Filed: Jan. 27, 2026

(65) Prior Publication Data

US 2026/0152495 A1 Jun. 4, 2026

Related U.S. Application Data

(63) Continuation of application No. PCT/AU2025/051058, filed on Sep. 19, 2025.

(30) Foreign Application Priority Data

Sep. 20, 2024 (AU) ................................ 2024903017

(51) Int. Cl.

| | |
|---|---|
| ***C07D 417/14*** | (2006.01) |
| ***A61K 9/00*** | (2006.01) |
| ***A61K 31/427*** | (2006.01) |
| ***A61K 31/439*** | (2006.01) |
| ***A61K 31/454*** | (2006.01) |
| ***A61K 31/5377*** | (2006.01) |
| ***C07D 417/12*** | (2006.01) |
| ***C07D 471/08*** | (2006.01) |

(52) U.S. Cl.

CPC .......... *C07D 417/14* (2013.01); *A61K 9/0019* (2013.01); *A61K 9/0053* (2013.01); *A61K 31/427* (2013.01); *A61K 31/439* (2013.01); *A61K 31/454* (2013.01); *A61K 31/5377* (2013.01); *C07D 417/12* (2013.01); *C07D 471/08* (2013.01)

(58) Field of Classification Search

CPC ... C07D 417/14; C07D 471/08; C07D 417/12

See application file for complete search history.

(56) References Cited

FOREIGN PATENT DOCUMENTS

| | | |
|---|---|---|
| WO | 2012/037349 | 3/2012 |
| WO | 2012/037351 | 3/2012 |

OTHER PUBLICATIONS

Bon et al. "Pharmacology of TRPC Channels and Its Potential in Cardiovascular and Metabolic Medicine." Annual review of pharmacology and toxicology vol. 62 (2022): 427-446.

Chen et al. "TRPC3/6/7 Knockdown Protects the Brain from Cerebral Ischemia Injury via Astrocyte Apoptosis Inhibition and Effects on NF-KB Translocation." Molecular neurobiology vol. 54, 10 (2017): 7555-7566.

Jeon et al. "Contribution of TRPC Channels in Neuronal Excitotoxicity Associated With Neurodegenerative Disease and Ischemic Stroke." Frontiers in cell and developmental biology vol. 8 (2021): 618663.

Parmar et al. "TRPC Channels Activated by G Protein-Coupled Receptors Drive Ca2+ Dysregulation Leading to Secondary Brain Injury in the Mouse Model." Translational stroke research vol. 15,4 (2024): 844-858.

Belkacemi et al. "TRPC1- and TRPC3-dependent Ca2+ signaling in mouse cortical astrocytes affects injury-evoked astrogliosis in vivo." Glia vol. 65,9 (2017): 1535-1549.

Phelan et al. "Critical role of canonical transient receptor potential channel 7 in initiation of seizures." Proceedings of the National Academy of Sciences of the United States of America vol. 111,31 (2014): 11533-8.

He et al. "Major contribution of the 3/6/7 class of TRPC channels to myocardial ischemia/reperfusion and cellular hypoxia/reoxygenation injuries." Proceedings of the National Academy of Sciences of the United States of America vol. 114,23 (2017): E4582-E4591.

Wu et al. "TRPC channels are necessary mediators of pathologic cardiac hypertrophy." Proceedings of the National Academy of Sciences of the United States of America vol. 107, 15 (2010): 7000-5.

Millay et al. "Calcium influx is sufficient to induce muscular dystrophy through a TRPC-dependent mechanism." Proceedings of the National Academy of Sciences of the United States of America vol. 106,45 (2009): 19023-8.

Hall et al. "TRPC Channels in Proteinuric Kidney Diseases." Cells vol. 9 (2019) 1-44.

Maier et al. "Discovery and pharmacological characterization of a novel potent inhibitor of diacylglycerol-sensitive TRPC cation channels." British journal of pharmacology vol. 172, 14 (2015): 3650-60.

Chen et al. "TRPC6-dependent Ca2+ signaling mediates airway inflammation in response to oxidative stress via ERK pathway." Cell death & disease vol. 11 (2020) 3 170.

Eder & Molkentin. "Trpc channels as effectors of cardiac hypertrophy." Circulation research vol. 108,2 (2011): 265-72.

Nagib et al. "Inhibition of TRPC3 channels by a novel pyrazole compound confers antiseizure effects." Epilepsia vol. 63,4 (2022): 1003-1015.

(Continued)

*Primary Examiner* — Laura L Stockton

(74) *Attorney, Agent, or Firm* — Hovey Williams LLP; Crissa A. Cook

(57) ABSTRACT

The present invention relates to modulators of canonical-type of transient receptor potential (TRPC) channels, compositions thereof, and methods therewith. The present invention also relates to methods of treating TRPC mediated conditions using such modulators.

9 Claims, 7 Drawing Sheets

(56) References Cited

OTHER PUBLICATIONS

International Search Report and Written Opinion in corresponding PCT/AU2025/051058, dated Oct. 20, 2025.
Washburn, et al., "The discovery of potent blockers of the canonical transient receptor channels, TRPC3 and TRPC6, based on an anilino-thiazole pharmacophore", Bioorganic & Medicinal Chemistry Letters, 2013, 23(17), pp. 4979-4984.
Chen, et al., "Transient Receptor Potential Canonical (TRPC) Channels: Then and Now", Cells, 2020, 9(9), article No. 1983, 48 pages.

COMPOUNDS FOR TREATMENT OF EXCITOTOXICITY

RELATED APPLICATION

This application claims priority to and is a continuation of International Patent Application No. PCT/AU2025/051058, filed 19 Sep. 2025, claiming priority to Australian provisional application no 2024903017 filed on 20 Sep. 2024, the contents of which are incorporated herein by reference in their entirety.

FIELD OF THE INVENTION

The present invention relates to novel compounds, pharmaceutical compositions including them, and their use in treating excitotoxicity by blocking TRPC3, TRPC6, TRPC7 ion channels, or any combination thereof, and for the prevention or treatment of conditions or disorders associated with TRPC3, TRPC6, TRPC7 ion channel activity, or any combination thereof.

BACKGROUND OF THE INVENTION

Excitotoxicity particularly following ischemia or haemorrhage contributes significantly to morbidity and mortality associated with many common neurological disorders such as brain injury resulting from stroke and/or traumatic brain injury (TBI), and/or epilepsy and cardiac disorders such as myocardial infarction.

Calcium ion ($Ca^{2+}$) dysregulation resulting from excitotoxicity following brain and cardiac injury can lead to neuronal and glial apoptosis, glial cell (astrocyte and microglia) activation and platelet activation, which can significantly contribute to secondary brain injury. Hence, preventing cell death and preventing activation of inflammation can significantly mitigate the progression of secondary brain injury. Therefore, blocking $Ca^{2+}$ build up in these cells provides an effective approach to protect the brain and the heart from $Ca^{2+}$ ion-mediated injury.

The canonical-type of transient receptor potential (TRPC) channels belong to the TRP superfamily and regulate $Ca^{2+}$ homeostasis. Activation of these channels results in the depolarization of cell membrane and calcium influx. They therefore play a critical role in many cellular processes by changing cytosolic free $Ca^{2+}$ concentrations. The TRPC subfamily has seven mammalian members (TRPC1-7) which participate in store-operated $Ca^{2+}$ entry (SOCE) and/or receptor-operated $Ca^{2+}$ entry (ROCE) in cells. In humans, all isoforms are expressed except TRPC2, which is a pseudogene. TRPC ion channels are coupled to the downstream signalling of Gαq-type G-protein coupled receptors. The functional TRPC channels assemble as tetramers and can be homomeric or heteromeric assemblies of subunits; classified into four subsets: TRPC1, TRPC2, TRPC3/6/7 co-assembly, and TRPC4/5 co-assembly. TRPC3/6/7 are notable in being directly activated by phospholipase C-generated diacylglycerols (DAGs) (Bon, Wright et al. 2022).

TRPC3, TRPC6 and TRPC7 subtypes are widely expressed in the brain and the heart and are implicated in the pathology of various neurological indications involving $Ca^{2+}$ dysregulation including ischemia (Chen, Lu et al. 2017, Jeon, Bu et al. 2020, Parmar, von Jonquieres et al. 2023), hemorrhage, brain trauma (Belkacemi, Niermann et al. 2017), epilepsy, seizure like activity and other convulsive activity (Phelan, Shwe et al. 2014, Nagib, Zhang et al. 2022), Alzheimer's disease (Jeon, Bu et al. 2020), and myocardial ischemic reperfusion injury (He, Li., et al 2017).

Through utilization of transgenic mouse models, TRPC3, TRPC6, TRPC7 ion channels have been shown to play a significant role in the secondary brain injury following ischemia in the brain (Chen, Lu et al. 2017, Parmar, von Jonquieres et al. 2023), epilepsy (Phelan, Shwe et al. 2014, Nagib, Zhang et al. 2022) and ischemic-reperfusion injury in the heart (He, Li et al. 2017).

Specific and dual inhibitors of TRPC3 and TRPC6 ion channels have been previously described (Washburn, Holt et al. 2013). But there is limited evidence of these blockers demonstrating brain penetration which is needed to treat neurological and cardiological diseases and disorders associated with over activation of one or more of TRPC3, TRPC6 and TRPC7 ion channels.

There is a need for improved treatments of ischemia and reperfusion injury, including stroke, traumatic brain injury, myocardial infarction and the treatment of seizure, hemorrhage, brain trauma, epilepsy and Alzheimer's disease.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present inventors have surprisingly identified that compounds of Formula I or Formula II can function as effective blockers (or antagonist or inhibitor) of TRPC3, TRPC6 and TRPC7 ion channels.

In a first aspect there is provided a compound of Formula I, or a pharmaceutically acceptable salt, solvate or stereoisomer thereof:

Formula I

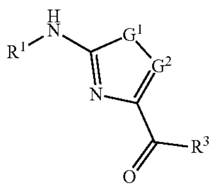

wherein:

$G^1$ is O or S;

$G^2$ is $CR^2$ or N;

$R^1$ is a bicyclic system (A)

(A)

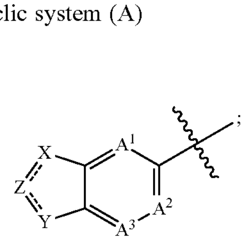

wherein: the dashed line ( ---- ) represents either a double bond (=) or a single bond (–); and wherein when X and Z are connected by a double bond, Z and Y are connected by a single bond, and when X and Z are connected by a single bond, Z and Y are connected by a double bond;

$A^1$, $A^2$ and $A^3$ are independently selected from $CR^4$ or N;

each $R^4$ is independently selected from H, D, halo, $C_1$-$C_4$alkyl, hydroxy, amino, $C_1$-$C_4$alkyl, $C_1$-$C_4$alkoxy, $C_1$-$C_4$fluoroalkyl, phenyl, cyano, $C_1$-$C_4$thioalkyl, and $C_1$-$C_4$alkylamino;

X is selected from CH, CD, $CH_2$, CHD, $CD_2$, O, S, $CR^5$, and $CR^5R^6$;

Y is selected from CH, CD, $CH_2$, CHD, $CD_2$, O, S, N, $CR^5$, $CR^5R^6$, and $NR^7$;

$R^5$, $R^6$ and $R^7$ when present, are independently selected from H, D, halo, $C_1$-$C_6$alkyl, hydroxy, amino, $C_1$-$C_6$alkyl, $C_1$-$C_6$alkoxy, $C_1$-$C_6$fluoroalkyl, phenyl, cyano, $C_1$-$C_6$thioalkyl, and $C_1$-$C_6$alkylamino;

Z is independently selected from CH and CD;

$R^2$ is H, D, halo, hydroxy, amino, cyano, or $C_1$-$C_4$alkyl;

$R^3$ is:

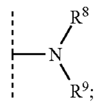

$R^8$ and $R^9$ form an optionally substituted ring; the ring formed by $R^8$ and $R^9$ and the N atom between them comprises 3-9 ring atoms.

In a further aspect, there is provided a compound of Formula II or a pharmaceutically acceptable salt thereof:

Formula II

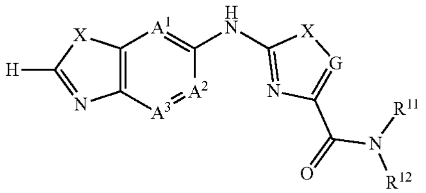

$A^1$, $A^2$ and $A^3$ are selected from N, CH and CF;

X is selected from O and S;

G is selected from N and $CR^{10}$;

$R^{10}$ is H, D, halo, $C_1$-$C_4$alkyl, hydroxy, amino, $C_1$-$C_4$alkyl, $C_1$-$C_4$alkoxy, $C_1$-$C_4$fluoroalkyl, phenyl, cyano, $C_1$-$C_4$thioalkyl, or $C_1$-$C_4$alkylamino;

$R^{11}$ and $R^{12}$ together with the N atom between them form a ring; wherein the ring comprises 3-9 ring atoms.

In another aspect, the invention provides for pharmaceutical compositions comprising a compound of Formula I or Formula II, or a pharmaceutically acceptable salt thereof, and a pharmaceutically acceptable excipient.

In another aspect, the invention provides a method of inhibiting TRPC3, TRPC6, TRPC7 ion channel activity, or a combination thereof, comprising administering to a cell, tissue or an individual in need thereof, an effective amount of a compound of Formula I or Formula II, or a pharmaceutically acceptable salt thereof.

In another aspect, the invention provides a method of preventing or treating a condition or disease associated with TRPC3, TRPC6, or TRPC7 ion channel activity, or a combination thereof, in an individual in need thereof, comprising administering a compound of Formula I or Formula II, or a pharmaceutically acceptable salt thereof.

In some embodiments, the disease or condition is mediated by all three of TRPC3, TRPC6, and TRPC7 ion channels, and more specifically, inhibition or blocking of those channels. The diseases or conditions include neurological conditions or diseases, cardiac failure, cardiac hypertrophy, muscular dystrophy, kidney diseases, and pulmonary diseases, wherein inhibition or blocking of those channels is beneficial. In a further aspect the invention provides a method of preventing or treating a neurological condition or disease in an individual in need thereof, comprising administering a compound of Formula I or Formula II, or a pharmaceutically acceptable salt thereof. Preferably the neurological condition or disease is selected from one or more of ischemia, haemorrhage, concussion, brain injury/traumatic brain injury (TBI), epilepsy, and Alzheimer's disease.

In another aspect, the present invention also provides a method of treating, or reducing the severity of a symptom of a disease or condition in an individual, wherein the disease or condition is associated with TRPC3, TRPC6, TRPC7 ion channel activity, or a combination thereof, comprising administering a therapeutically effective amount of a compound of Formula I or Formula II, or pharmaceutically acceptable salt thereof, thereby treating, or reducing the severity of the symptom of the disease or condition in the individual.

In another aspect, the present invention provides a method of treating, or reducing the severity of a symptom of cardiac injury in an individual in need thereof, comprising administering a therapeutically effective amount of a compound of Formula I or Formula II or pharmaceutically acceptable salt thereof.

In another aspect, the invention provides the use of a compound of Formula I or Formula II, or a pharmaceutically acceptable salt thereof in the manufacture of a medicament for:

- preventing or treating a condition or disease associated with TRPC3, TRPC6, TRPC7 ion channel activity, or a combination thereof, in an individual in need thereof;
- preventing or treating a or disease associated with all three of TRPC3, TRPC6, and TRPC7 ion channel activity;
- preventing or treating a neurological disease, preferably wherein the neurological condition or disease is selected from one or more of ischemia, hemorrhage, concussion, brain injury/traumatic brain injury (TBI), epilepsy, and Alzheimer's disease;
- preventing or treating cardiac injury.

In embodiments the diseases or conditions include neurological conditions or diseases, cardiac failure, cardiac hypertrophy, muscular dystrophy, kidney diseases, and pulmonary diseases, wherein inhibition or blocking of those channels is beneficial.

In another aspect, the invention provides for the use of a compound of Formula I or Formula II, or a pharmaceutically acceptable salt thereof,

- as a medicament;
- for treating, or reducing the severity of a symptom of a disease or condition in an individual, wherein the disease or condition is associated with TRPC3, TRPC6, TRPC7 ion channel activity, or a combination thereof;
- for treating, or reducing the severity of a symptom of a disease or condition in an individual, wherein the disease or condition is associated with one or more of TRPC3, TRPC6, and TRPC7 ion channel activity;
- for treating a neurological condition, preferably one or more of ischemia, hemorrhage, concussion, brain injury/traumatic brain injury (TBI), epilepsy, and Alzheimer's disease; or
- for treating cardiac injury.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
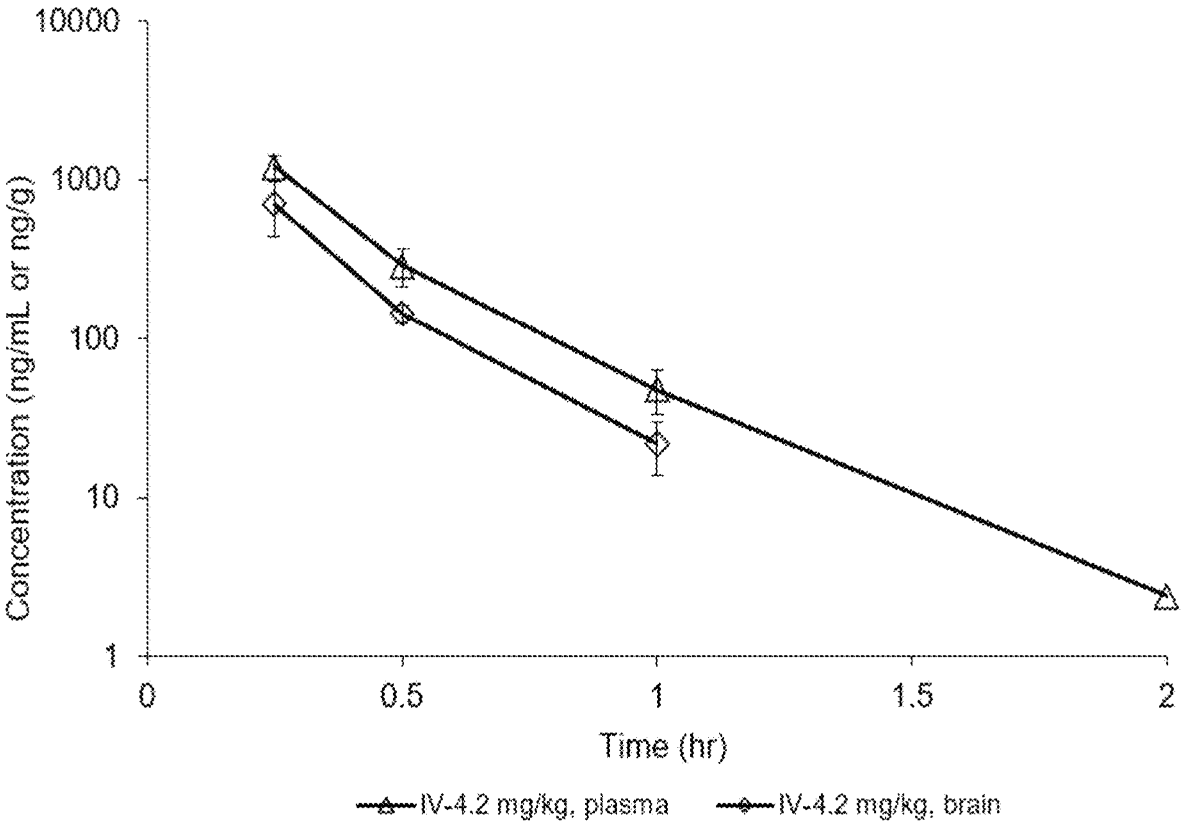
FIG. 1: Graph showing the mean plasma and brain concentrations of Compound 1 following single intravenous (i.v.) injection in mice.

It will be understood that the invention disclosed and defined in this specification extends to all alternative combinations of two or more of the individual features mentioned or evident from the text or drawings. All these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

Definitions

As used herein, except where the context requires otherwise, the term "comprise" and variations of the term, such as "comprising", "comprises" and "comprised", are not intended to exclude further additives, components, integers, or steps.

It must be noted that as used herein and in the appended claims, the singular forms "a", "an" and "the" include plural reference unless the context clearly dictates otherwise.

Thus, for example, a reference to "a salt" may include a plurality of salts and a reference to "at least one heteroatom" may include one or more heteroatoms, and so forth.

The term "(s)" following a noun contemplates the singular or plural form, or both. For purposes of interpreting this specification, terms used in the singular will also include the plural and vice versa.

The term "about" is intended to convey that the value in question is not to be taken as being limited to exactly that value and is intended to include minor variations on the value sufficient for the working of the invention. It is within the skill set of the skilled person to determine the degree of variance from the value that will still achieve the desired result.

When any two substituent groups or any two instances of the same substituent group are "independently selected" from a list of alternatives, the groups may be the same or different. For example, if $R^a$ and $R^b$ are independently selected from alkyl, fluoro, amino, and hydroxyalkyl, then a molecule with two $R^a$ groups and two $R^b$ groups could have all groups be an alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different). In some embodiments, multiple instances of variables that may be selected from a list of alternatives are independently selected.

A "substituent" as used herein, refers to a molecular moiety that is covalently bonded to an atom within a molecule of interest. For example, a "ring substituent" may be a moiety such as a halogen, alkyl group, or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, ie, a compound that can be isolated, characterized and tested for biological activity.

The terms "optionally substituted" or "may be substituted" and the like, as used throughout the specification, denotes that the group may or may not be further substituted or fused (so as to form a polycyclic system), with one or more non-hydrogen substituent groups. Suitable chemically viable substituents for a particular functional group will be apparent to those skilled in the art.

Examples of substituents include but are not limited to $C_1$-$C_6$alkyl, $C_1$-$C_6$haloalkyl, $C_1$-$C_6$haloalkoxy, $C_1$-$C_6$hydroxyalkyl, $C_3$-$C_7$heterocyclyl, $C_3$-$C_7$cycloalkyl, $C_1$-$C_6$alkoxy, $C_1$-$C_6$alkylsulfanyl, $C_1$-$C_6$alkylsulfenyl, $C_1$-$C_6$alkylsulfonyl, $C_1$-$C_6$alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, halo, ureido, $C_1$-$C_6$perfluoroalkyl. Preferably the substituents include amino, halo, $C_1$-$C_6$alkyl, amido, hydroxyl.

As used herein the term "alkyl" refers to a straight or branched chain hydrocarbon radical having from one to twelve carbon atoms, or any range between, i.e. it contains 1, 2, 3, 4, 5, 6, 7, 8, 9, 10, 11 or 12 carbon atoms. The alkyl group is optionally substituted with substituents.

Examples of "alkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_2$alkyl", "$C_1$-$C_4$alkyl" and "$C_1$-$C_6$alkyl" refer to an alkyl group, as defined herein, containing at least 1, and at most 2, 4 or 6 carbon atoms respectively, or any range in between (eg alkyl groups containing 2-5 carbon atoms are also within the range of $C_1$-$C_6$).

The term "cycloalkyl" is intended to include mono-, bi- or tricyclic alkyl groups. In some embodiments, cycloalkyl groups have from 3 to 12, from 3 to 10, from 3 to 8, from 3 to 6, from 3 to 5 carbon atoms in the ring(s). In some embodiments, cycloalkyl groups have 5 or 6 ring carbon atoms. Examples of monocyclic cycloalkyl groups include, but are not limited to, cyclopropyl, cyclobutyl, cyclopentyl, cyclohexyl, cycloheptyl, and cyclooctyl.

In some embodiments, the cycloalkyl group has from 2 to 9, from 3 to 8, from 3 to 7, from 3 to 6, from 4 to 6, from 3 to 5, or from 4 to 5 ring carbon atoms. As used herein, the terms "$C_3$-$C_6$cycloalkyl", "$C_3$-$C_4$cycloalkyl" and "$C_3$-$C_7$cycloalkyl" refer to an alkyl group, as defined herein, containing at least 3, and at most 6, 4 or 7 carbon atoms respectively, or any range in between (eg alkyl groups containing 4-5 carbon atoms are also within the range of $C_3$-$C_6$).

The term "heterocycle" refers to a cycloalkyl group having from 3 to 10 ring atoms (unless otherwise specified), of which 1, 2, 3 or 4 are ring heteroatoms each heteroatom being independently selected from O, S and N. The term "heterocyclyl" refers to a moiety obtained by removing a hydrogen atom from a ring atom of a heterocyclic compound which moiety. As used herein the term "$C_3$-$C_6$heterocyclyl" refers to a heterocycle having 3 to 6 ring members with at least one ring member being a heteroatom.

The term "carbonyl" refers to the group C═O.

The term "amino" or "amine" refers to the group $—NH_2$.

As used herein "D" refers to deuterium.

The term "$C_1$-$C_5$alkylamino" refers to an amino group having a hydrogen replaced with a $C_1$-$C_5$alkyl group, wherein the $C_1$-$C_5$alkyl group is as herein defined.

As used herein, the term "halogen" refers to fluorine (F), chlorine (Cl), bromine (Br), or iodine (I) and the term "halo" refers to the halogen radicals fluoro (—F), chloro (Cl), bromo (—Br), and iodo (—I). Preferably, 'halo' is fluoro or chloro or bromo.

As used herein, the term "alkoxy" refers to an alkyl group as defined herein covalently bound via an O linkage. The alkoxy group is optionally substituted with substituents. Examples of "alkoxy" as used herein include, but are not limited to methoxy, ethoxy, propoxy, isoproxy, butoxy, isobutoxy, tert-butoxy and pentoxy.

As used herein, the terms "$C_1$-$C_2$alkoxy", "$C_1$-$C_4$alkoxy" and "$C_1$-$C_6$alkoxy" refer to an alkoxy group, as defined herein, containing at least 1, and at most 2, 4 or 6 carbon atoms respectively, or any range in between (eg alkoxy groups containing 2-5 carbon atoms are also within the range of $C_1$-$C_6$).

As used herein, the term "haloalkyl" refers to an alkyl group as defined herein substituted with at least one halogen.

As used herein, the terms "$C_1$-$C_2$haloalkyl", "$C_1$-$C_4$haloalkyl" and "$C_1$-$C_6$haloalkyl" refer to an haloalkyl group, as defined herein, containing at least 1, and at most 2, 4 or 6 carbon atoms respectively, or any range in between (e.g. haloalkyl groups containing 2-5 carbon atoms are also within the range of $C_1$-$C_6$).

For example a $C_1$ haloalkyl group could be, but is not limited to, chloromethyl, or dichloromethyl, or trichloromethyl.

As used herein the term "fluoroalkyl" refers to a straight or branched chain hydrocarbon radical having from one to twelve carbon atoms or any range between i.e. it contains 1, 2, 3, 4, 5, 6, 7, 8, 9, 10, 11 or 12 carbon atoms and wherein at least one of the hydrogen atoms is substituted by a fluorine, All of the hydrogen atoms may be substituted by a fluorine. The fluoroalkyl group is optionally substituted with substituents.

Examples of "fluoroalkyl" as used herein include, but are not limited to, fluoromethyl, difluoromethyl, trifluoromethyl, fluoroethyl, difluoroethyl, trifluoroethyl, perfluoroethyl and the like.

As used herein the terms "$C_1$-$C_2$fluoro alkyl", "$C_1$-$C_4$fluoroalkyl" and "$C_1$-$C_5$fluoroalkyl" refer to an fluoroalkyl group, as defined above, containing at least 1, and at most 2, 4 or 6 carbon atoms respectively, or any range in between (e.g. fluoroalkyl groups containing 2-5 carbon atoms are also within the range of $C_1$-$C_6$).

The term "$C_1$-$C_5$ thioalkyl" refers to a group in the form of $C_1$-$C_5$ alkyl-SH, wherein the $C_1$-$C_5$ alkyl group is as herein defined.

The term "cyano" and "nitrile" refer to the group-CN.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. The term "stereoisomers" refers to compounds which have identical chemical constitution, but differ with regard to the arrangement of the atoms or groups in space. As used herein, the term "stereoisomer" includes but is not limited to diastereomers, enantiomers and atropisomers, as well as mixtures thereof such as racemic mixtures.

As used herein, the term "a compound of" a particular formula or "the compound of" a particular formula refers to one or more compounds according to that formula.

As used herein, "pharmaceutically acceptable" refers to those compounds, materials, compositions, and dosage forms which are, within the scope of sound medical judgment, suitable for use in contact with the tissues of human beings without excessive toxicity, irritation, or other problem or complication, commensurate with a reasonable benefit/risk ratio.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

As used herein, "pharmaceutically acceptable excipient" means a pharmaceutically acceptable material which is included in the composition for a purpose other than pharmaceutical efficacy (this is not intended to exclude materials which may have some biological effect).

As used herein, "preventing" or "prevention" is intended to refer to at least the reduction of likelihood of the risk of (or susceptibility to) acquiring a disease or condition (i.e., causing at least one of the clinical symptoms of the disease not to develop in an individual that may be exposed to or predisposed to the disease but does not yet experience or display symptoms of the disease). Biological and physiological parameters for identifying such patients are also well known by physicians.

The skilled artisan will appreciate that "prevention" is not an absolute term. In particularly preferred embodiments, the methods of the present invention can be to prevent or reduce the severity, or inhibit or minimize progression, of a symptom of a disease or condition as described herein. As such, the methods of the present invention have utility as treatments as well as prophylaxes.

The terms "treatment" or "treating" of a subject includes delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the individual; slowing in the rate of degeneration or decline; making the final point of degeneration less debilitating. Treatment may not necessarily result in the complete clearance of a disease or disorder but may reduce or minimize complications and side effects of infection and the progression of a disease or disorder. The success or otherwise of treatment may be monitored by, amongst other things, physical examination of the individual, behavioural, cognitive and motor function test of the individual, CT scan, MRI, or blood biomarkers.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Compounds of the Invention

The inventors have surprisingly found that compounds of Formula I or Formula II, and pharmaceutically acceptable salts thereof are able to block TRPC3, TRPC6 and TRPC7 ion channels and are promising therapeutic targets for treating diseases associated with TRPC3, TRPC6 and TRPC7 ion channel activity.

Compounds of Formula I, or a pharmaceutically acceptable salt, solvate or stereoisomer thereof are described herein:

Formula I

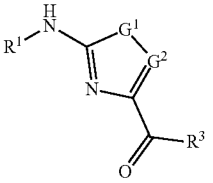

wherein:

$G^1$ is O or S;

$G^2$ is $CR^2$ or N;

$R^1$ is a bicyclic system (A)

(A)

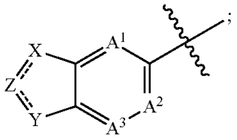

wherein: the dashed line ( ---- ) represents either a double bond (=) or a single bond (–); and $A^1$, $A^2$ and $A^3$ are independently selected from $CR^4$ and N;

each $R^4$ is independently selected from H, D, halo, $C_1$-$C_4$alkyl, hydroxy, amino, $C_1$-$C_4$alkyl, $C_1$-$C_4$alkoxy, $C_1$-$C_4$fluoroalkyl, phenyl, cyano, $C_1$-$C_4$thioalkyl, and $C_1$-$C_4$alkylamino;

X is selected from CH, CD, $CH_2$, CHD, $CD_2$, O, S, $CR^5$ and $CR^5R^6$; Y is selected from CH, CD, $CH_2$, CHD, $CD_2$, O, S, N, $CR^5$, $CR^5R^6$, and $NR^7$;

$R^5$, $R^6$ and $R^7$ when present, are independently selected from H, D, halo, $C_1$-$C_6$alkyl, hydroxy, amino, $C_1$-$C_6$alkyl, $C_1$-$C_6$alkoxy, $C_1$-$C_6$fluoroalkyl, phenyl, cyano, $C_1$-$C_6$thioalkyl, and $C_1$-$C_6$alkylamino;

Z is independently selected from CH and CD;

$R^2$ is selected from H, D, halo, hydroxy, amino, cyano, or $C_1$-$C_4$alkyl;

$R^3$ is:

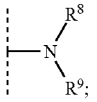

where $R^8$ and $R^9$ form an optionally substituted ring; the ring formed by $R^8$ and $R^9$ and the N atom between them comprises 3-9 ring atoms.

In embodiments when X and Z are connected by a double bond, Z and Y are connected by a single bond, and when X and Z are connected by a single bond, Z and Y are connected by a double bond.

In embodiments X is O or S; and Y is N.

In embodiments $A^1$ and $A^2$ are $CR^4$; and $A^3$ is N or $CR^4$. In embodiments $A^1$ and $A^2$ are CH and $A^3$ is N or $CR^4$, preferably CH or CF.

In embodiments the ring formed by $R^8$ and $R^9$ together with the N atom between them can be mono-cyclic saturated straight-chain alkyl ring, such as

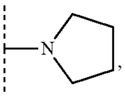,
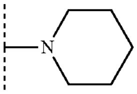,
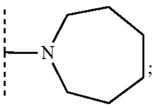;

or mono-cyclic branched-chain alkyl ring, such as

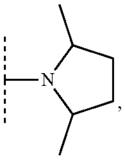,
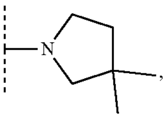,
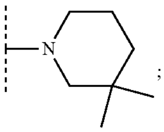;

or bicyclic such as

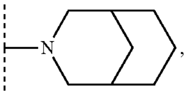,
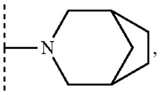,
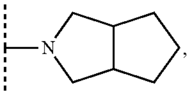,
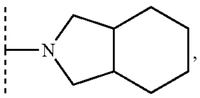,
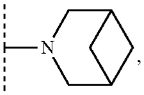,
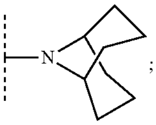;

or can be variously unsaturated cyclic, such as

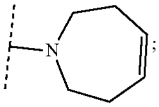;

or can be variously hetero substituted, such as

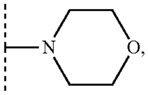,
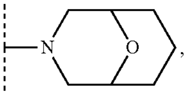,
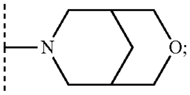;

or can be variously substituted, such as

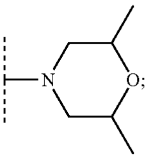;

or can be halo substituted, such as

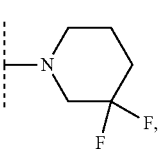,
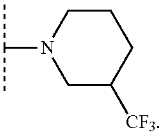.

In embodiments the ring formed by $R^8$ and $R^9$ together with the N atom between them is selected from

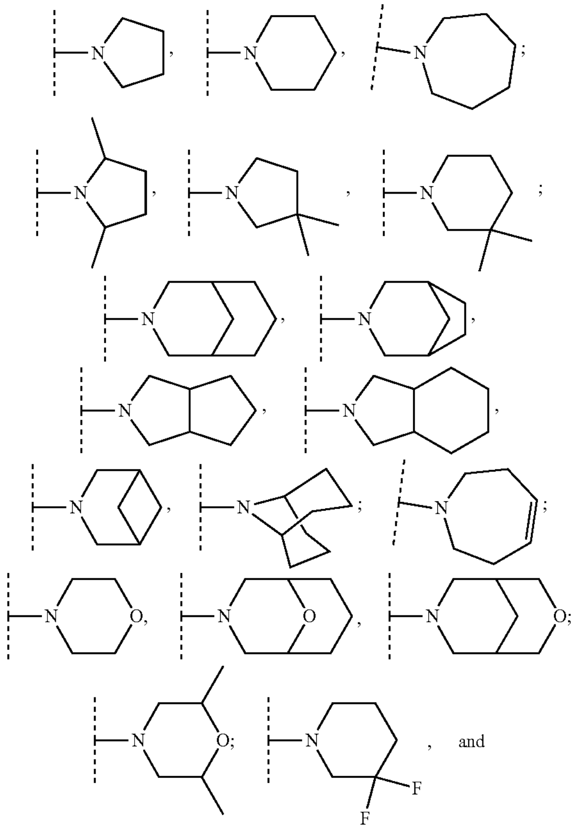

and

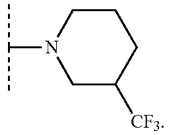

In embodiments $R^1$ is:

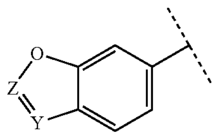

or

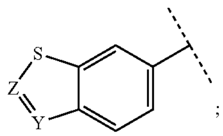

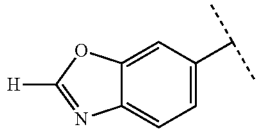

or

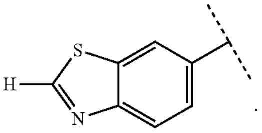

preferably

In embodiments, $R^3$ is 1-piperidine substituted with 1-4 substituents independently selected from D, halo, $C_1$-$C_6$alkyl, $C_1$-$C_6$alkoxy, $C_1$-$C_6$fluoroalkyl, phenyl, cyano, $C_1$-$C_6$thioalkyl, and $C_1$-$C_6$alkylamino. In some particular embodiments, the piperidine ring is substituted with 2-3 substituents selected from these groups.

In embodiments, $R^3$ is 1-piperidine substituted with 1-2 $C_1$-$C_6$alkyl groups. In some such embodiments, $C_1$-$C_6$alkyl is methyl (in some particular embodiments, two methyl groups on the same or different ring carbon atoms, and in more particular embodiments 2,2-; 2,3-; 2,5-; 3,3-; 3,5-; or 2,6-dimethyl).

In embodiments, $R^3$ is 3,5-dimethylpiperidine, preferably

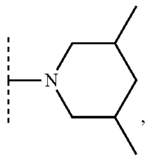

more preferably where the relative stereochemistry of the methyl groups is 'syn' as in

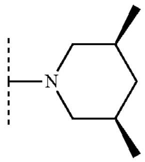

and

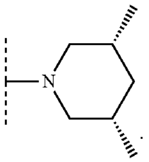

In embodiments, $R^3$ is 2,3-dimethylpiperidine, preferably

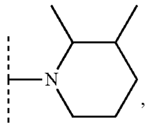

more preferably where the relative stereochemistry of the methyl groups is 'syn' as in

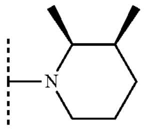

and

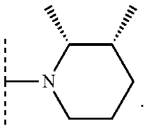

In a further aspect, there is provided a compound of Formula II or a pharmaceutically acceptable salt thereof:

Formula II

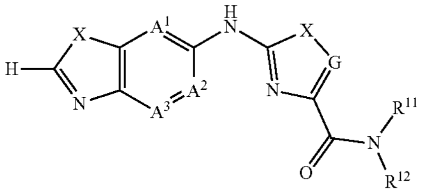

$A^1$, $A^2$ and $A^3$ are selected from N, CH and CF;

X is selected from O and S;

G is selected from N and $CR^{10}$;

$R^{10}$ is H, D, halo, $C_1$-$C_4$alkyl, hydroxy, amino, $C_1$-$C_4$alkyl, $C_1$-$C_4$alkoxy, $C_1$-$C_4$fluoroalkyl, phenyl, cyano, $C_1$-$C_4$thioalkyl, and $C_1$-$C_4$alkylamino;

where $R^{11}$ and $R^{12}$ form a ring; the ring formed by $R^{11}$ and $R^{12}$ comprises 3-9 ring atoms, can be mono- or bi-cyclic, saturated or unsaturated, straight- or branched-chain, or halo- or hetero-substituted alkyl.

In embodiments $A^1$ and $A^2$ are CH and $A^3$ is selected from N, CH and CF.

In one embodiment, compounds of Formula I or Formula II, or pharmaceutically acceptable salts thereof, may be selected from the group consisting of the compounds in Table 1:

TABLE 1

| Compound Number | Structure | Chemical Name |
|---|---|---|
| 1 | 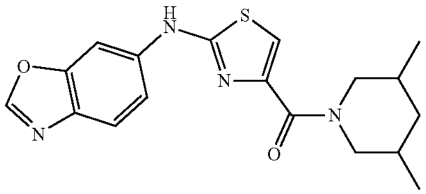 [SMILES: CC1CC(C)CN(C(=O)c2csc(Nc3ccc4ncoc4c3)n2)C1] | N-{4-[3,5-dimethylpiperidine-1-carbonyl]-1,3-thiazol-2-yl}-1,3-benzoxazol-6-amine |
| 2 | 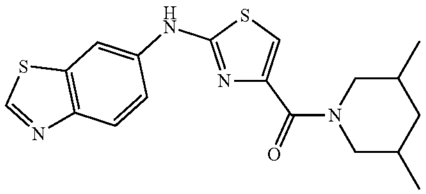 [SMILES: CC1CC(C)CN(C(=O)c2csc(Nc3ccc4ncsc4c3)n2)C1] | N-{4-[3,5-dimethylpiperidine-1-carbonyl]-1,3-thiazol-2-yl}-1,3-benzothiazol-6-amine |
| 3 | 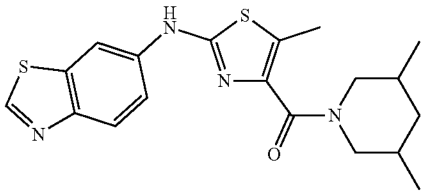 [SMILES: Cc1sc(Nc2ccc3ncsc3c2)nc1C(=O)N1CC(C)CC(C)C1] | N-{4-[3,5-dimethylpiperidine-1-carbonyl]-5-methyl-1,3-thiazol-2-yl}-1,3-benzothiazol-6-amine |
| 4 | 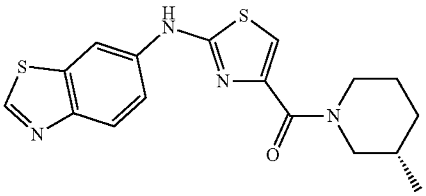 [SMILES: C[C@H]1CCCN(C(=O)c2csc(Nc3ccc4ncsc4c3)n2)C1] | N-{4-[(3S)-3-methylpiperidine-1-carbonyl]-1,3-thiazol-2-yl}-1,3-benzothiazol-6-amine |
| 5 | 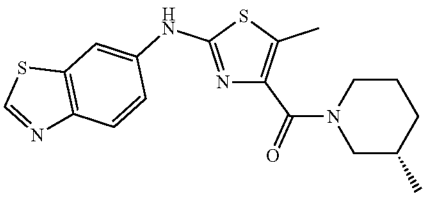 [SMILES: Cc1sc(Nc2ccc3ncsc3c2)nc1C(=O)N1CCC[C@H](C)C1] | N-{5-methyl-4-[(3S)-3-methylpiperidine-1-carbonyl]-1,3-thiazol-2-yl}-1,3-benzothiazol-6-amine |
| 6 | 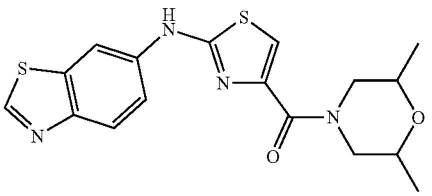 [SMILES: CC1CN(C(=O)c2csc(Nc3ccc4ncsc4c3)n2)CC(C)O1] | N-{4-[2,6-dimethylmorpholine-4-carbonyl]-1,3-thiazol-2-yl}-1,3-benzothiazol-6-amine |
| 7 | 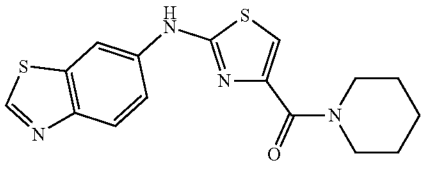 [SMILES: O=C(c1csc(Nc2ccc3ncsc3c2)n1)N1CCCCC1] | N-[4-(piperidine-1-carbonyl)-1,3-thiazol-2-yl]-1,3-benzothiazol-6-amine |

TABLE 1-continued

| Compound Number | Structure | Chemical Name |
|---|---|---|
| 8 | 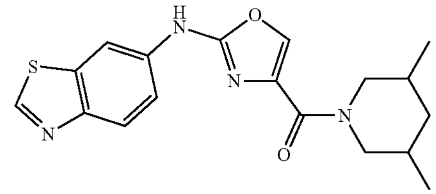 [SMILES: CC1CC(C)CN(C(=O)c2coc(Nc3ccc4ncsc4c3)n2)C1] | N-{4-[3,5-dimethylpiperidine-1-carbonyl]-1,3-oxazol-2-yl}-1,3-benzothiazol-6-amine |
| 9 | 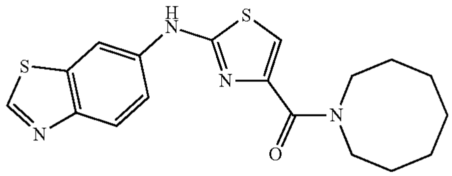 [SMILES: O=C(c1csc(Nc2ccc3ncsc3c2)n1)N1CCCCCCC1] | N-[4-(azocane-1-carbonyl)-1,3-thiazol-2-yl]-1,3-benzothiazol-6-amine |
| 10 | 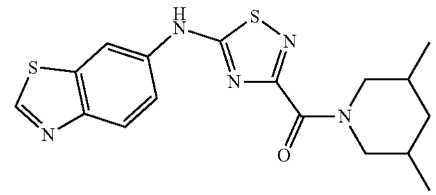 [SMILES: CC1CC(C)CN(C(=O)c2nsc(Nc3ccc4ncsc4c3)n2)C1] | N-{3-[3,5-dimethylpiperidine-1-carbonyl]-1,2,4-thiadiazol-5-yl}-1,3-benzothiazol-6-amine |
| 11 | 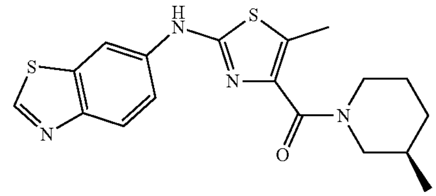 [SMILES: Cc1sc(Nc2ccc3ncsc3c2)nc1C(=O)N1CCC[C@@H](C)C1] | N-{5-methyl-4-[(3R)-3-methylpiperidine-1-carbonyl]-1,3-thiazol-2-yl}-1,3-benzothiazol-6-amine |
| 12 | 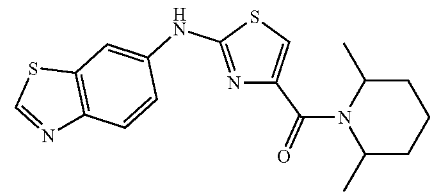 [SMILES: CC1CCCC(C)N1C(=O)c1csc(Nc2ccc3ncsc3c2)n1] | N-{4-[2,6-dimethylpiperidine-1-carbonyl]-1,3-thiazol-2-yl}-1,3-benzothiazol-6-amine |
| 13 | 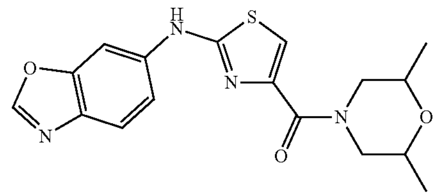 [SMILES: CC1CN(C(=O)c2csc(Nc3ccc4ncoc4c3)n2)CC(C)O1] | N-{4-[2,6-dimethylmorpholine-4-carbonyl]-1,3-thiazol-2-yl}-1,3-benzoxazol-6-amine |
| 14 | 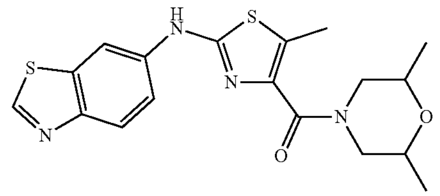 [SMILES: Cc1sc(Nc2ccc3ncsc3c2)nc1C(=O)N1CC(C)OC(C)C1] | N-{4-[2,6-dimethylmorpholine-4-carbonyl]-5-methyl-1,3-thiazol-2-yl}-1,3-benzothiazol-6-amine |

TABLE 1-continued

| Compound Number | Structure | Chemical Name |
|---|---|---|
| 15 | 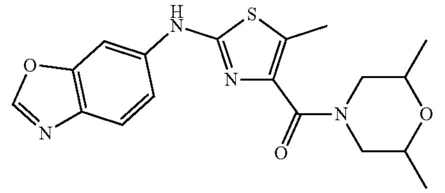 [SMILES: Cc1sc(Nc2ccc3ncoc3c2)nc1C(=O)N1CC(C)OC(C)C1] | N-{4-[2,6-dimethylmorpholine-4-carbonyl]-5-methyl-1,3-thiazol-2-yl}-1,3-benzoxazol-6-amine |
| 16 | 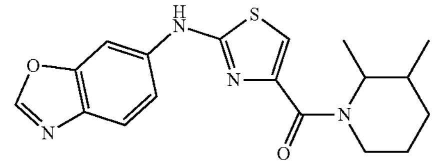 [SMILES: CC1CCCN(C(=O)c2csc(Nc3ccc4ncoc4c3)n2)C1C] | N-{4-[2,3-dimethylpiperidine-1-carbonyl]-1,3-thiazol-2-yl}-1,3-benzoxazol-6-amine |
| 17 | 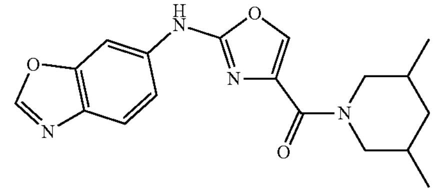 [SMILES: CC1CC(C)CN(C(=O)c2coc(Nc3ccc4ncoc4c3)n2)C1] | N-{4-[3,5-dimethylpiperidine-1-carbonyl]-1,3-oxazol-2-yl}-1,3-benzoxazol-6-amine |
| 18 | 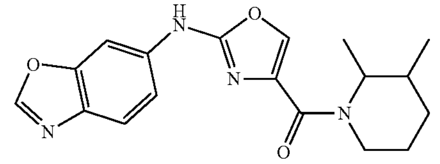 [SMILES: CC1CCCN(C(=O)c2coc(Nc3ccc4ncoc4c3)n2)C1C] | N-{4-[2,3-dimethylpiperidine-1-carbonyl]-1,3-oxazol-2-yl}-1,3-benzoxazol-6-amine |
| 19 | 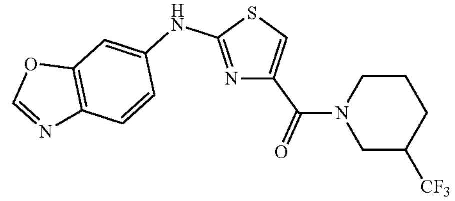 [SMILES: O=C(c1csc(Nc2ccc3ncoc3c2)n1)N1CCCC(C(F)(F)F)C1] | N-{4-[3-(trifluoromethyl)piperidine-1-carbonyl]-1,3-thiazol-2-yl}-1,3-benzoxazol-6-amine |
| 20 | 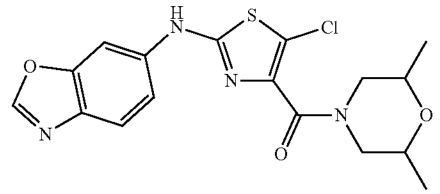 [SMILES: CC1CN(C(=O)c2nc(Nc3ccc4ncoc4c3)sc2Cl)CC(C)O1] | N-{5-chloro-4-[2,6-dimethylmorpholine-4-carbonyl]-1,3-thiazol-2-yl}-1,3-benzoxazol-6-amine |
| 21 | 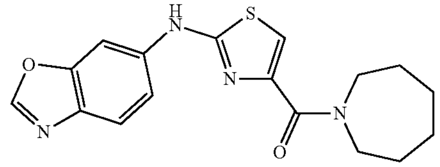 [SMILES: O=C(c1csc(Nc2ccc3ncoc3c2)n1)N1CCCCCC1] | N-[4-(azepane-1-carbonyl)-1,3-thiazol-2-yl]-1,3-benzoxazol-6-amine |
| 22 | 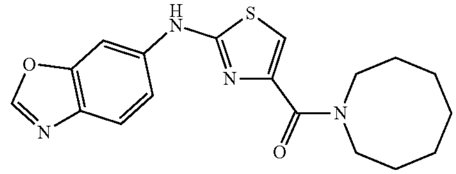 [SMILES: O=C(c1csc(Nc2ccc3ncoc3c2)n1)N1CCCCCCC1] | N-[4-(azocane-1-carbonyl)-1,3-thiazol-2-yl]-1,3-benzoxazol-6-amine |

TABLE 1-continued

| Compound Number | Structure | Chemical Name |
|---|---|---|
| 23 | 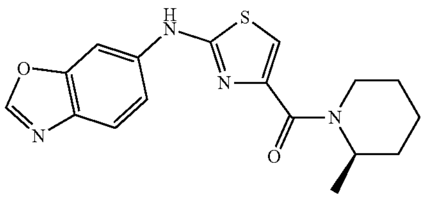 [SMILES: C[C@@H]1CCCCN1C(=O)c1csc(Nc2ccc3ncoc3c2)n1] | N-{4-[(2R)-2-methylpiperidine-1-carbonyl]-1,3-thiazol-2-yl}-1,3-benzoxazol-6-amine |
| 24 | 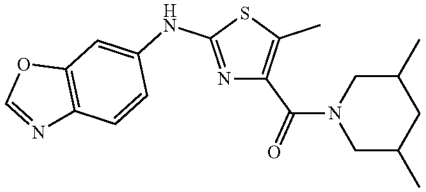 [SMILES: Cc1sc(Nc2ccc3ncoc3c2)nc1C(=O)N1CC(C)CC(C)C1] | N-{4-[3,5-dimethylpiperidine-1-carbonyl]-5-methyl-1,3-thiazol-2-yl}-1,3-benzoxazol-6-amine |
| 25 | 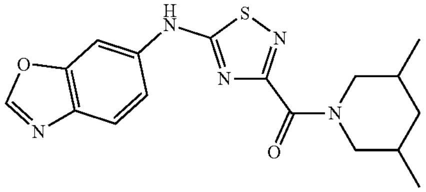 [SMILES: CC1CC(C)CN(C(=O)c2nsc(Nc3ccc4ncoc4c3)n2)C1] | N-{3-[3,5-dimethylpiperidine-1-carbonyl]-1,2,4-thiadiazol-5-yl}-1,3-benzoxazol-6-amine |
| 26 | 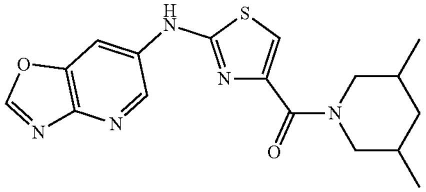 [SMILES: CC1CC(C)CN(C(=O)c2csc(Nc3cnc4ncoc4c3)n2)C1] | 4-[3,5-dimethylpiperidine-1-carbonyl]-N-{[1,3]oxazolo[4,5-b]pyridine-6-yl}-1,3-thiazol-2-amine |
| 27 | 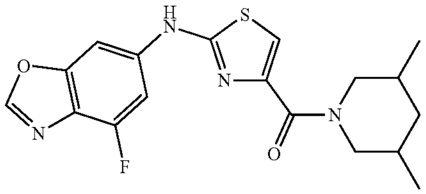 [SMILES: CC1CC(C)CN(C(=O)c2csc(Nc3cc(F)c4ncoc4c3)n2)C1] | N-{4-[3,5-dimethylpiperidine-1-carbonyl]-1,3-thiazol-2-yl}-4-fluoro-1,3-benzoxazol-6-amine |

Compound names, i.e., IUPAC names, for compounds described in the instant application were generated using JChem®™ compound naming software.

In a preferred embodiment, the compound of Formula I or Formula II or pharmaceutically acceptable salt thereof, is:

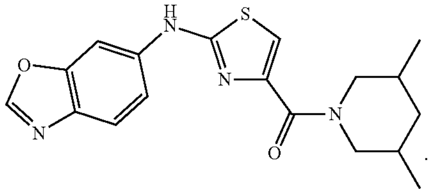 [SMILES: CC1CC(C)CN(C(=O)c2csc(Nc3ccc4ncoc4c3)n2)C1]

Where the compounds are chiral, the compound may exist as a racemic mixture, predominantly one enantiomer, or only one enantiomer.

The compound of Formula I or Formula II may exist in solid or liquid form. In the solid state, it may exist in crystalline or non-crystalline form, or as a mixture thereof. The skilled artisan will appreciate that pharmaceutically acceptable solvates may be formed for crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The person skilled in the art will appreciate that salts of the compounds according to Formula I or Formula II may be prepared. These salts may be prepared in situ during the isolation and purification of the compound, or by separately treating the purified compound in its free acid or free base form with a suitable base or acid, respectively.

The person skilled in the art will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compositions

The compounds of the invention will normally, but not necessarily, be formulated into a pharmaceutical composition prior to administration to a patient. Accordingly, in another aspect the invention is directed to pharmaceutical compositions comprising a compound of Formula I or Formula II, or a pharmaceutically acceptable salt thereof, as described in detail above, and a pharmaceutically acceptable excipient.

In a preferred embodiment, the compound in the composition of Formula I or Formula II, or pharmaceutically acceptable salt thereof, is

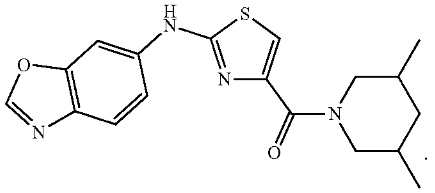 [SMILES: CC1CC(C)CN(C(=O)c2csc(Nc3ccc4ncoc4c3)n2)C1]

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

The pharmaceutical compositions of the invention may be prepared and packaged in bulk form wherein an effective amount of a compound of the invention can be extracted and then given to the patient such as with powders, syrups, and solutions for injection.

Alternatively, the pharmaceutical compositions of the invention may be prepared and packaged in unit dosage form wherein each physically discrete unit contains an effective amount of a compound of the invention. When prepared in unit dosage form, the pharmaceutical compositions of the invention typically contain from 1 mg to 1000 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention.

In addition, the pharmaceutical compositions of the invention may optionally further comprise one or more additional pharmaceutically active compounds (including, e.g., those described herein).

Combination therapies according to the present invention thus comprise the administration of a compound of Formula I or Formula II, or a pharmaceutically acceptable salt thereof, and at least one other therapeutically active agent. The compound(s) of Formula I or Formula II, and pharmaceutically acceptable salts thereof, and the other therapeutic agent(s) may be administered together in a single pharmaceutical composition.

In alternative embodiment, the compound(s) of Formula I or Formula II, or pharmaceutically acceptable salts thereof, and the other therapeutic agent(s) may be administered separately. In this embodiment, the compound(s) of Formula I or Formula II are prepared as a first medicament; and the other therapeutic agent(s) is prepared as a second medicament. Administration may be simultaneous (i.e. concurrent) or sequential in any order. The amounts of the compound(s) of Formula I or Formula II and pharmaceutically acceptable salts thereof, and the other therapeutic agent(s) and the relative timings of administration will be selected in order to achieve the desired combined therapeutic effect.

Thus in a further aspect, there is provided a combination comprising a compound of Formula I or Formula II, or a pharmaceutically acceptable salt thereof, together with one or more other therapeutic agents, wherein the combination may be a single medicament or a first and second medicament.

The pharmaceutical compositions of the invention including combination compositions typically include more than one pharmaceutically acceptable excipient. However, in certain embodiments, the pharmaceutical compositions of the invention contain one pharmaceutically acceptable excipient.

The compound of the invention and the pharmaceutically acceptable excipient or excipients will typically be formulated into a dosage form adapted for administration to the patient by the desired route of administration as noted above. For example, dosage forms include those adapted for (1) intranasal administration such as aerosol spray, solution, powder, suspension, emulsion, drops, single or multi-dose, with or without a preservative;
(2) inhalation such as aerosols and solutions;
(3) oral administration such as tablets, capsules, caplets, pills, troches, powders, syrups, elixirs, suspensions, solutions, emulsions, sachets, and cachets;
(4) parenteral administration such as sterile solutions, suspensions, and powders for reconstitution; and
(5) rectal administration such as suppositories.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms.

Certain pharmaceutically-acceptable excipients may be chosen for their ability to facilitate the carrying or transporting of the compound of the invention (or other compounds) once administered to the patient from one organ, or portion of the body, to another organ, or portion of the body. Certain pharmaceutically acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable e pharmaceutically acceptable excipients. Examples include Remington's Pharmaceutical Sciences (Mack Publishing Company, e.g., 18th Ed.), Remington: The Science and Practice of Pharmacy (Lippincott Williams & Wilkins. e.g., 21$^{st}$ Ed.), The Handbook of Pharmaceutical Additives (Gower Publishing Limited, e.g., 3$^{rd}$ Ed.), and The Handbook of Pharmaceutical Excipients (the American Pharmaceutical Association and the Pharmaceutical Press, e.g., 6$^{th}$ Ed.).

The pharmaceutical compositions of the invention are prepared using techniques and methods known to those skilled in the art. Some of the methods commonly used in the art are described in Remington's Pharmaceutical Sciences (Mack Publishing Company, e.g., 18th Ed).

Uses and Methods of Treatment

The blocking of TRPC3 or TRPC6 or TRPC7 ion channels, or any combination thereof, may be useful in the treatment of a neurological condition or disease including ischemia and reperfusion injury, including stroke and traumatic brain injury and the treatment of seizure, hemorrhage, brain trauma, epilepsy and Alzheimer's disease.

In addition to neurological indications, TRPC3, TRPC6 and TRPC7 ion channels play a pivotal role in a variety of diseases such as acute myocardial infarction and reperfusion (He, Le et. al. 2017), cardiac hypertrophy (Wu, Eder et al. 2010, Eder and Molkentin 2011), muscular dystrophy (Millay, Goonasekera et al. 2009), kidney diseases (Hall, Wang et al. 2019), pulmonary diseases (Maier, Follmann et al. 2015, Chen, Zhou et al. 2020), and blockade of these channels may be beneficial in these indications.

The compounds of this invention modulate the activity of TRPC3, TRPC6, TRPC7 ion channels, and accordingly, may provide a beneficial therapeutic impact in the prevention and treatment of diseases, disorders and/or conditions in which modulation of TRPC3, TRPC6, TRPC7 ion channels is beneficial. For example, for the treatment of neurological diseases and other diseases and/or disorders that involve activation of, or contribution by, one or more of the TRPC3, TRPC6 and TRPC7 ion channels, and therefore benefit from blocking (or inhibiting activity) of TRPC3, TRPC6 and TRPC7 ion channels.

Accordingly, in another aspect, the invention provides a method of inhibiting TRPC3, TRPC6, TRPC7 ion channel activity, or a combination thereof, comprising administering to a cell, tissue or an individual in need thereof, an effective amount of a compound of Formula I or Formula II as described herein, or a pharmaceutically acceptable salt thereof.

In another aspect, the invention provides a method of preventing or treating a condition or disease associated with TRPC3, TRPC6, or TRPC7 ion channel activity, or a combination thereof, in an individual in need thereof, comprising administering a compound of Formula I or Formula II as described herein, or a pharmaceutically acceptable salt thereof.

In another aspect, the present invention also provides a method of treating, or reducing the severity of a symptom of a disease or condition in an individual, wherein the disease or condition is associated with TRPC3, TRPC6, TRPC7 ion channel activity, or a combination thereof, comprising administering a therapeutically effective amount of a compound of Formula I or Formula II as described herein, or pharmaceutically acceptable salt thereof, thereby treating, or reducing the severity of the symptom of the disease or condition in the individual.

In another aspect, the invention provides the use of a compound of Formula I or Formula II as described herein, or a pharmaceutically acceptable salt thereof in the manufacture of a medicament for:

- inhibiting TRPC3, TRPC6, TRPC7 ion channel activity, or a combination thereof, in an individual in need thereof;
- preventing or treating a condition or disease associated with TRPC3, TRPC6, TRPC7 ion channel activity, or a combination thereof, in an individual in need thereof;
- treating, or reducing the severity of a symptom of a condition or disease associated with TRPC3, TRPC6, TRPC7 ion channel activity, or a combination thereof, in an individual in need thereof.

The condition or disease associated with TRPC3; TRPC6; TRPC7 ion channel activity may be responsive to the inhibition of TRPC3, TRPC6, TRPC7 ion channel activity.

In another aspect, the invention provides for the use of a compound of Formula I or Formula II as described herein, or a pharmaceutically acceptable salt thereof, for

- inhibiting TRPC3, TRPC6, TRPC7 ion channel activity, or a combination thereof, in an individual in need thereof;
- preventing or treating a condition or disease associated with TRPC3, TRPC6, TRPC7 ion channel activity, or a combination thereof, in an individual in need thereof;
- treating, or reducing the severity of a symptom of a condition or disease associated with TRPC3, TRPC6, TRPC7 ion channel activity, or a combination thereof, in an individual in need thereof.

In each of the above aspects and embodiments of the invention, the condition or disease associated with TRPC3, TRPC6, or TRPC7 ion channel activity may be a neurological condition or disease, cardiac failure, cardiac hypertrophy, muscular dystrophy, a kidney disease or a pulmonary disease.

Preferably the condition or disease associated with TRPC3, TRPC6, or TRPC7 ion channel activity is a neurological condition or disease, wherein more preferably the neurological condition or disease is selected from one or more of ischemia, haemorrhage, concussion, brain injury/traumatic brain injury (TBI), epilepsy, and Alzheimer's disease.

In some embodiments, the disease or condition is mediated by all three of TRPC3, TRPC6, and TRPC7 ion channels, and more specifically, inhibition or blocking of those channels. In some embodiments the condition or disease is associated with one of TRPC3 or TRPC6 or TRPC7 activity. In some embodiments the condition or disease is associated with TRPC3 and TRPC6 activity, in some embodiments the condition or disease is associated with TRPC6 and TRPC7 activity and in some embodiments the condition or disease is associated with TRPC3 and TRPC7 activity. While inhibition or blocking of one or more of TRPC3, TRPC6, TRPC7 ion channels in each of the abovementioned methods and uses is likely to achieve a therapeutic and/or prophylactic outcome, the compound of Formula I or Formula II preferably works against all three of them for maximum therapeutic or prophylactic efficacy.

An effective amount of a compound in both of the above contexts will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

A "subject" herein is preferably a human subject. It will be understood that the terms "subject" and "individual" and "patient" are interchangeable in relation to an individual requiring treatment according to the present invention.

Although the invention finds application in humans, the invention is also useful for therapeutic veterinary purposes. The invention is useful for domestic or farm animals such as cattle, sheep, horses and poultry; for companion animals such as cats and dogs; and for zoo animals.

The compounds of the invention may be administered by any suitable route of administration, including systemic administration. Systemic administration includes intranasal administration, administration by inhalation, oral administration, parenteral administration, and rectal administration. Parenteral administration refers to routes of administration other than enteral, transdermal, or by inhalation, and is typically by injection or infusion. Parenteral administration includes intravenous, intramuscular, and subcutaneous injection or infusion, optionally including a loading bolus dose. Inhalation refers to administration into the patient's lungs whether inhaled through the mouth or through the nasal passages. In some embodiments, a compound of the invention is administered intravenously, by inhalation, or orally.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan.

The timing of administration may also vary depending on the condition or disease being treated. An acute condition, such as ischemia, hemorrhage, concussion or other brain injury will benefit from administration of the compound of Formula I preferably within 24 hours after the injury occurs, more preferably within 12 hours, with optional follow up treatment where it is indicated. Chronic conditions, such as, epilepsy, and Alzheimer's disease will benefit from longer term administration of Formula I.

Acute dosing may initiate immediately following injury and preferably within 24 hours, more preferably within 12 hours following the injury.

In addition, suitable dosing regimens, including the duration such regimens are administered, for a compound of the invention depend on the condition being treated, the severity of the condition being treated, the age and physical condition of the patient being treated, the medical history of the patient to be treated and any comorbidities, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Methods of prevention or treatment of the invention may be achieved using the compounds of the invention as a monotherapy, or in dual or multiple combination therapy with one or more therapeutic agents or therapies. For example, one or more compounds of the invention may be used in combination. One or more compounds of the invention may also be used with one or more other therapeutic agents or therapies. The one or more other therapeutic agents of therapies include but are not limited to: sedative pain medication, anticonvulsants, diuretics, tissue plasminogen activator (tPA), saline, iv nutrition, and combinations thereof.

The present invention includes the use of a compound of Formula I or Formula II or salt thereof as a blocker (or antagonist or inhibitor) of TRPC3, TRPC6, TRPC7 ion channel over-activity, or a combination thereof (e.g. in in vitro or in vivo assays or in a subject in need thereof). Accordingly, compounds of Formula I may be used to identify compounds which inhibit TRPC3, TRPC6, TRPC7 ion channel over-activity, or combinations thereof, for example by using a compound of Formula I as a control compound in an assay or model which measures TRPC3, TRPC6, TRPC7 ion channel activity, or combinations thereof, including any biological assays described herein.

It will be understood that the invention disclosed and defined in this specification extends to all alternative combinations of two or more of the individual features mentioned or evident from the text or drawings. All these different combinations constitute various alternative aspects of the invention.

EXAMPLES

Compound Preparation

The compounds according to Formula I are prepared using conventional organic syntheses. Suitable synthetic routes are depicted below in the following general reaction schemes. All functional groups are as defined in the respective Schemes for corresponding groups unless otherwise defined. Starting materials and reagents depicted below in the general reaction schemes are commercially available or can be made from commercially available starting materials using methods known by those skilled in the art.

Scheme 1

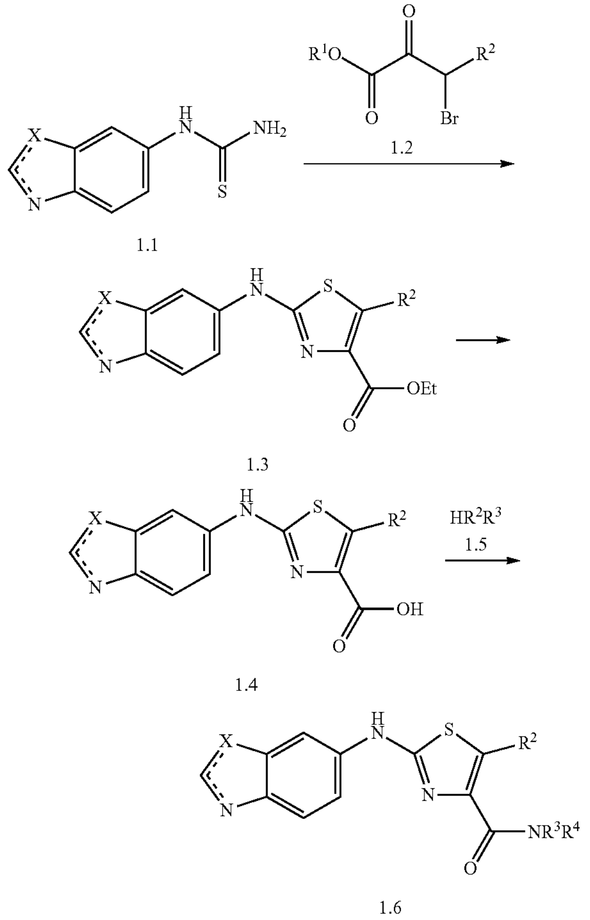

1.1
1.2
1.3
1.4
1.5
1.6

Scheme 1 represents a general reaction scheme for preparing general compounds according to Formula I (depicted as compound 1.6). Treatment of thiourea 1.1 (commercially available or made from commercially available starting materials using methods known to those skilled in the art) with 2-oxo ester 1.2 in a solvent (such as ethanol) provides intermediates 1.3. The intermediate compound 1.3 is treated with base (such as LiOH or equivalent) in a solvent (such as THF or a mixture of THF/MeOH/water) gives intermediate 1.4. Next, reaction of intermediate 1.4 with an amine 1.5, a coupling agent (such as HATU or EDCI with HOBt) and a base (such as DIPEA or $NEt_3$) in a solvent (such as DMF) provides compounds 1.6 according to Formula I.

Scheme 2

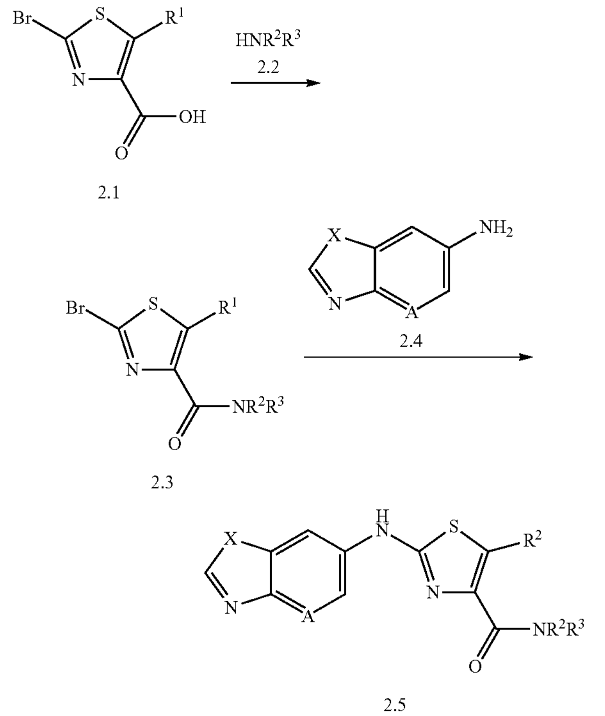

2.1
2.2
2.3
2.4
2.5

Scheme 2 represents an alternative general reaction scheme for preparing certain compounds according to Formula I (depicted as compound 2.5). Treatment of thiazole 2.1 with an amine reagent 2.2, a coupling agent (such as EDCI with HOBt) and a base (such as $NEt_3$) in a solvent (such as DMF) provides intermediates 2.3. Next, reaction of intermediate 2.3 with an arylamine 2.4, a coupling agent (such as HATU or EDCI with HOBt) and a base (such as DIPEA or $NEt_3$) in a solvent (such as DMF) provides compounds 2.5 according to Formula I.

Scheme 3

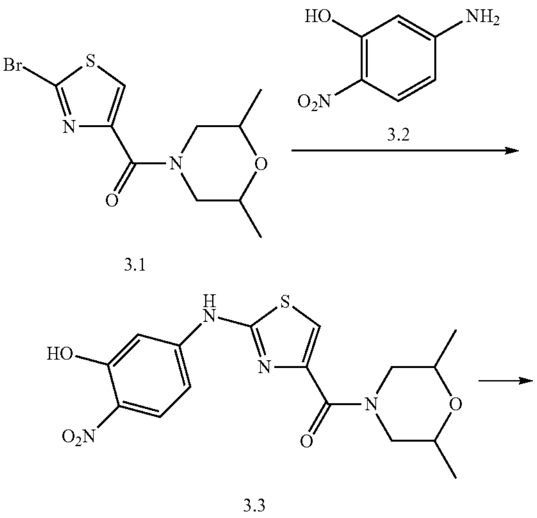
3.1
3.2
3.3

-continued

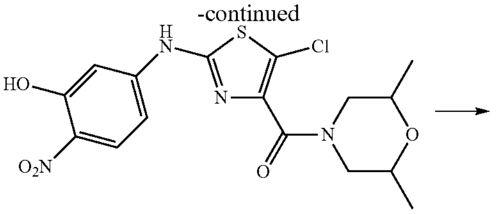

3.4

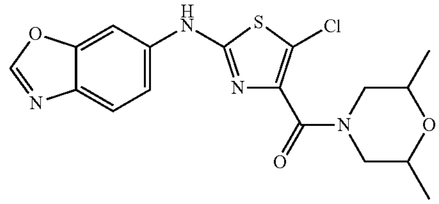

3.5

Scheme 3 represents a further alternative general reaction scheme for preparing certain compounds according to Formula I (depicted as compound 3.5). Treatment of thiazole amide 3.1 with an aniline reagent 3.2, an organopalladium coupling agent (such as $Pd_2(dba)_3$ with Xantphos) and a base (such as $Cs_2CO_3$) in a solvent (such as toluene) provides intermediates 3.3. The intermediate compound 3.3 is with a chlorinating agent (such as NCS) in a solvent (such as THF) gives intermediate 3.4. Next, reaction of intermediate 3.4 with an organometallic catalyst (such as $PtO_2$), zinc chloride and triethylorthoformate in a solvent (such as MeOH) under an atmosphere of hydrogen provides compounds 3.5 according to Formula I.

Scheme 4

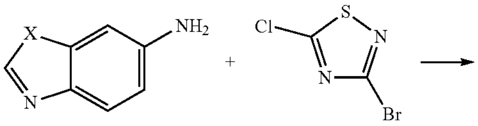

4.1 4.2

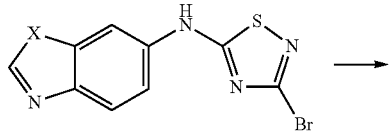

4.3

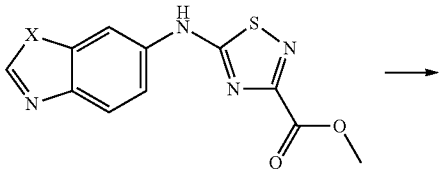

4.4

-continued

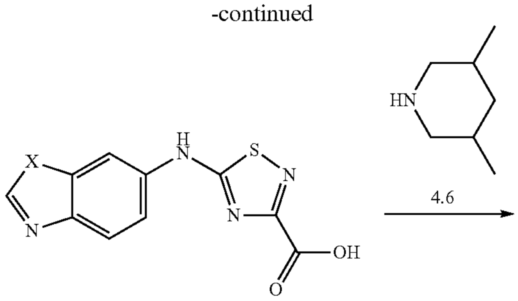

4.5

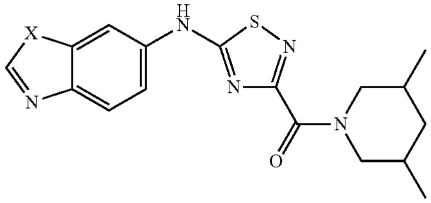

4.7

Scheme 4 represents a further alternative general reaction scheme for preparing certain compounds according to Formula I (depicted as compound 4.7). Treatment of aniline 4.1 with thiadiazole 4.2 in a solvent (such as DMF) provides intermediates 4.3. The intermediate compound 4.3 and a base (such as $NEt_3$) in a solvent (such as MeOH/DMF) with a palladium catalyst (such as $Pd(dppf)Cl_2$) under a carbon monoxide atmosphere gives intermediate 4.4. The intermediate compound 4.4 is treated with base such as LiOH or equivalent in a solvent (such as a mixture of THF/MeOH/water) gives intermediate 4.5. Next, reaction of intermediate 4.5 with amine 4.6, coupling agents (such as TCHF and an imidazole) in a solvent (such as ACN) provides compounds 4.7 according to Formula I.

Scheme 5

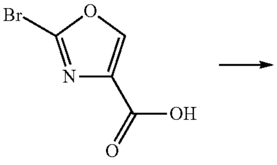

5.1

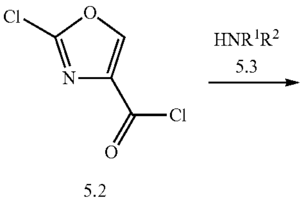

5.2

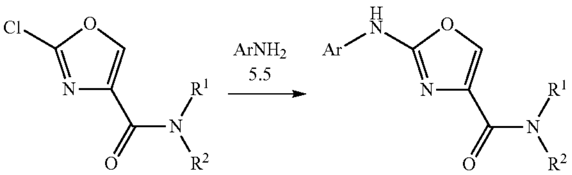

5.4 5.6

Scheme 5 represents a further alternative general reaction scheme for preparing certain compounds according to Formula I (depicted as compound 5.6). Treatment of oxazole 5.1 in a solvent (such as $CH_2Cl_2$) with a chlorinating agent (such as $SOCl_2$) in a solvent (such as DMF) provides intermediates 5.2. The intermediate compound 5.2 is treated with an alkylamine reagent 5.3 in a solvent (such as DCM) gives intermediate 5.4. Next, reaction of intermediate 5.4 with arylamine 5.5, an organopalladium coupling agent (such as $Pd_2(dba)_3$ with Xantphos) and a base (such as $Cs_2CO_3$) in a solvent (such as dioxane) provides compounds 5.6 according to Formula I.

EXPERIMENTAL

General information: All evaporations were carried out under reduced pressure with a rotary evaporator. Analytical samples were dried under reduced pressure (1-5 mmHg) at room temperature. Thin layer chromatography (TLC) was performed on silica gel 60 F254 aluminium-backed plates, spots were visualized by UV light (214 nm and 254 nm). Purification by column and flash chromatography was carried out using silica gel (300-400 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated, the general LCMS condition was as follows: Waters X Bridge C18 column (50 mm×4.6 mm×3.5 μm), Flow Rate: 2.0 mL/min, the column temperature: 40° C.

The following solvents, reagents or scientific terminology may be referred to by their abbreviations:

TLC Thin Layer Chromatography
mL milliliters
mmol millimole
h hour or hours
min minute or minutes
g gram
mg milligram
eq equivalent
rt room temperature, ambient, about 25° C.
RT Retention Time
MS mass spectrometry
ESI Electrospray ionization
m/z mass to charge ratio
nmr Nuclear Magnetic Resonance
Hz Hertz
HPLC high performance liquid chromatography
LC/MS Liquid chromatography/mass spectrometry
DCM dichloromethane
EtOAc ethyl acetate
HATU hexafluorophosphate azabenzotriazole tetramethyl uronium
DMF N,N-dimethylformamide
EtOH ethanol
MeOH methanol
PE petroleum ether
DIPEA diisopropylethylamine
TCHF N-chloro(dimethylamino)methylene)-N-methylmethanaminium hexafluorophosphate (V)
THF tetrahydrofuran
EDCI 1-ethyl-3-(3-dimethylaminopropyl) carbodiimide
HOBt hydroxybenzotriazole

Synthesis of Starting Materials

Scheme 1a: Experimental procedure for the synthesis of 2,3-dimethylpiperidine 716-1 for Compound 16

Experimental procedure for General Scheme 1a:

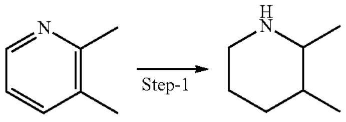

716-0 716-1

In a 50 mL autoclave, to a solution of 2,3-dimethylpyridine (716-0, 6.0 g, 56.0 mmol) in acetic acid (20 mL) was added $PtO_2$ (300 mg). The final mixture was stirred at room temperature under hydrogen atmosphere (at 10 atm pressure) overnight. The reaction mixture was concentrated in vacuo to give a residue and the residue was diluted by a 0.5 M NaOH aqueous solution (100 mL) and hexane (200 mL). The mixture was stirred at room temperature for 15 min and layers were separated. The organic layer was dried over anhydrous $Na_2SO_4$ and concentrated in vacuo to provide 2,3-dimethylpiperidine (716-1, 4.0 g, 63%) as a clear oil. LC/MS (ESI): m/z=114.4 $[M+1]^+$. RT=1.06 min.

Scheme 1b: Experimental Procedure for the Synthesis of 789-2 for Compound 26

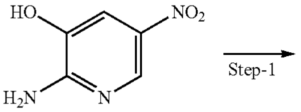

789-0

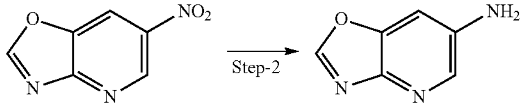

789-1 789-2

Experimental Procedure for General Scheme 1b

Step-1: A mixture of 2-amino-5-nitropyridin-3-ol (789-0, 300 mg, 1.93 mmol) and $HC(OC_2H_5)_3$ (5 mL) was stirred at 100° C. overnight. After the raw materials are consumed, the mixture was cooled to room temperature, concentrated and purified by flash column chromatography (eluting with 9% EtOAc in PE) to give 789-1 (150 mg, 47%) as a yellow solid. LC/MS (ESI): m/z=166.2 $[M+H]^+$. RT=1.188 min.

Step-2: To a solution of 789-1 (150 mg, 0.91 mmol) in MeOH (40 mL) was add 10% Pd/C (100 mg) and the reaction mixture was allowed to stir at room temperature overnight under hydrogen atmosphere. After all the raw material was consumed, the reaction mixture was filtered through celite and the filtrate was concentrated to give 789-2

(67 mg, 55% yield) as a yellow solid. LC/MS (ESI): m/z=136.3 $[M+H]^+$. RT=0.652 min.

Scheme 1c: Experimental Procedure for the Synthesis of 781-6 for Compound 27

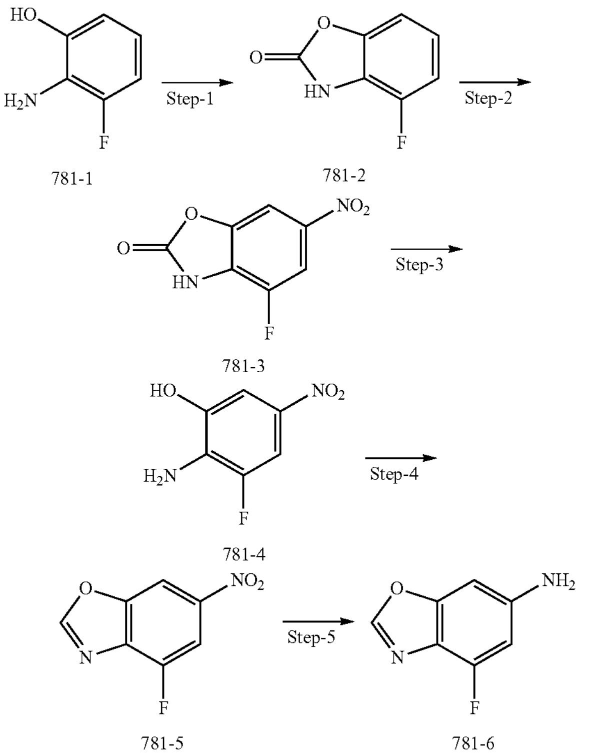

781-1 781-2 781-3 781-4 781-5 781-6

Experimental Procedure for Scheme 1c

Step-1: A mixture of 2-amino-3-fluorophenol (781-1, 2.50 g, 19.67 mmol) and CDI (3.19 g, 19.67 mmol) in THF (100 mL) was stirred at 60° C. for 2 h. After consumption of the starting material, the mixture was evaporated under reduced pressure to give crude 781-2 (2.80 g, 93% yield) as a yellow solid. $^1H$ NMR (400 MHz, $CDCl_3$) δ: 9.14 (s, 1H), 7.81 (s, 1H), 7.14 (s, 1H), 7.04-6.91 (m, 1H).

Step-2: A mixture of 781-2 (2.80 g, 18.29 mmol) in concentrated $H_2SO_4$ (20 mL) was cooled to −10° C. To the mixture was added 70% $HNO_3$ (0.8 mL, 18.80 mmol) dropwise, and the mixture was stirred for 30 min at −10° C. The mixture was poured into ice-water (50 mL) slowly and extracted with $CH_2Cl_2$ (2×50 mL). The organic phase was washed with aq $NaHCO_3$ and brine, dried over $Na_2SO_4$, evaporated and purified by column chromatography (0-5% MeOH in $CH_2Cl_2$) to give 781-3 (1.70 g, 47% yield) as a yellow solid. $^1H$ NMR (400 MHz, DMSO-$d_6$) δ: 13.09 (s, 1H), 8.18-8.14 (m, 2H).

Step-3: A suspension of 781-3 (1.70 g, 8.58 mmol), NaOH (2.16 g, 54.0 mmol) in $H_2O$ (100 mL) was stirred at 100° C. overnight. After consumption of starting material (monitored by LCMS), the reaction mixture is cooled to room temperature and carefully neutralized with 6N aqueous hydrochloric acid. The resulting precipitate is filtered, washed with water and dried under vacuum to give 781-4 (900 mg, 61% yield) as a brown solid. LC/MS (ESI): m/z=173.2 $[M+H]^+$. RT=1.378 min.

Step-4: A mixture of 781-4 (900 mg, 5.23 mmol) and $HC(OC_2H_5)_3$ (8 mL) was stirred at 100° C. for 4 hours, After all the raw materials are consumed, the reaction liquid was cooled to room temperature, the ethanol was volatilized, crystallized, filtered and then washed the crystallized with hexane several times to give 781-5 (130 mg, 14%) as a yellow solid. $^1H$ NMR (400 MHz, $CDCl_3$) δ: 8.39 (d, J=1.2 Hz, 1H), 8.35 (s, 1H), 8.09 (dd, J=9.2, 2.0 Hz, 1H).

Step-5: A mixture of 781-5 (120 mg, 0.66 mmol), Fe (198 mg, 3.54 mmol) and $NH_4Cl$ (190 mg, 3.54 mmol) in EtOH (12 mL) and $H_2O$ (4 mL) was stirred at 60° C. overnight. After the raw materials are consumed, the reaction mixture was filtered through celite, the filtrate was diluted by water (20 mL) and extracted with EtOAc (3×20 mL). The organic was washed by brine (50 mL), dried over anhydrous $Na_2SO_4$, filtered, evaporated under reduced pressure and purified by column chromatography on silica gel (eluting with 0%~30% EtOAc in hexane) to give 781-6 (50 mg, 50% yield) as a yellow solid. LC/MS (ESI): m/z=153.2 $[M+H]^+$. RT=1.219 min.

General Scheme 1: Experimental Procedure for the Synthesis of Compounds 10 and 25

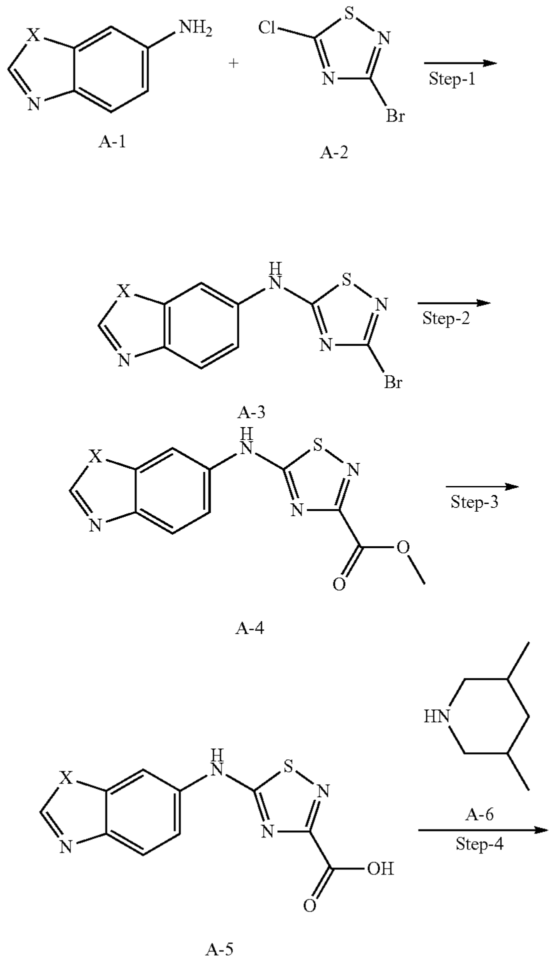

A-1 A-2 A-3 A-4 A-5

-continued

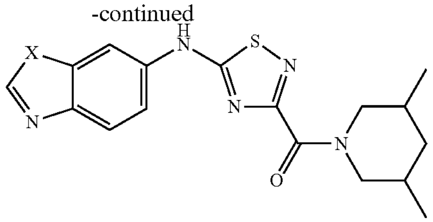

A-7

X=O or S

Experimental Procedure for General Scheme 1

A-7 as Compound 10—Step-1 X=S: A mixture of arylamine A-1 (750 mg, 5.0 mmol) and thiadiazole A-2 (1.0 g, 5.0 mmol) in DMF (30 mL) was heated to 90° C. and stirred overnight. After consumption of the starting material, the reaction mixture was diluted by water (50 mL) and extracted with EtOAc (2×55 mL). The organic extract was washed by water (4×100 mL) and brine (50 mL) successively, dried over anhydrous $Na_2SO_4$, filtered and evaporated under reduced pressure to give bromothiadiazole A-3 (1.33 g, 85% yield) as a green solid. LC/MS (ESI): m/z=312.9 $[M+1]^+$. RT=1.836 min.

Step-2: A mixture of heteroaryl halide A-3 (1.33 g, 4.25 mmol), Pd(dppf)$Cl_2$ (620 mg, 0.85 mmol) and $Et_3N$ (5 mL) in MeOH (60 mL) and DMF (30 mL) was heated to 55° C. and stirred overnight under CO atmosphere. After consumption of the starting material, the reaction mixture was concentrated to remove MeOH, diluted by water (50 mL) and extracted with EtOAc (2×50 mL). The organic extract was washed by water (4×100 mL) and brine (50 mL) successively, dried over anhydrous $Na_2SO_4$, filtered, evaporated and purified by column chromatography on silica gel (eluting with 40% EtOAc in hexane) to give ester A-4. LC/MS (ESI): m/z=293.1 $[M+1]^+$. RT=1.552 min.

Step-3: To a solution of ester A-4 (200 mg, 0.72 mmol) in THF (5 mL), MeOH (5 mL) and $H_2O$ (5 mL) was added LiOH·$H_2O$ (300 mg, 7.2 mmol), and the reaction mixture was stirred at room temperature overnight. After consumption of the starting material, it was diluted by water (20 mL), evaporated to remove MeOH and THF, and acidified by aqueous HCl with stirring to give a precipitate. The precipitate was collected by suction, washed by water and dried to give carboxylic acid A-5 (170 mg, 89.5% yield) as a light-yellow solid. LC/MS (ESI): m/z=279.1 $[M+1]^+$. RT=1.035 min.

Step-4: To a solution of heterocarboxylic acid A-5 (160 mg, 0.57 mmol) and 3,5-dimethylpiperidine A-6 (98 mg, 0.86 mmol) in $CH_3CN$ (20 mL) was added TCHF (210 mg, 0.75 mmol) and 1-methyl-1H-imidazole (165 mg, 2.0 mmol), and the reaction mixture was allowed to stir at room temperature overnight. After consumption of the starting material, the reaction mixture was diluted by water (30 mL) and extracted with EtOAc (2×20 mL). The organic extract was washed by water (30 mL) and brine (30 mL) successively, dried over anhydrous $Na_2SO_4$, filtered and evaporated under reduced pressure to give a residue. The residue was purified by reversed phase Prep-HPLC to give A-7 as Compound 10 (95 mg, 44% yield) as a white solid. $^1$H NMR (400 MHz, DMSO-$d_6$) δ 11.38 (s, 1H), 9.30 (s, 1H), 8.47 (d, J=2.0 Hz, 1H), 8.10 (d, J=8.4 Hz, 1H), 7.63 (dd, J=8.8, 2.4 Hz, 1H), 4.45-4.41 (m, 1H), 3.51-3.48 (m, 1H), 2.60 (t, J=11.6 Hz, 1H), 2.21 (t, J=12.4 Hz, 1H), 1.82 (d, J=12.8 Hz, 1H), 1.69-1.56 (m, 2H), 0.93-0.77 (m, 7H). LC/MS (ESI): m/z=374.2 $[M+1]^+$. RT=8.498 min.

A-7 as Compound 25—Step-1 X=O: A mixture of arylamine A-1 (1.35 g, 10.0 mmol) and thiadiazole A-2 (0.94 g, 10.0 mmol) in DMF (60 mL) was heated to 90° C. and stirred overnight. After consumption of the starting material, the reaction mixture was diluted by water (100 mL) and extracted with EtOAc (2×50 mL). The organic extract was washed by water (4×100 mL) and brine (50 mL) successively, dried over anhydrous $Na_2SO_4$, filtered and evaporated under reduced pressure to give bromothiadiazole A-3 (1.75 g, 59% yield) as reddish-brown solid. LC/MS (ESI): m/z=297 $[M+1]^+$. RT=1.677 min.

Step-2: A mixture of heteroaryl halide A-3 (1.75 g, 5.91 mmol), Pd(dppf)$Cl_2$ (865 mg, 1.18 mmol) and $Et_3N$ (6 mL) in MeOH (60 mL) and DMF (30 mL) was heated to 55° C. and stirred overnight under CO atmosphere. After consumption of the starting material, the reaction mixture was concentrated to remove MeOH, diluted by water (50 mL) and extracted with EtOAc (2×50 mL). The organic extract was washed by water (4×100 mL) and brine (50 mL) successively, dried over anhydrous $Na_2SO_4$, filtered, evaporated and purified by column chromatography on silica gel (eluting with 40% EtOAc in hexane) to give ester A-4. (1.0 g, 61% yield) as a reddish-brown solid. LC/MS (ESI): m/z=277 $[M+1]^+$. RT=1.459 min.

Step-3: To a solution of ester A-4 (1 eq.) in THF (30 mL), MeOH (30 mL) and $H_2O$ (30 mL) was added LiOH·$H_2O$ (1.52 g, 36.2 mmol), and the reaction mixture was stirred at room temperature overnight. After consumption of the starting material, it was diluted by water (80 mL), evaporated to remove MeOH and THE, and acidified by aqueous HCl with stirring to give a precipitate. The precipitate was collected by suction, washed by water and dried to give carboxylic acid A-5 (800 mg, 84% yield) as a reddish-brown solid. LC/MS (ESI): m/z=263.1 $[M+1]^+$. RT=0.903 min.

Step-4: To a solution of heterocarboxylic acid A-5 (800 mg, 3.05 mmol) and 3,5-dimethylpiperidine A-6 (0.6 mL, 4.58 mmol) in DMF (40 mL) was added TCHF (2.59 g, 10.71 mmol) and 1-methyl-1H-imidazole (0.84 mL, 10.71 mL), and the reaction mixture was allowed to stir at room temperature overnight. After consumption of the starting material, the reaction mixture was diluted by water (100 mL) and extracted with EtOAc (2×50 mL). The organic extract was washed by water (4×100 mL) and brine (50 mL) successively, dried over anhydrous $Na_2SO_4$, filtered and evaporated under reduced pressure to give a residue. The residue was purified by reversed phase Prep-HPLC to give A-7 as Compound 25 (28 mg, 2.5% yield) as an off-white solid. $^1$H NMR (400 MHz, $CD_3OD$) δ 8.44 (s, 1H), 8.30 (d, J=2.0 Hz, 1H), 7.73 (d, J=8.8 Hz, 1H), 7.40 (dd, J=8.8, 2.0 Hz, 1H), 4.61-4.57 (m, 1H), 3.76-3.72 (m, 1H), 2.66 (t, J=12.4 Hz, 1H), 2.36 (t, J=12.4 Hz, 1H), 1.93-1.90 (m, 1H), 1.80-1.72 (m, 2H), 1.00 (d, J=2.8 Hz, 3H), 0.96-0.86 (m, 1H), 0.85 (d, J=6.8 Hz, 3H). LC/MS (ESI): m/z=358.2 $[M+1]^+$. RT=9.098 min.

General Scheme 2: Experimental Procedure for the Synthesis of Compounds 17 and 18

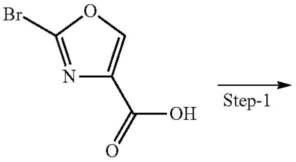

A-8

-continued

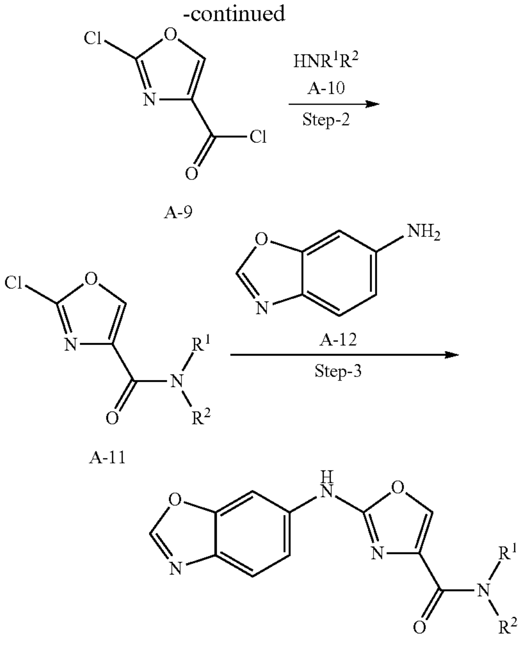

A-9

A-11

A-13

$R^1\&R^2$=—$CH_2CH(CH_3)CH_2CH(CH_3)CH_2$— or —$(CH_2)_3CH((R)CH_3)CH((R)CH_3)$—

Experimental Procedure for General Scheme 2

Step-1: To a solution of oxazole A-8 (576 mg, 3.0 mmol) in $CH_2Cl_2$ (30 mL) was added $SOCl_2$ (3.0 mL) and DMF (0.1 mL). The reaction mixture was stirred at room temperature overnight and then concentrated in vacuo to remove volatile substance to provide A-9 as a clear oil which was used for the next step directly.

Step-2: To a solution of aryl acid chloride A-9 (498 mg, 3.0 mmol) in $CH_2Cl_2$ (25 mL) was added a solution of $Et_3N$ (3.0 mL) and secondary alkyl amine A-10 (1 eq. 3.0 mmol) in $CH_2Cl_2$ (25 mL). The reaction mixture was stirred at room temperature for 2 h and concentrated in vacuo to give a residue. The residue was purified by column chromatography on silica gel (eluting with 20% EtOAc in PE) to give aryl amide A-11.

Step-3: To a solution of oxazole A-11 (400 mg, 1.65 mmol) and arylamine A-12 (1.2 eq. 2.0 mmol) in 1,4-dioxane (50 mL) was added $Cs_2CO_3$ (1.04 g, 3.2 mmol), $Pd_2(dba)_3$ (183 mg, 0.20 mmol) and Xantphos (115 mg, 0.20 mmol). The mixture was stirred at 100° C. overnight under argon atmosphere. After the raw materials were consumed, the reaction mixture was filtered through a celite pad to remove the solid and the filtrate was evaporated under reduced pressure and purified by reversed phase Prep-HPLC to give A-13.

General Scheme 2 was used to prepare the following compounds, with the functional groups as specified:

A-13 as Compound 17—Step-2 $R^1\&R^2$=—$CH_2CH(CH_3)CH_2CH(CH_3)CH_2$-(110 mg, 19.6% yield) as a white solid. $^1H$ NMR (400 MHz, DMSO-$d_6$) δ 10.66 (s, 1H), 8.62 (s, 1H), 8.28 (d, J=1.6 Hz, 1H), 8.09 (s, 1H), 7.72 (d, J=8.4 Hz, 1H), 7.40 (dd, J=8.4, 2.0 Hz, 1H), 4.84 (s, 1H), 4.45 (s, 1H), 2.57 (s, 1H), 2.20 (s, 1H), 1.86-1.57 (m, 3H), 0.93-0.81 (m, 7H). LC/MS (ESI): m/z=341.2 $[M+1]^+$. RT=8.623 min.

A-13 as Compound 18—Step-2 $R^1\&R^2$=—$(CH_2)_3CH(CH_3)CH(CH_3)$— (20 mg, 3.6% yield) as a white solid. $^1H$ NMR (400 MHz, DMSO-$d_6$) δ 10.63 (s, 1H), 8.62 (s, 1H), 8.31 (s, 1H), 8.05 (d, J=3.2 Hz, 1H), 7.72 (d, J=8.4 Hz, 1H), 7.40 (dd, J=8.8, 1.6 Hz, 1H), 4.87-4.35 (m, 2H), 3.06-2.78 (m, 1H), 1.94-1.16 (m, 8.0H), 1.01-0.89 (m, 3H). LC/MS (ESI): m/z=341.2 $[M+1]^+$. RT=8.319 min.

General Scheme 3: Experimental Procedure for the Synthesis of Compound 8

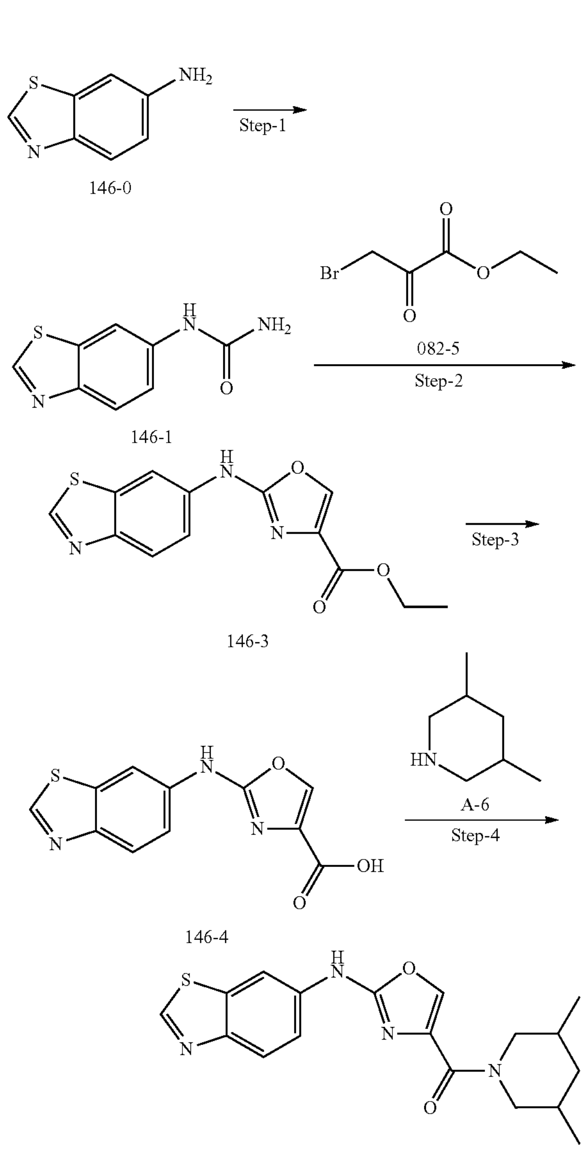

146-0

146-1

146-3

146-4

Compound 8

Experimental Procedure for General Scheme 3

Step-1: A mixture of arylamine 146-0 (500 mg, 3.33 mmol) and CNOK (2.20 g, 33.30 mmol) in AcOH (5 mL) and $H_2O$ (45 mL) was stirred at room temperature for 0.5 h. After consumption of the starting material, the reaction mixture was extracted with EtOAc (3×50 mL). The organic extract was washed by brine (100 mL), dried over anhydrous $Na_2SO_4$ and concentrated to give crude arylurea 146-1 (525 mg, 81% yield) as a white solid. LC/MS (ESI): m/z=194.2 $[M+1]^+$. RT=0.899 min.

Step-2: To a solution of arylurea 146-1 (500 mg, 2.59 mmol) in DMF (20 mL) was added ethyl 3-bromo-2-oxobutanoate 082-5 (758 mg, 3.89 mmol), and the reaction mixture was heated to 90° C. and stirred overnight. After consumption of the starting material, the reaction mixture was diluted by water (50 mL) and extracted with EtOAc (3×50 mL). The organic extract was washed by water (3×100 mL) and brine (100 mL) successively, dried over anhydrous $Na_2SO_4$, concentrated and purified by column chromatography (eluting with 50% EtOAc in PE) to give oxazole 146-3 (200 mg, 26.7% yield) as a yellow solid. LC/MS (ESI): m/z=290.0 $[M+1]^+$. RT=1.600 min.

Step-3: To a solution of oxazole 146-3 (200 mg, 0.69 mmol) in THF (10 mL), MeOH (10 mL) and $H_2O$ (10 mL) was added NaOH (400 mg, 10.0 mmol), and the reaction mixture was stirred at room temperature overnight. After consumption of the starting material, it was diluted by water (20 mL), evaporated to remove MeOH and THF, and acidified by aqueous HCl with stirring to give a precipitate. The precipitate was collected by suction, washed by water and dried to give carboxylic acid 146-4 (120 mg, 66.7% yield) as a yellow solid. LC/MS (ESI): m/z=262.0 $[M+1]^+$. RT=0.793 min.

Step-4: To a solution of carboxylic acid 146-4 (120 mg, 0.46 mmol) and amine A-5 (62 mg, 0.55 mmol) in DMF (15 mL) was added EDCI·HCl (132 mg, 0.69 mmol), HOBT (93 mg, 0.698 mmol) and $Et_3N$ (139 mg, 1.38 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give Compound 8 (7.0 mg, 4.3% yield) as a white solid. $^1H$ NMR (400 MHz, DMSO-$d_6$) δ 10.66 (s, 1H), 9.21 (s, 1H), 8.56 (d, J=2.0 Hz, 1H), 8.10 (s, 1H), 8.02 (d, J=9.2 Hz, 1H), 7.56 (dd, J=8.8, 2.0 Hz, 1H), 4.84-4.82 (m, 1H), 4.45-4.42 (m, 1H), 2.50-2.53 (m, 1H), 2.23-2.16 (m, 1H), 1.86 (d, J=12.4 Hz, 1H), 1.79-1.73 (m, 1H), 1.57-1.54 (m, 1H), 0.93-0.81 (m, 7H). LC/MS (ESI): m/z=357.0 $[M+1]^+$. RT=8.605 min.

General Scheme 4: Experimental Procedure for the Synthesis of Compounds 2, 3, 4, 5, 6, 7, 9, 11, 12

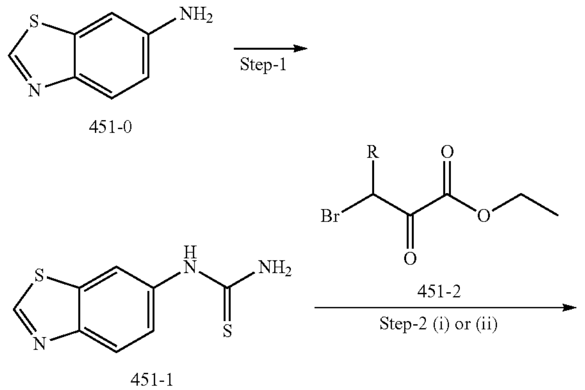

451-0

451-1

451-2

-continued

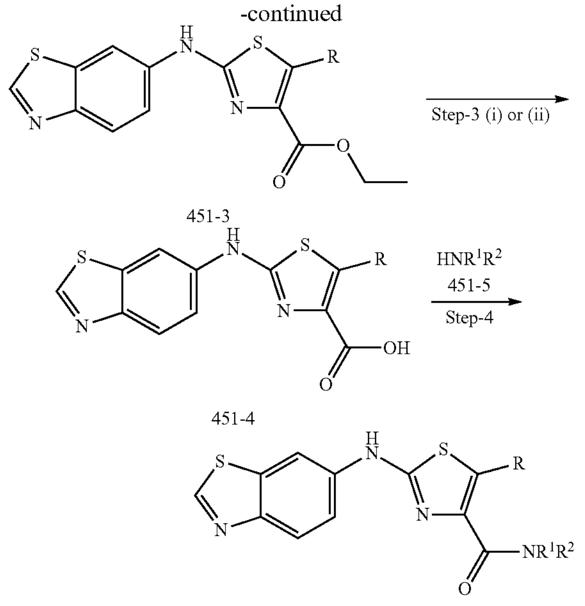

451-3

451-4

451-6

R=H or $CH_3$;

$R^1$&$R^2$=—$CH_2CH(CH_3)CH_2CH(CH_3)CH_2$— or —$CH_2CH(CH_3)$ $OCH(CH_3)CH_2$— or —$(CH_2)_7$— or —$(CH_2)_5$— or —$CH(CH_3)$ $(CH_2)_3CH(CH_3)$— or —$(CH_2)_3CH(CH_3)CH_2$— or —$(CH_2)_3CH(CH_3)$ $CH_2$—

Experimental Procedure for General Scheme 4

Step-1: A mixture of aryl amine 451-0 (7.50 g, 49.93 mmol) and $NH_4SCN$ (19.0 g, 249.67 mmol) in 1N aqueous HCl (100 mL) was stirred at 100° C. for 3 days. After consumption of the starting material, the reaction mixture was cooled to room temperature, filtered to collect the precipitate and dried to give arylthiourea 451-1 (8.40 g, 80.4% yield) as a black solid.

Step-2 (i): To a solution of 451-1 (2.30 g, 10.99 mmol) in EtOH (50 mL) was added ethyl 3-bromo-2-oxobutanoate 451-2 (2.14 g, 10.99 mmol), and the reaction mixture was heated to reflux and stirred overnight. After consumption of the starting material, the reaction mixture was concentrated to give crude thiazole 451-3 (1.90 g, 56.6% yield) as a black solid. LC/MS (ESI): m/z=306.0 $[M+1]^+$. RT=1.665 min.

Step-2 (ii): To a solution of 451-1 (210 mg, 1.0 mmol) in EtOH (20 mL) was added ethyl 3-bromo-2-oxobutanoate 451-2 (210 mg, 1.0 mmol), and the reaction mixture was heated to reflux and stirred overnight. After consumption of the starting material, the reaction mixture was concentrated to give crude thiazole 451-3 (320 mg, 99% yield) as a black solid. LC/MS (ESI): m/z=320.0 $[M+1]^+$. RT=1.917 min.

Step-3 (i): To a solution of thiazole 451-3 (1.90 g, 6.22 mmol) in THF (20 mL), MeOH (20 mL) and $H_2O$ (20 mL) was added $LiOH·H_2O$ (840 mg, 20.0 mmol), and the reaction mixture was stirred at room temperature overnight. After consumption of the starting material, it was diluted by water (50 mL), evaporated to remove MeOH and THF, and acidified by aqueous HCl with stirring to give a precipitate. The precipitate was collected by suction, washed by water and dried to give carboxylic acid 451-2 (1.50 g, 87% yield) as a black solid. LC/MS (ESI): m/z=278.0 $[M+1]^+$. RT=1.107 min.

Step-3 (ii): To a solution of thiazole 451-3 (320 mg, 1.0 mmol) in THF (5 mL), MeOH (5 mL) and $H_2O$ (5 mL) was added $LiOH{\cdot}H_2O$ (630 mg, 15.0 mmol), and the reaction mixture was stirred at room temperature overnight. After consumption of the starting material, it was diluted by water (20 mL), evaporated to remove MeOH and THE, and acidified by aqueous HCl with stirring to give a precipitate. The precipitate was collected by suction, washed by water and dried to give carboxylic acid 451-2 (260 mg, 90% yield) as a black solid. LC/MS (ESI): m/z=292.0 $[M+1]^+$. RT=1.132 min.

General Scheme 4 was used to prepare the following compounds, with the functional groups as specified:

451-6 as Compound 2—Step-2 (i) R=H; Step-3 (i); Step-4 $R^1$&$R^2$=—$CH_2CH(CH_3)CH_2CH(CH_3)CH_2$— To a solution of carboxylic acid 451-4 (200 mg, 0.72 mmol) and 3,5-dimethylpiperidine 451-5 (163 mg, 1.44 mmol) in DMF (20 mL) was added EDCI·HCl (207 mg, 1.08 mmol), HOBT (146 mg, 1.08 mmol) and $Et_3N$ (218 mg, 2.16 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give 451-6 as Compound 2 (32 mg, 12% yield) as a white solid. $^1H$ NMR (400 MHz, DMSO-$d_6$) δ 10.68 (s, 1H), 9.21 (s, 1H), 8.66 (d, J=2.0 Hz, 1H), 8.01 (d, J=8.8 Hz, 1H), 7.54 (dd, J=8.8, 2.0 Hz, 1H), 7.37 (s, 1H), 4.45 (d, J=11.6 Hz, 1H), 2.57-2.49 (m, 1H), 2.22 (t, J=12.0 Hz, 1H), 1.88-1.80 (m, 2H), 1.63-1.60 (m, 1H), 0.93-0.82 (m, 7H). LC/MS (ESI): m/z=372.9 $[M+1]^+$. RT=8.673 min.

451-6 as Compound 3—Step-2 (ii) R=$CH_3$; Step-3 (ii); Step-4 $R^1$&$R^2$=—$CH_2CH(CH_3)CH_2CH(CH_3)CH_2$— To a solution of carboxylic acid 451-4 (130 mg, 0.45 mmol) and 3,5-dimethylpiperidine 451-5 (100 mg, 0.89 mmol) in DMF (15 mL) was added EDCI·HCl (170 mg, 0.89 mmol), HOBT (120 mg, 0.89 mmol) and $Et_3N$ (0.37 mL, 2.68 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give 451-6 as Compound 3 (24 mg, 14% yield) as a white solid. $^1H$ NMR (400 MHz, DMSO-$d_6$) δ 10.48 (s, 1H), 9.19 (s, 1H), 8.62 (d, J=2.0 Hz, 1H), 7.99 (d, J=8.8 Hz, 1H), 7.50 (dd, J=8.8, 2.0 Hz, 1H), 4.46 (d, J=10.4 Hz, 1H), 3.92 (d, J=12.4 Hz, 1H), 2.55-2.49 (m, 1H), 2.32 (s, 3H), 2.21 (t, J=12.0 Hz, 1H), 1.85 (d, J=12.8 Hz, 1H), 1.77-1.74 (m, 1H), 1.63-1.60 (m, 1H), 0.94-0.79 (m, 7H). LC/MS (ESI): m/z=386.9 $[M+1]^+$. RT=8.945 min.

451-6 as Compound 4—Step-2 (i) R=H; Step-3 (i); Step-4 $R^1$&$R^2$=—$(CH_2)_3CH((S)CH_3)CH_2$— To a solution of carboxylic acid 451-4 (200 mg, 0.72 mmol) and(S)-3-methylpiperidine 451-5 (143 mg, 1.44 mmol) in DMF (20 mL) was added EDCI·HCl (207 mg, 1.08 mmol), HOBt (146 mg, 1.08 mmol) and $Et_3N$ (218 mg, 2.16 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give 451-6 as Compound 4 (40 mg, 15.5% yield) as a white solid. $^1H$ NMR (400 MHz, DMSO-$d_6$) δ 10.68 (s, 1H), 9.21 (s, 1H), 8.67 (d, J=1.6 Hz, 1H), 8.01 (d, J=8.8 Hz, 1H), 7.54 (dd, J=8.8, 1.6 Hz, 1H), 7.35 (s, 1H), 4.32 (s, 2H), 3.08-3.06 (m, 0.5H), 2.73-2.68 (m, 1H), 2.51-2.48 (m, 0.5H), 1.86-1.47 (m, 4H), 1.26-1.17 (m, 1H), 0.92-0.86 (m, 3H). LC/MS (ESI): m/z=358.9 $[M+1]^+$. RT=8.059 min. 451-6 as Compound 5—Step-2 (ii) R=$CH_3$; Step-3 (ii); Step-4 $R^1$&$R^2$=—$(CH_2)_3CH((S) CH_3)CH_2$— To a solution of carboxylic acid 451-4 (130 mg, 0.45 mmol) and(S)-3-methylpiperidine hydrochloride 451-5 (120 mg, 0.89 mmol) in DMF (15 mL) was added EDCI·HCl (170 mg, 0.89 mmol), HOBT (120 mg, 0.89 mmol) and $Et_3N$ (0.37 mL, 2.68 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give 451-6 as Compound 5 (64 mg, 38.5% yield) as a white solid. $^1H$ NMR (400 MHz, DMSO-$d_6$) δ 9.19 (s, 1H), 8.62 (d, J=2.8 Hz, 1H), 7.99 (d, J=8.8 Hz, 1H), 7.50 (dd, J=8.8, 2.4 Hz, 1H), 4.36-4.26 (m, 1H), 3.84 (t, J=12.8 Hz, 1H), 3.02 (t, J=10.4 Hz, 0.5H), 2.78-2.65 (m, 1H), 2.55-2.50 (m, 0.5H), 2.32 (s, 3H), 1.85-1.81 (m, 1H), 1.75-1.45 (m, 3H), 1.25-1.15 (m, 1H), 0.94-0.80 (m, 3H). LC/MS (ESI): m/z=373.0 $[M+1]^+$. RT=8.312 min.

451-6 as Compound 6—Step-2 (i) R=H; Step-3 (i); Step-4 $R^1$&$R^2$=—$CH_2CH(CH_3)$ $OCH(CH_3)CH_2$— To a mixture of carboxylic acid 451-4 (200 mg, 0.72 mmol) and 2,6-dimethylmorpholine 451-5 (92 mg, 0.80 mmol) in DMF (20 mL) was added HOBt (146 mg, 1.08 mmol), EDCI·HCl (207 mg, 1.08 mmol) and $Et_3N$ (218 mg, 2.16 mmol), the reaction mixture was stirred at room temperature overnight. After consumption of the starting material, water (30 mL) was added and the mixture was extracted with EtOAc (2×30 mL). The combined organic layers were washed with water (4×50 mL) and brine (50 mL) successively, dried over anhydrous $Na_2SO_4$ and concentrated under reduced pressure to give a residue. The residue was purified by reversed phase prep-HPLC to give 451-6 as Compound 6 (28 mg, 10.4% yield) as a white solid. $^1H$ NMR (400 MHz, DMSO-$d_6$) δ 10.70 (s, 1H), 9.22 (s, 1H), 8.63 (d, J=2.0 Hz, 1H), 8.02 (d, J=8.8 Hz, 1H), 7.53 (dd, J=8.8, 2.0 Hz, 1H), 7.46 (s, 1H), 4.57 (d, J=11.6 Hz, 1H), 4.35 (d, J=12.0 Hz, 1H), 3.70-3.61 (m, 2H), 2.86-2.80 (m, 1H), 2.50-2.45 (m, 1H), 1.16-1.10 (m, 6H). LC/MS (ESI): m/z=375.0 $[M+1]^+$. RT=7.158 min.

451-6 as Compound 7—Step-2 (i) R=H; Step-3 (i); Step-4 $R^1$&$R^2$=—$(CH_2)_5$— To a solution of carboxylic acid 451-4 (200 mg, 0.72 mmol) and piperidine 451-5 (123 mg, 1.44 mmol) in DMF (20 mL) was added EDCI·HCl (207 mg, 1.08 mmol), HOBt (146 mg, 1.08 mmol) and $Et_3N$ (218 mg, 2.16 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give 541-5 as Compound 7 (55 mg, 22% yield) as a white solid. $^1H$ NMR (400 MHz, DMSO-$d_6$) δ 10.64 (s, 1H), 9.21 (s, 1H), 8.67 (d, J=2.0 Hz, 1H), 8.02 (d, J=8.8 Hz, 1H), 7.54 (dd, J=8.8, 2.4

Hz, 1H), 7.34 (s, 1H), 3.72 (s, 2H), 3.59 (s, 2H), 1.67-1.60 (m, 6H). LC/MS (ESI): m/z=344.9 $[M+1]^+$. RT=7.481 min.

451-6 as Compound 9—Step-2 (i) R=H; Step-3 (i); Step-4 $R^1$&$R^2$=—$(CH_2)_7$— To a solution of carboxylic acid 451-4 (150 mg, 0.54 mmol) and azocane 451-5 (72 mg, 0.59 mmol) in DMF (20 mL) was added EDCI·HCl (156 mg, 0.81 mmol), HOBt (110 mg, 0.81 mmol) and $Et_3N$ (164 mg, 1.62 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give 451-6 as Compound 9 (30 mg, 15% yield) as a white solid. $^1$H NMR (400 MHz, DMSO-$d_6$) δ 10.65 (s, 1H), 9.20 (s, 1H), 8.72 (d, J=2.0 Hz, 1H), 8.01 (d, J=8.8 Hz, 1H), 7.49 (dd, J=8.8, 2.0 Hz, 1H), 7.29 (s, 1H), 3.64 (t, J=6.4 Hz, 2H), 3.54 (t, J=6.0 Hz, 2H), 1.73-1.56 (m, 10H). LC/MS (ESI): m/z=373.0 $[M+1]^+$. RT=8.413 min.

451-6 as Compound 11—Step-2 (ii) R=$CH_3$; Step-3 (ii); Step-4 $R^1$&$R^2$=—$(CH_2)_3CH((R)CH_3)CH_2$— To a solution of carboxylic acid 451-4 (130 mg, 0.45 mmol) and (R)-3-methylpiperidine hydrochloride 451-5 (100 mg, 0.89 mmol) in DMF (15 mL) was added EDCI·HCl (170 mg, 0.89 mmol), HOBT (120 mg, 0.89 mmol) and $Et_3N$ (0.37 mL, 2.68 mmol), and the reaction mixture was allowed to stir at room temperature overnight. After consumption of the starting material, the reaction mixture was diluted by water (30 mL) and extracted with EtOAc (2×20 mL). The organic extract was washed by water (4×30 mL) and brine (30 mL) successively, dried over anhydrous $Na_2SO_4$, filtered and evaporated under reduced pressure to give a residue. The residue was purified by reversed phase Prep-HPLC to give (24 mg, 14.5% yield) as a white solid. $^1$H NMR (400 MHz, DMSO-$d_6$) δ10.46 (d, J=3.6 Hz, 1H), 9.19 (s, 1H), 8.61 (d, J=2.4 Hz, 1H), 7.99 (d, J=8.8 Hz, 1H), 7.50 (dd, J=8.8, 2.0 Hz, 1H), 4.36-4.25 (m, 1H), 3.88-3.81 (m, 1H), 3.05-2.99 (m, 0.5H), 2.79-2.65 (m, 1H), 2.55-2.50 (m, 0.5H), 2.32 (s, 3H), 1.85-1.80 (m, 1H), 1.75-1.40 (m, 3H), 1.25-1.15 (m, 1H), 0.95-0.80 (m, 3H). LC/MS (ESI): m/z=373.3 $[M+1]^+$. RT=8.384 min.

451-6 as Compound 12—Step-2 (i) R=H; Step-3 (i); Step-4 $R^1$&$R^2$=—$CH(CH_3)$ $(CH_2)_3CH(CH_3)$— To a solution of carboxylic acid 451-4 (140 mg, 0.50 mmol) and 2,6-dimethylpiperidine 451-5 (60 mg, 0.53 mmol) in DMF (10 mL) was added EDCI·HCl (191 mg, 1.0 mmol), HOBt (135 mg, 1.0 mmol) and triethylamine (202 mg, 2.0 mmol). The mixture was stirred at room temperature overnight. The reaction mixture was diluted with water (50 mL) and then extracted with EtOAc (2×50 mL). The organic phase was separated and concentrated in vacuo to a residue. The residue was purified by reversed phase pre-HPLC to give 451-6 as Compound 12 (20 mg, 10.6% yield) as a white solid. $^1$H NMR (400 MHz, DMSO-$d_6$): δ 10.64 (s, 1H), 9.21 (s, 1H), 8.66 (d, J=2.0 Hz, 1H), 8.01 (d, J=8.8 Hz, 1H), 7.53 (dd, J=8.8, 2.4 Hz, 1H), 7.27 (s, 1H), 4.66 (s, 2H), 1.89-1.83 (m, 1H), 1.68-1.59 (m, 4H), 1.51-1.46 (m, 1H), 1.30 (s, 3H), 1.28 (s, 3H). LC/MS (ESI): m/z=373.2 $[M+1]^+$. RT=8.363 min.

General Scheme 5: Experimental Procedure for the Synthesis of Compounds 1, 13, 14, 15, 16, 19, 21, 22, 23, 24, 26, 27

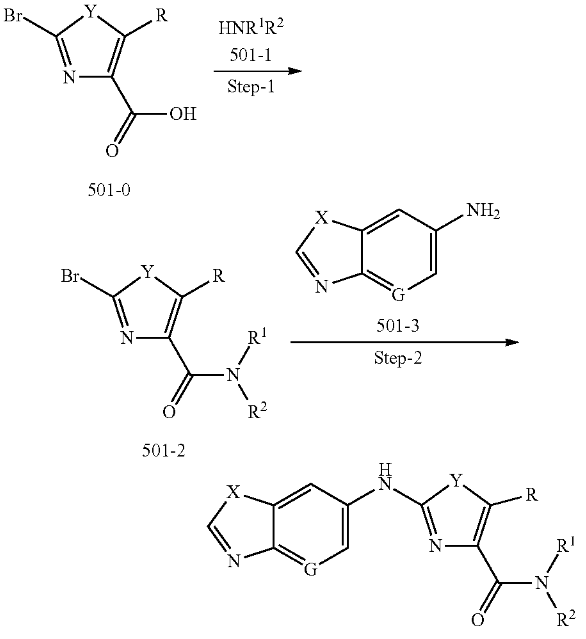

501-0

501-2

501-3

501-4

Y=O or S; X=O or S; G=CH or N or CF, R=H or $CH_3$; $R^1$&$R^2$=—$CH_2CH(CH_3)CH_2CH(CH_3)CH_2$— or —$CH_2CH(CH_3)$ $OCH(CH_3)CH_2$— or —$(CH_2)_3CH$ $(CH_3)$ C $H(CH_3)$— or —$(CH_2)_3CH(CF_3)CH_2$— or —$(CH_2)_6$— or —$(CH_2)_7$— or —$(CH_2)_4CH((R)$ $CH_3)$—

General Scheme 5 was used to prepare the following compounds, with the functional groups as specified:

Compound 1—Y=S, X=O, G=CH, R=H, $R^1$&$R^2$=—$CH_2CH(CH_3)CH_2CH(CH_3)CH_2$—

Step-1: To a solution of carboxylic acid 501-0 (700 mg, 3.36 mmol) and amine 501-1 (452 mg, 4.0 mmol) in DMF (20 mL) was added EDCI·HCl (955 mg, 5.0 mmol), HOBt (675 mg, 5.0 mmol) and DIEA (905 mg, 7.0 mmol). The reaction mixture was stirred at room temperature overnight. After the raw materials are consumed, the reaction mixture was diluted by water (100 mL) and extracted with EtOAc (2×100 mL). The organic phase was concentrated in vacuo to give a residue. The residue was purified by column chromatography on silica gel (eluting with 20% EtOAc in PE) to give amide 501-2 (700 mg, 68.6% yield) as a pale-yellow oil.

Step-2: To a solution of amide 501-2 (700 mg, 2.31 mmol) in 1,4-dioxane (50 mL) was added arylamine 501-3 (402 mg, 3.0 mmol), $Cs_2CO_3$ (1.3 g, 4.0 mmol), Brettphos-Pd-$G_3$ (272 mg, 0.30 mmol) and Xphos (141 mg, 0.30 mmol). The mixture was heated to 100° C. and stirred overnight under argon atmosphere. The solvent was evaporated in vacuo to a residue. The residue was purified by chromatography in silica gel (eluting with EtOAc) to give crude product. The crude product was further purified by Prep-HPLC to give 501-4 as Compound 1 (150 mg, 18% yield) as an off-white solid. $^1$H NMR (400 MHz, DMSO-$d_6$) δ 10.65 (br, 1H), 8.62 (s, 1H), 8.40 (d, J=1.6 Hz, 1H), 7.72 (d, J=8.8 Hz, 1H), 7.36-7.33 (m, 2H), 4.46 (m, 2H), 2.54-2.50 (m, 1H), 2.23-2.08 (m, 1H), 1.87-1.60 (m, 3H), 0.89-0.80 (m, 7H). LC/MS (ESI): m/z=357.2 $[M+1]^+$. RT=8.756 min.

Compound 13—Y=S, X=O, G=CH, R=H, $R^1$&$R^2$=—$CH_2CH(CH_3)OCH(CH_3)CH_2$—

Step-1: To a solution of carboxylic acid 501-0 (416 mg, 2.0 mmol) and amine 501-1 (920 mg, 8.0 mmol) in DMF (10 mL) was added EDCI·HCl (768 mg, 4.0 mmol), HOBT (540 mg, 4.0 mmol) and $Et_3N$ (808 mg, 8.0 mmol), and the reaction mixture was allowed to stir at room temperature overnight. After consumption of the starting material, the reaction mixture was diluted by water (30 mL) and extracted with EtOAc (2×30 mL). The organic extract was washed by water (4×50 mL) and brine (50 mL) successively, dried over anhydrous $Na_2SO_4$, filtered and evaporated under reduced pressure to give a residue. The residue was purified by column chromatography on silica gel (eluting with 2% MeOH in $CH_2Cl_2$) to give amide 501-2 (300 mg, 49% yield) as a yellow solid. LC/MS (ESI): m/z=305.0 $[M+1]^+$. RT=1.538 min.

Step-2: To a mixture of amide 501-2 (200 mg, 0.66 mmol), arylamine 501-3 (177 mg, 1.32 mmol), $Cs_2CO_3$ (858 mg, 2.64 mmol) in 1,4-dioxane (5 mL) was added $Pd_2(dba)_3$ (64 mg, 0.07 mmol), Xantphos (81 mg, 0.14 mmol), and the reaction mixture was purged with argon and stirred at 100° C. for 1 hour under microwave irradiation. After cooling to room temperature, it was diluted by water (20 mL) and extracted with EtOAc (2×20 mL). The organic extract was washed by brine (20 mL), dried over anhydrous $Na_2SO_4$, filtered, evaporated under reduced pressure and purified by reversed phase prep-HPLC to give 501-4 as Compound 13 (9.31 mg, 4% yield) as a white solid. $^1H$ NMR (400 MHz, $CD_3OD$) δ 8.39 (d, J=1.6 Hz, 1H), 8.38 (s, 1H), 7.65 (d, J=8.8 Hz, 1H), 7.38 (s, 1H), 7.32 (dd, J=8.4, 2.0 Hz, 1H), 4.72 (d, J=12.4 Hz, 1H), 4.46 (dd, J=12.4, 2.8 Hz, 1H), 3.81-3.70 (m, 2H), 2.89 (t, J=11.2 Hz, 1H), 2.58 (t, J=11.2 Hz, 1H), 1.28-1.19 (m, 6H). LC/MS (ESI): m/z=359.2 $[M+1]^+$. RT=7.241 min.

Compound 14—Y=S, X=S, G=CH, R=$CH_3$, $R^1$&$R^2$=—$CH_2CH(CH_3)$ $OCH(CH_3)CH_2$—

Step-1: To a solution of carboxylic acid 501-0 (222 mg, 1.0 mmol) and amine 501-1 (143 mg, 1.20 mmol) in DMF (15 mL) was added EDCI·HCl (287 mg, 1.50 mmol), HOBt (202 mg, 1.50 mmol) and $Et_3N$ (303 mg, 3.0 mmol), and the reaction mixture was allowed to stir at room temperature overnight. After all the raw materials were consumed, the reaction mixture was diluted by water (30 mL) and extracted with EtOAc (3×20 mL). The organic extract was washed by water (4×30 mL) and brine (30 mL) successively, dried over anhydrous $Na_2SO_4$, filtered and evaporated under reduced pressure and purified by column chromatography on silica gel (eluting with 0%~55% EtOAc in PE) to give amide 570-2 (212 mg, 66.5% yield) as a colorless oil. LC/MS (ESI): m/z=319.2 $[M+H]^+$. RT=0.615 min Step-2: A suspension of amide 570-2 (200 mg, 0.57 mmol), arylamine 501-3 (112 mg, 0.57 mmol), $Cs_2CO_3$ (557 mg, 1.71 mmol), $Pd_2(dba)_3$ (101 mg, 0.11 mmol) and Xantphos (133 mg, 0.23 mmol) in dioxane (5 mL) was stirred at 100° C. overnight under nitrogen atmosphere. After all the raw materials were consumed, the reaction mixture was filtered through a celite pad to remove the solid and the filtrate was evaporated under reduced pressure to give crude, which was purified by reversed phase prep-HPLC to give 501-4 as Compound 14 (42 mg, 23.4% yield) as a white solid. $^1H$ NMR (400 MHz, $CD_3OD$) δ 9.06 (s, 1H), 8.64 (d, J=2.4 Hz, 1H), 7.95 (d, J=8.8 Hz, 1H), 7.46 (dd, J=8.8, 2.4 Hz, 1H), 4.48 (d, J=13.2 Hz, 1H), 4.05 (d, J=13.6 Hz, 1H), 3.79-3.68 (m, 2H), 2.85 (dd, J=13.2, 10.8 Hz, 1H), 2.58 (dd, J=13.2, 10.8 Hz, 1H), 2.40 (s, 3H), 1.25 (d, J=6.0 Hz, 3H), 1.11 (d, J=6.4 Hz, 3H). LC/MS (ESI): m/z=389.1 $[M+1]^+$. RT=6.77 min.

Compound 15—Y=S, X=O, G=CH, R=$CH_3$, $R^1$&$R^2$=—$CH_2CH(CH_3)$ $OCH(CH_3)CH_2$—

Step-1 (i): see Step 1 of Compound 14 for details.

Step-2: A suspension of amide 501-2 (181 mg, 0.57 mmol), arylamine 501-3 (76 mg, 0.57 mmol), $Cs_2CO_3$ (557 mg, 1.71 mmol), $Pd_2(dba)_3$ (101 mg, 0.11 mmol) and Xantphos (127 mg, 0.22 mmol) in dioxane (5 mL) was stirred at 100° C. overnight under nitrogen atmosphere. After all the raw materials were consumed, the reaction mixture was filtered through a celite pad to remove the solid and the filtrate was evaporated under reduced pressure to give crude, which was purified by reversed phase prep-HPLC to give 501-4 as Compound 15 (64 mg, 30.7% yield) as a white solid. $^1H$ NMR (400 MHz, $CD_3OD$) δ 8.37 (s, 1H), 8.36 (d, J=2.4 Hz, 1H), 7.62 (d, J=8.4 Hz, 1H), 7.28 (dd, J=8.4, 2 Hz, 1H), 4.48 (d, J=13.2 Hz, 1H), 4.05 (d, J=13.2 Hz, 1H), 3.80-3.67 (m, 2H), 2.85 (dd, J=13.2, 10.8 Hz, 1H), 2.58 (dd, J=13.2, 10.8 Hz, 1H), 2.40 (s, 3H), 1.25 (d, J=6.0 Hz, 3H), 1.12 (d, J=6.0 Hz, 3H). LC/MS (ESI): m/z=373.2 $[M+1]^+$. RT=7.08 min.

Compound 16—Y=S, X=O, G=CH, R=H, $R^1$&$R^2$=—$(CH_2)_3CH(CH_3)CH(CH_3)$—

Step-1 (ii) To a solution of carboxylic acid 501-0 (1.0 g, 4.80 mmol) and amine 501-1 (600 mg, 5.30 mmol) in DMF (20 mL) was added EDCI·HCl (1.38 g, 7.2 mmol), HOBt (972 mg, 7.20 mmol) and DIEA (1.24 g, 9.60 mmol). The mixture was stirred at room temperature overnight. The reaction mixture was diluted with water (100 mL) and then extracted with EtOAc (100 mL). The organic phase was separated and concentrated in vacuo to a residue. The residue was purified by column chromatography in silica gel (eluting with 20% EtOAc in PE) to give amide 501-2 (1.0 g, 33.3% yield) as a yellow oil. LC/MS (ESI): m/z=303.2 $[M+1]^+$. RT=2.041 min.

Step-2: To a solution of amide 501-2 (180 mg, 0.59 mmol) in 1,4-dioxane (20 mL) was added arylamine 501-3 (95 mg, 0.71 mmol), Xphos (94 mg, 0.20 mmol), Brettphos-Pd-$G_3$ (91 mg, 0.10 mmol) and $Cs_2CO_3$ (325 mg, 1.0 mmol). The mixture was heated to 100° C. and stirred overnight under argon atmosphere. The solvent was evaporated in vacuo to a residue. The residue was purified by column chromatography on silica gel (eluting with EtOAc) and then further purified by reversed phase Prep-HPLC to give 501-4 as Compound 16 (100 mg, 47% yield) as an off-white solid. $^1H$ NMR (400 MHz, DMSO-$d_6$) δ 10.64 (s, 1H), 8.61 (s, 1H), 8.42 (s, 1H), 7.71 (d, J=8.8 Hz, 1H), 7.33 (dd, J=8.8, 2.0 Hz, 1H), 7.28 (s, 1H), 4.58 (s, 1H), 4.31-4.22 (m, 2H), 3.04-2.80 (m, 1H), 1.87-1.64 (m, 2H), 1.56-1.31 (m, 3H), 1.15-1.09 (m, 3H), 0.99-0.82 (m, 3H). LC/MS (ESI): m/z=357.2 $[M+1]^+$. RT=8.482 min.

Compound 19—Y=S, X=O, G=CH, R=H, $R^1$&$R^2$=—$(CH_2)_3CH(CF_3)CH_2$—

Step-1: To a solution of carboxylic acid 501-0 (250 mg, 1.20 mmol) and amine 501-1 (440 mg, 2.30 mmol) in DMF (15 mL) was added EDCI·HCl (316 mg, 1.65 mmol), HOBt (223 mg, 1.65 mmol) and DIEA (0.77 mL, 4.6 mmol). The reaction mixture was stirred at room temperature overnight. After the raw materials are consumed, the reaction mixture was diluted by water (50 mL) and extracted with EtOAc (2×50 mL). The organic extract was washed by water (4×50 mL) and brine (50 mL) successively, dried over anhydrous $Na_2SO_4$, filtered and evaporated under reduced pressure to a residue. The residue was purified by column chromatography on silica gel (eluting with 20% EtOAc in PE) to give amide 501-2 (380 mg, 92% yield) as a colorless oil. LC/MS (ESI): m/z=343.0 $[M+H]^+$. RT=2.037 min.

Step-2: A mixture of amide 501-2 (380 mg, 1.11 mmol), arylamine 501-3 (223 mg, 1.67 mmol), $Cs_2CO_3$ (721 mg, 2.22 mmol), Brettphos-Pd-$G_3$ (99.8 mg, 0.11 mmol) and Xphos (52.4 mg, 0.11 mmol) in 1,4-dioxane (25 mL) was heated at 100° C. and stirred overnight under argon atmosphere overnight. After the raw materials are consumed, the reaction mixture was filtered through a celite pad to remove the solid and the filtrate was evaporated under reduced pressure and purified by reversed phase pre-HPLC to give 501-4 as Compound 19 (70 mg, 15.9% yield) as an off-white solid. $^1H$ NMR (400 MHz, DMSO-$d_6$) δ 10.69 (s, 1H), 8.63 (s, 1H), 8.38 (s, 1H), 7.71 (d, J=8.4 Hz, 1H), 7.42 (s, 1H), 7.34 (dd, J=8.4, 2.0 Hz, 1H), 4.67-4.53 (m, 1H), 4.39 (d, J=12.8 Hz, 1H), 3.22 (s, 1H), 2.98-2.84 (m, 1H), 2.64-2.62 (m, 1H), 2.04-2.02 (m, 1H), 1.84-1.81 (m, 1H), 1.66-1.62 (m, 2H). LC/MS (ESI): m/z=397.0 $[M+1]^+$. RT=1.758 min.

Compound 21—Y=S, X=O, G=CH, R=H, $R^1$&$R^2$=—$(CH_2)_6$—

Step-1: To a solution of carboxylic acid 501-0 (416 mg, 2.0 mmol) and amine 501-1 (0.45 mL, 4.0 mmol) in DMF (20 mL) was added EDCI·HCl (575 mg, 3.0 mmol), HOBt (405 mg, 3.0 mmol) and DIEA (1.31 mL, 8.0 mmol), and the reaction mixture was allowed to stir at room temperature overnight. After the raw materials are consumed, the reaction mixture was diluted by water (80 mL) and extracted with EtOAc (3×30 mL). The organic extract was washed by water (4×50 mL) and brine (50 mL) successively, dried over anhydrous $Na_2SO_4$, filtered, evaporated under reduced pressure and purified by column chromatography on silica gel (eluting with 0%~30% EtOAc in PE) to give amide 501-2 (366 mg, 63.3% yield) as a white solid. LC/MS (ESI): m/z=288.8 $[M+H]^+$. RT=1.928 min.

Step-2: A mixture of amide 501-2 (366 mg, 1.27 mmol), arylamine 501-3 (256 mg, 1.91 mmol), $Cs_2CO_3$ (826 mg, 2.54 mmol), Pd-$G_3$ (115 mg, 0.18 mmol) and X-phos (61 mg, 0.18 mmol) in dioxane (30 mL) was stirred at 100° C. overnight under argon atmosphere. After the raw materials are consumed, the reaction mixture was filtered through a celite pad to remove the solid and the filtrate was evaporated under reduced pressure and purified by reversed phase prep-HPLC to give 501-4 as Compound 21 (80 mg, 18.5% yield) as an off white solid. $^1H$ NMR (400 MHz, DMSO-$d_6$) δ 10.65 (s, 1H), 8.62 (s, 1H), 8.39 (d, J=2.0 Hz, 1H), 7.72 (d, J=8.8 Hz, 1H), 7.35-7.33 (m, 2H), 3.73 (t, J=6.0 Hz, 2H), 3.56 (t, J=6.0 Hz, 2H), 1.76-1.72 (m, 4H), 1.59 (d, J=2.8 Hz, 4H). LC/MS (ESI): m/z=343.2 $[M+1]^+$. RT=8.466 min.

Compound 22—Y=S, X=O, G=CH, R=H, $R^1$&$R^2$=—$(CH_2)_7$—

Step-1: To a solution of carboxylic acid 501-0 (416 mg, 2.0 mmol) and amine 501-1 (0.48 mL, 4.0 mmol) in DMF (20 mL) was added EDCI·HCl (575 mg, 3.0 mmol), HOBt (405 mg, 3.0 mmol) and DIEA (1.31 mL, 8.0 mmol), and the reaction mixture was allowed to stir at room temperature overnight. After the raw materials are consumed, the reaction mixture was diluted by water (80 mL) and extracted with EtOAc (3×40 mL). The organic extract was washed by water (4×50 mL) and brine (50 mL) successively, dried over anhydrous $Na_2SO_4$, filtered, evaporated under reduced pressure and purified by column chromatography on silica gel (eluting with 0%~30% EtOAc in PE) to give amide 501-2 (440 mg, 72.6% yield) as a white solid. LC/MS (ESI): m/z=303.0 $[M+H]^+$. RT=1.902 min.

Step-2: A mixture of amide 501-2 (440 mg, 1.45 mmol), arylamine 501-3 (294 mg, 2.19 mmol), $Cs_2CO_3$ (949 mg, 2.92 mmol), Pd-$G_3$ (132 mg, 0.15 mmol) and X-phos (70 mg, 0.15 mmol) in 1,4-dioxane (30 mL) was stirred at 100° C. overnight under argon atmosphere. After the raw materials are consumed, the reaction mixture was filtered through a celite pad to remove the solid and the filtrate was evaporated under reduced pressure and purified by reversed phase prep-HPLC to give 501-4 as Compound 22 (100 mg, 19.3% yield) as a yellow solid. $^1H$ NMR (400 MHz, DMSO-$d_6$) δ 10.65 (s, 1H), 8.62 (s, 1H), 8.41 (d, J=1.6 Hz, 1H), 7.71 (d, J=8.4 Hz, 1H), 7.34-7.29 (m, 2H), 3.66 (t, J=5.2 Hz, 2H), 3.54 (t, J=6.0 Hz, 2H), 1.72-1.57 (m, 10H). LC/MS (ESI): m/z=357.0 $[M+1]^+$. RT=1.763 min.

Compound 23—Y=S, X=O, G=CH, R=H, $R^1$&$R^2$=—$(CH_2)_4CH((R)CH_3)$—

Step-1: To a solution of carboxylic acid 501-0 (416 mg, 2.0 mmol) and amine 501-1 (0.49 mL, 4.0 mmol) in DMF (15 mL) was added EDCI (575 mg, 3.0 mmol), HOBt (405 mg, 3.0 mmol) and DIEA (1.31 mL, 8.0 mmol), and the reaction mixture was allowed to stir at room temperature overnight. After the raw materials are consumed, the reaction mixture was diluted by water (80 mL) and extracted with EtOAc (3×20 mL). The organic extract was washed by water (4×20 mL) and brine (20 mL) successively, dried over anhydrous $Na_2SO_4$, filtered, evaporated under reduced pressure and purified by column chromatography on silica gel (eluting with 0%~30% EA in PE) to give amide 501-2 (410 mg, 71% yield) as a white solid. LC/MS (ESI): m/z=289 $[M+H]^+$. RT=1.906 min.

Step-2: A suspension of amide 501-2 (410 mg, 1.42 mmol), arylamine 501-3 (286 mg, 2.13 mmol), $Cs_2CO_3$ (923 mg, 2.84 mmol), Brettphos-Pd-$G_3$ (129 mg, 0.14 mmol) and Xphos (68 mg, 0.14 mmol) in 1,4-dioxane (30 mL) was heated at 100° C. and stirred overnight under nitrogen atmosphere overnight. After the raw materials are consumed, the reaction mixture was filtered through a celite pad to remove the solid and the filtrate was evaporated under reduced pressure and purified by reversed phase Prep-HPLC to give 501-4 as Compound 23 (50 mg, 10.3% yield) as an off-white solid. $^1H$ NMR (400 MHz, DMSO-$d_6$) δ 10.66 (s, 1H), 8.62 (s, 1H), 8.43 (d, J=1.6 Hz, 1H), 7.71 (d, J=8.4 Hz, 1H), 7.34-7.30 (m, 2H), 4.63-4.67 (m, 1H), 4.27 (d, J=10.8 Hz, 1H), 3.04-2.95 (m, 1H), 1.75-1.54 (m, 5H), 1.46-1.38 (m, 1H), 1.28-1.19 (m, 3H). LC/MS (ESI): m/z=343.3 $[M+1]^+$. RT=1.807 min.

Compound 24—Y=S, X=O, G=CH, R=$CH_3$, $R^1$&$R^2$=—$CH_2CH(CH_3)CH_2CH(CH_3)CH_2$—

Step-1: To a solution of carboxylic acid 501-0 (444 mg, 2.0 mmol) and amine 501-1 (0.53 mL, 4.0 mmol) in DMF (15 mL) was added EDCI (575 mg, 3.0 mmol), HOBt (405 mg, 3.0 mmol) and DIEA (1.31 mL, 8.0 mmol), and the reaction mixture was allowed to stir at room temperature overnight. After the raw materials are consumed, the reaction mixture was diluted by water (80 mL) and extracted with EtOAc (3×20 mL). The organic extract was washed by water (4×20 mL) and brine (20 mL) successively, dried over anhydrous $Na_2SO_4$, filtered and evaporated under reduced pressure and purified by column chromatography on silica gel (eluting with 0%~30% EA in PE) to give amide 501-2 (593 mg, 94% yield) as a yellow oil liquid. LC/MS (ESI): m/z=317.0 $[M+H]^+$. RT=1.986 min.

Step-2: A suspension of amide 501-2 (593 mg, 1.87 mmol), arylamine 501-3 (377 mg, 2.81 mmol), $Cs_2CO_3$ (1.83 g, 5.63 mmol), Brettphos-Pd-$G_3$ (172 mg, 0.19 mmol) and Xphos (90 mg, 0.19 mmol) in 1,4-dioxane (30 mL) was heated at 100° C. and stirred overnight under nitrogen atmosphere overnight. After the raw materials are consumed, the reaction mixture was filtered through a celite pad to remove the solid and the filtrate was evaporated under reduced pressure and purified by reversed phase Prep-HPLC to give 501-4 as Compound 24 (80 mg, 11.6% yield) as a white solid. $^1$H NMR (400 MHz, DMSO-$d_6$) δ 10.47 (s, 1H), 8.60 (s, 1H), 8.35 (d, J=2.0 Hz, 1H), 7.69 (d, J=8.8 Hz, 1H), 7.30 (dd, J=8.8, 2.0 Hz, 1H), 4.46 (d, J=11.2 Hz, 1H), 3.90 (d, J=12.4 Hz, 1H), 2.53 (d, J=12.0 Hz, 1H), 2.32 (s, 3H), 2.22 (t, J=12.0 Hz, 1H), 1.84 (d, J=13.2 Hz, 1H), 1.76-1.74 (m, 1H), 1.61-1.58 (m, 1H), 0.92 (d, J=6.8 Hz, 3H), 0.89-0.83 (m, 1H), 0.79 (d, J=6.4 Hz, 3H). LC/MS (ESI): m/z=371.0 $[M+1]^+$. RT=9.170 min.

Compound 26—Y=S, X=O, G=N, R=H, $R^1$&$R^2$=—$CH_2CH(CH_3)CH_2CH(CH_3)CH_2$—

Step-1: To a solution of carboxylic acid 501-0 (416 mg, 2.0 mmol) and amine 501-1 (453 mg, 4.0 mmol) in DMF (15 mL) was added EDCI·HCl (575 mg, 3.0 mmol), HOBt (405 mg, 3.0 mmol) and DIEA (1.31 mL, 8.0 mmol), and the reaction mixture was allowed to stir at room temperature overnight. After the raw materials are consumed, the reaction mixture was diluted by water (50 mL) and extracted with EtOAc (3×30 mL). The organic extract was washed by water (4×50 mL) and brine (50 mL) successively, dried over anhydrous $Na_2SO_4$, filtered, evaporated under reduced pressure and purified by column chromatography on silica gel (eluting with 0%~30% EtOAc in PE) to give amide 501-2 (400 mg, 66% yield) as a white solid. LC/MS (ESI): m/z=303.0 $[M+H]^+$. RT=1.935 min.

Step-2: A suspension of amide 501-2 (100 mg, 0.33 mmol), arylamine 501-3 (67 mg, 0.50 mmol), $Cs_2CO_3$ (215 mg, 0.66 mmol), $Pd_2(dba)_3$ (30 mg, 0.033 mmol) and Xantphos (19 mg, 0.033 mmol) in 1,4-dioxane (15 mL) was stirred at 100° C. overnight under nitrogen atmosphere. After the raw materials are consumed, the reaction mixture was filtered through a celite pad to remove the solid and the filtrate was evaporated under reduced pressure and purified by reversed phase prep-HPLC to give 501-4 as Compound 26 (17 mg, 14.5% yield) as a white solid. $^1$H NMR (400 MHz, DMSO-$d_6$) δ 10.95 (d, J=9.2 Hz, 1H), 8.90 (s, 1H), 8.78 (d, J=2.0 Hz, 1H), 8.54 (d, J=2.4 Hz, 1H), 7.43 (s, 1H), 4.46-4.39 (s, 2H), 2.56 (t, J=11.2 Hz, 1H), 2.22 (t, J=12.0 Hz, 1H), 1.87-1.74 (m, 2H), 1.63-1.59 (m, 1H), 0.91-0.82 (m, 7H). LC/MS (ESI): m/z=358.0 [M+1]+. RT=1.674 min.

Compound 27—Y=S, X=O, G=CF, R=H, $R^1$&$R^2$=—$CH_2CH(CH_3)CH_2CH(CH_3)CH_2$—

Step-1: see Step-1 of Compound 26 for details.

Step-2: A suspension of amide 501-2 (66 mg, 0.22 mmol), arylamine 501-3 (50 mg, 0.33 mmol), $Cs_2CO_3$ (142 mg, 0.44 mmol), $Pd_2(dba)_3$ (20 mg, 0.022 mmol) and Xantphos (13 mg, 0.022 mmol) in 1,4-dioxane (15 mL) was stirred at 105° C. overnight under nitrogen atmosphere. After the raw materials are consumed, the reaction mixture was filtered through a celite pad to remove the solid and the filtrate was evaporated under reduced pressure and purified by reversed phase pre-HPLC to give 501-4 as Compound 27 (14 mg, 17.3% yield) as a white solid. $^1$H NMR (400 MHz, DMSO-$d_6$) δ: 10.82 (s, 1H), 8.70 (s, 1H), 8.06 (d, J=1.6 Hz, 1H), 7.43-7.40 (m, 2H), 4.46-4.39 (m, 2H), 2.55-2.50 (m, 1H), 2.22-2.20 (m, 1H), 1.87-1.78 (m, 2H), 1.62-1.59 (m, 1H), 0.91-0.82 (m, 7H). LC/MS (ESI): m/z=374.8 $[M+1]^+$. RT=9.857 min.

General Scheme 6: Experimental Procedure for the Synthesis of Compound 20

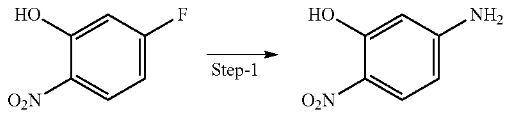

398-1

398-2

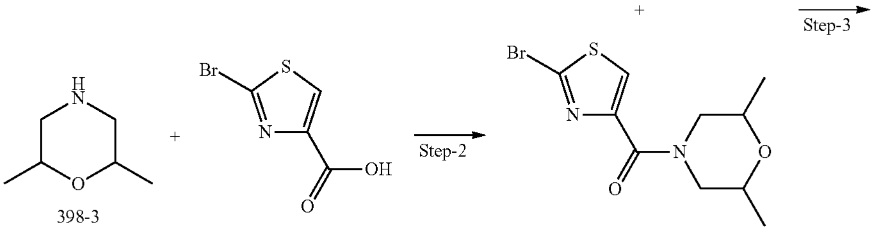

398-3

398-4

398-5

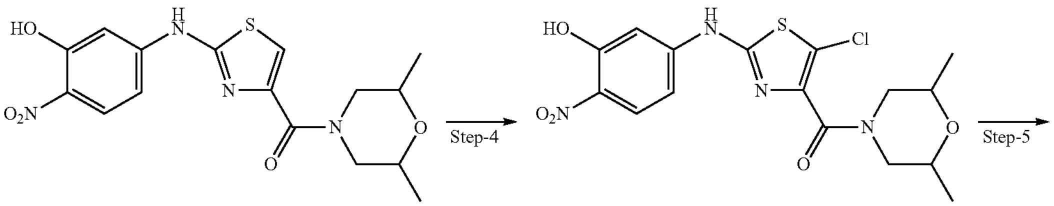

398-6

398-7

-continued

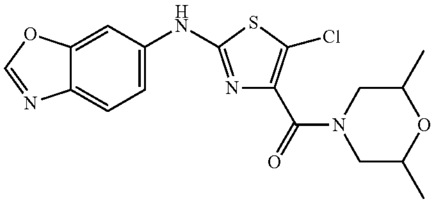

Compound 20

Experimental Procedure for General Scheme 6

Step-1: A mixture of fluoroaryl 398-1 (1.0 g, 6.37 mmol) in $NH_3 \cdot H_2O$ (3.0 mL) was stirred at 140° C. in microwave-assisted for 20 minutes. After all the raw materials are consumed, the mixture was concentrated and added water (30 mL) and EtOAc (30 mL), and the phases were separated. The organic phase was washed with aqueous $NaHCO_3$ and brine successively, dried over $Na_2SO_4$, concentrated and purified by column chromatography on silica gel (eluting with 0~25% EtOAc in PE) to give arylamine 398-2 (420 mg, 42.8% yield) as a yellow solid. LC/MS (ESI): m/z=155.2 $[M+H]^+$. RT=1.384 min.

Step-2: To a solution of carboxylic acid 398-4 (416 mg, 2.0 mmol) and amine 398-3 (0.54 mL, 4.0 mmol) in DMF (20 mL) was added EDCI·HCl (575 mg, 3.0 mmol), HOBt (405 mg, 3.0 mmol) and DIEA (1.31 mL, 8.0 mmol), and the reaction mixture was allowed to stir at room temperature overnight. After the raw materials are consumed, the reaction mixture was diluted by water (50 mL) and extracted with EtOAc (3×30 mL). The organic extract was washed by water (4×50 mL) and brine (50 mL) successively, dried over anhydrous $Na_2SO_4$, filtered, evaporated under reduced pressure and purified by column chromatography on silica gel (eluting with 0%~30% EtOAc in PE) to give amide 398-5 (410 mg, 67.2% yield) as a colorless gel. LC/MS (ESI): m/z=305.0 $[M+H]^+$. RT=1.611 min.

Step-3: A mixture of amide 398-5 (420 mg, 1.38 mmol), 5-amino-2-nitrophenol (319 mg, 2.07 mmol), $Cs_2CO_3$ (897 mg, 2.76 mmol), $Pd_2(dba)_3$ (126 mg, 0.14 mmol) and Xantphos (80 mg, 0.14 mmol) in toluene (40 mL) was stirred at 100° C. for 1.5 days under Ar. atmosphere. After consumption of starting material, the mixture was evaporated under reduced pressure to remove toluene and purified by column chromatography on silica gel (eluting with EtOAc) to give thiazole 398-6 (270 mg, 51.8% yield) as a yellow solid. LC/MS (ESI): m/z=379.0 $[M+H]^+$. RT=1.685 min.

Step-4: To a solution of thiazole 398-6 (270 mg, 0.71 mmol) in THF (15 mL) was added NCS (108 mg, 0.86 mmol) and the reaction mixture was allowed to stir at 50° C. for 5 h under Ar. atmosphere. After consumption of the starting material, the mixture was evaporated under reduced pressure to remove THF and purified by column chromatography on silica gel (eluting with 0~60% EtOAc in PE) to give chlorothiazole 398-7 (110 mg, 37.4% yield) as a yellow solid. LC/MS (ESI): m/z=413.0 $[M+H]^+$. RT=1.748 min.

Step-5: A mixture of chlorothiazole 398-7 (110 mg, 0.27 mmol), $PtO_2$ (61 mg, 0.27 mmol), $ZnCl_2$ (37 mg, 0.27 mmol) and $HC(OC_2H_5)_3$ (3.0 mL) in MeOH (20 mL) was purged with hydrogen and stirred at room temperature overnight under hydrogen atmosphere. After all the raw materials are consumed, the reaction mixture was filtered through a celite pad to remove the solid and the filtrate was evaporated under reduced pressure and purified by reversed phase prep-HPLC to give Compound 20 (25 mg, 23.8% yield) as a brown solid. $^1H$ NMR (400 MHz, $CD_3OD$) δ 8.39 (s, 1H), 8.31 (d, J=2.0 Hz, 1H), 7.65 (d, J=8.8 Hz, 1H), 7.30 (dd, J=8.8, 2.0 Hz, 1H), 4.48 (d, J=13.2 Hz, 1H), 3.80 (d, J=12.8 Hz, 1H), 3.76-3.66 (m, 2H), 2.92 (dd, J=13.2, 10.4 Hz, 1H), 2.60 (dd, J=12.8, 10.8 Hz, 1H), 1.25 (d, J=6.4 Hz, 3H), 1.12 (d, J=6.0 Hz, 3H). LC/MS (ESI): m/z=392.8 $[M+1]^+$. RT=7.990 min.

Example 2—Biological Activity

The compounds of the invention inhibit TRPC3, TRPC6, TRPC7 ion channels, or combinations thereof. The compounds may therefore be useful for the prevention or treatment of conditions or diseases associated with TRPC3, TRPC6, TRPC7 ion channel activity, or combinations thereof, in particular conditions or diseases responsive to the inhibition of TRPC3 and/or TRPC6 and/or TRPC7 ion channel activity. The biological activity of compounds of Formula I can be determined using any suitable assay for determining the activity of a candidate compound as a TRPC3, TRPC6, TRPC7 inhibitor, or combinations thereof, as well as tissue and in vivo models.

Biological Example 1: TRPC3, TRPC6, TRPC7 Blocking

The biological activity of compounds of Formula I were assessed and confirmed to have inhibitory effects by the FLIPR assay. Compounds were screened for activity on TRPC6 ion channel (Test 1 & Test 2), followed by screening for TRPC3, TRPC6 and TRPC7 ion channels (Test 3).

Methods

TRPC6 channel activity was tested according to Test 1 (GSK1702934A), HEK-293 cells stably expressing the human TRPC6 channel (hTRPC6) were seeded at a rate of 15,000 cells/well onto 384 well plate in culture media (Dulbecco's Modified Eagle Medium, 10% Fetal Bovine Serum and 1% G418). Following 16-24 hours of seeding, the media was removed, and cells were incubated with a membrane potential sensitive dye (FLIPR® Membrane Potential Assay Kit (blue), Molecular Devices) in assay buffer (Hank's Balanced Salt Solution, 20 mM HEPES, pH 7.4) for 30 mins at 37° C., followed by addition of serial dilutions of the compounds (0.5% DMSO) for 15 mins at room temperature. The agonist GSK1702934A was added next at $EC_{80}$ concentration and the change in fluorescence dye was captured using the $FTIRP^{TETRA}$ system. The $IC_{50}$ values for each compound are presented in Table 2.

TRPC6 channel activity was tested according to Test 2, (Carbochol), HEK-293 cells stably expressing the human TRPC6 channel (hTRPC6) were seeded at a rate of 15,000 cells/well onto 384 well plate in culture media (Dulbecco's Modified Eagle Medium, 10% Fetal Bovine Serum and 1% G418). Following 16-24 hours of seeding, the media was removed, and cells were incubated with a membrane potential sensitive dye (FLIPR® Membrane Potential Assay Kit (blue), Molecular Devices) in assay buffer (Hank's Balanced Salt Solution and 20 mM HEPES. pH 7.4) for 30 mins at 37° C., followed by addition of serial dilutions of the compounds (0.5% DMSO) for 15 mins at room temperature. The agonist carbachol was added next at $EC_{80}$ concentration and the change in fluorescence dye was captured using the FTIRP$^{TETRA}$ system. The $IC_{50}$ values for each compound are presented in Table 2.

TRPC3/6/7 channel activity was tested according to Test 3, compounds were screened for their ability to block TRPC3, TRPC6 and TRPC7 channels in a membrane potential assay. The experiments were performed using HEK-293 stably transfected with either hTRPC3 or hTRPC6 or hTRPC7. 50,000 cells/well were seeded onto 96 well plate in culture media. Following 24 hours of seeding, the media was removed, and cells were incubated with a membrane potential sensitive dye (FLIPR® Membrane Potential Assay Kit (blue), Molecular Devices) in assay buffer (Hank's Balanced Salt Solution, 20 mM, HEPES, pH 7.4) for 1 hour at 37° C. Serial dilutions of the compounds were added (0.5% DMSO) were added to the wells and incubated for 15 minutes at room temperature, followed by addition of the agonist carbachol at $EC_8$. Change in fluorescence dye was captured using the FLIRP-TETRA system (Molecular Devices). The TRPC3/6/7 ion-channel blocking $IC_{50}$ values of example compounds are presented in Table 3.

All tests confirmed the compounds of the invention have good inhibitory effects on their intended targets, with $IC_{50}$s in the low nM to low μM amounts.

TABLE 2

Results of the TRPC3, TRPC6 and TRPC7 ion channel assays.

| | $IC_{50}$ (nM) | | | | |
|---|---|---|---|---|---|
| Compound Number | Test 1 TRPC6 | Test 2 TRPC6 | Test 3 TRPC3 | Test 3 TRPC6 | Test 3 TRPC7 |
| 1 | 35 | 53 | 43 | 22 | 8 |
| 2 | 45 | 89 | 162 | 115 | 15 |
| 3 | 110 | 94 | 140 | 30 | 7 |
| 4 | 380 | | | | |
| 5 | 497 | | | | |
| 6 | 370 | 288 | 1,076 | 562 | 157 |
| 7 | 340 | | | | |
| 8 | 400 | | | | |
| 9 | 245 | | | | |
| 10 | | 392 | | | |
| 11 | | 220 | | | |
| 12 | | 198 | | | |
| 13 | | 908 | | | |
| 14 | | 488 | | | |
| 15 | | 531 | | | |
| 16 | | 67 | | | |
| 17 | | 186 | | | |
| 18 | | 403 | | | |

Biological Example 2: Cytotoxicity Properties

Cytotoxicity is an undesirable property of a pharmaceutical intended for treatment of various neurological conditions. The higher the $IC_{50}$ the lower the cytotoxicity of a compound.

The cytotoxicity activity of compounds of Formula I were assessed and confirmed to have low cytotoxicity properties. Compounds were screened for cytotoxicity activity on HepG2 and TK6 cell lines.

Methods

Cytotoxicity was tested according to Test 4, TK6 cells are of lymphoblastic origin and are routinely used to assess chemically-induced genotoxicity. TK6 cells were seeded at a density of 3000 cells/well in a 384-well plate. Twenty-four hours later, cells were treated with test compound for 48 hours in 3-fold serial dilutions with a top test concentration of 50 μM. After the incubation, CellTiter-Glo reagent was added directly to the wells. The plate was shaken for 5 mins on a plate shaker then incubated at room temperature for a further 10 mins and the luminescence was recorded on a plate reader.

Cytotoxicity was tested according to Test 5, HepG2 is a human hepatoma commonly used in drug metabolism and hepatotoxicity studies. HepG2 cells were seeded at a density of 7000-8000 cells/well in a 96-well plate. Twenty to twenty-four hours later, cells were treated with test compound for 48 hours in 3-fold serial dilutions with a top test concentration of 50 μM. After the incubation, CellTiter-Glo reagent was added directly to the wells. The plate was shaken for 10 mins on a plate shaker then incubated at room temperature for a further 10 mins minutes to stabilize luminescent signal. Subsequently, 100 μL of the above solution was transferred to a white flat bottom opaque 96 well plate (or opaque-walled clear bottom plates taped with a white bottom seal) and luminescence recorded on a plate reader.

The cytotoxicity $IC_{50}$ values of example compounds are presented in Table 3.

TABLE 3

Cytotoxicity of select example compounds of this invention on various cell lines.

| Compound Number | $IC_{50}$ (μM) Test 1 TK6 | $IC_{50}$ (μM) Test 2 HepG2 |
|---|---|---|
| 1 | >30 | |
| 2 | | 11.8 |
| 3 | 25.5 | |
| 6 | 33.4 | >30 |
| 12 | >50 | 28.1 |

Compounds with $IC_{50}$s greater than 10 μM can be considered to possess low cytotoxicity potential.

Biological Example 3: Pharmacokinetics (PK) Study

The pharmacokinetics of Compound 1 was assessed following bolus and continuous intravenous (i.v.) dosing. Mice ($C_{57}$BL/6, males, 18-20 g) aged 6-8 weeks were administered with a single dose of 4.2 mg/kg of Compound 1 (5 ml/kg) via a tail vein injection (formulated in 5% DMAC, 5% Solutol HS and 90% saline). Blood samples were drawn via the facial vein into pre-cooled $K_2$EDTA tubes, followed by transcardial perfusion with saline and extraction of fresh brain tissues at 0.25, 0.5, 1, and 2 hours (n=3 per time point, per dose). The blood samples were put on ice and centrifuged to obtain plasma samples (2,000 g, 5 mins, 4° C.) within 15 mins of sample collection.

The plasma and diluted brain samples (1 in 4 dilution in PBS) were mixed with internal standard (diclofenac, 50 ng/mL) in acetonitrile. The mixture was centrifuged (5,800 rpm) and analyzed using the LC-MS/MS technique.

The mean plasma and brain concentrations and PK parameters for Compound 1 following single i.v. dose are described in Table 4 and FIG. 1. The half-life of Compound 1 following i.v. injection was 13 minutes, the clearance was 3,950 mL/h/kg and the plasma to brain ratio was 0.57 at 15 minutes post-injection suggesting that Compound 1 readily crossed the blood-brain barrier, a feature critical for target engagement in the brain tissue.

TABLE 4

Mean plasma concentrations of Compound 1 in the mouse following a single 4.2 mg/kg intravenous dose.

| | Mean Concentration (ng/mL) | | |
|---|---|---|---|
| Sampling time (h) | Plasma | Brain | Brain to Plasma Ratio |
| 0.25 | 1194 | 700 | 0.573 |
| 0.5 | 288 | 144 | 0.513 |
| 1 | 47.8 | 21.8 | 0.451 |
| 2 | 2.42 | BQL | NA |

Infusion Study

The mean plasma and brain concentrations and PK parameters for Compound 1 were also assessed following 72-hour continuous intravenous infusion dosing in male C57BL6 mice aged 6-8 weeks (body weight, 20-25 g) Sprague-Dawley rats aged 6-8 weeks (body weight, 195-225 g). Mice and rats were dosed continuously for 72 hours with 2 mg/kg/h and 5 mg/kg/h dose respectively, at 1 mL/kg/h infusion rate via the jugular vein (formulated in 10% DMSO+10% Solutol HS-15+25% PEG300+15% PG, 40% (0.1% Tween80 in 50 mM Carbonate buffer pH 9). In mice, the blood samples were collected at 0.5, 1, 2, 4, 6, 12, 24, 48, 72 and 72.5 hours via the facial vein and from a separate cohort blood and brain tissue was obtained at 2, 6 and 72 hours post infusion onset. In rats, the blood samples were collected at 2, 6, 24, 48 and 72 hours post infusion onset via the facial vein and brain tissue was collected at 72 hours.

Figure 2A:
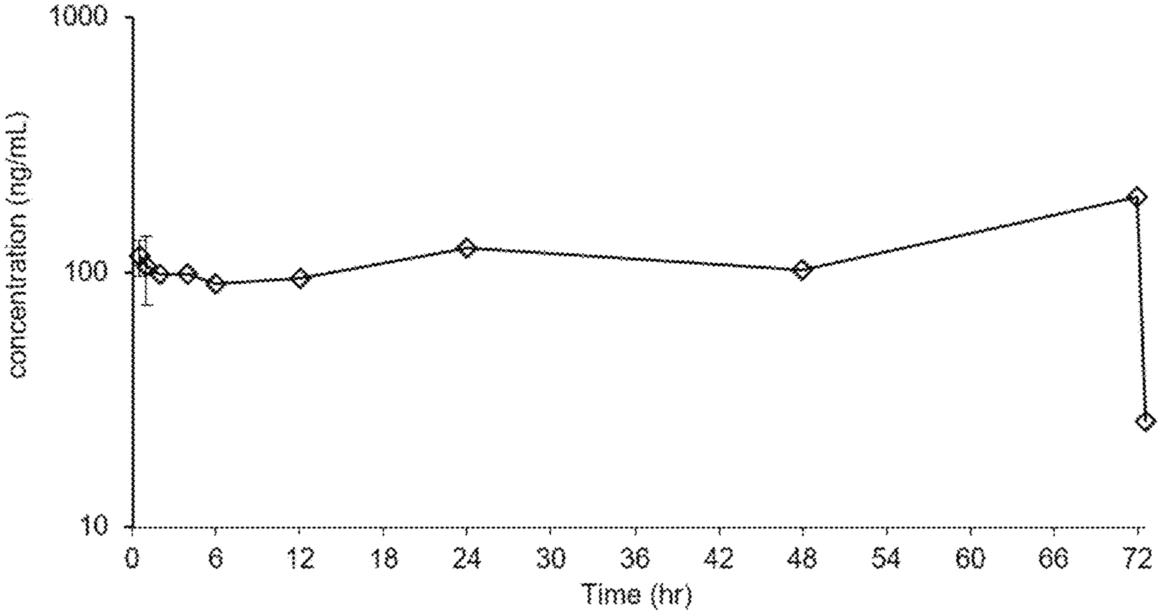
FIG. 2A: Graph showing the mean plasma concentration of Compound 1 following continuous intravenous infusion over 72 hours in male mice at 2 mg/kg/h (n=3).
Figure 2B:
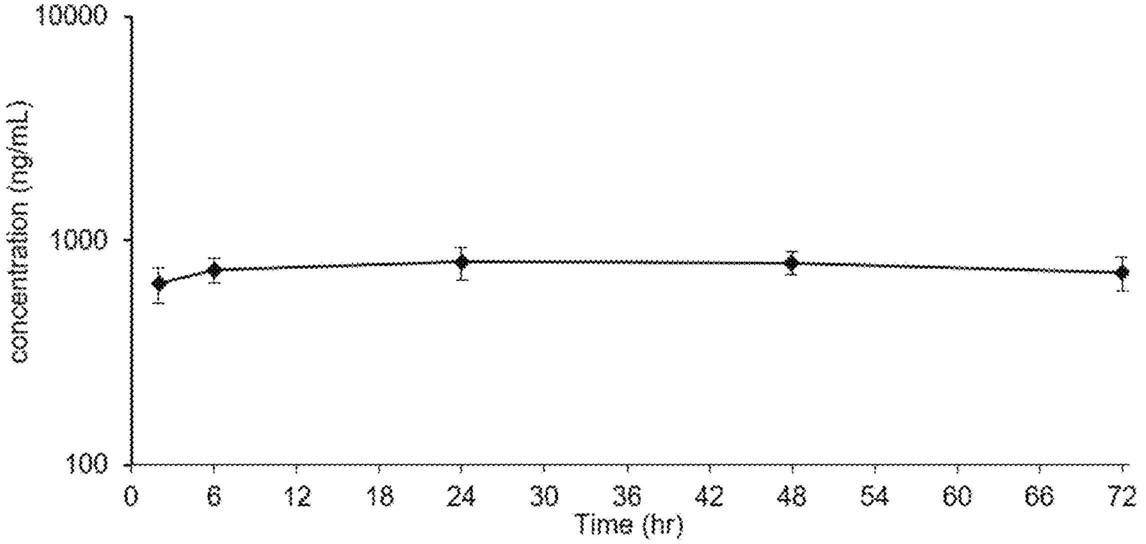
FIG. 2B: Graph showing the mean plasma concentration of Compound 1 following continuous intravenous infusion over 72 hours in male rats at 5 mg/kg/h (n=3).

The mean plasma and brain concentrations in mice and rats post continuous i.v. infusion are described in Tables 5a and 5b, respectively, and graphically in FIGS. 2A and 2B, respectively. The mean brain to plasma ratio of Compound 1 following a 72-hour intravenous infusion was 0.5 in mice and 1.1 in rats.

TABLE 5a

Mean plasma concentrations of Compound 1 in the mouse and rat following continuous intravenous infusion dosing.

| Species and dose | Timepoint post infusion onset (h) | Mean Plasma concentration (ng/mL) |
|---|---|---|
| Mouse | 0.5 | 15 |
| 2 mg/kg/h | 1 | 107 |
| | 2 | 99 |
| | 4 | 99 |
| | 6 | 90 |
| | 12 | 95 |
| | 24 | 125 |
| | 48 | 102 |
| | 72 | 298 |
| | 72.5 | 26 |
| Rat | 2 | 641 |
| 5 mg/kg/h | 6 | 741 |
| | 24 | 800 |
| | 48 | 797 |
| | 72 | 721 |

TABLE 5b

Brain to plasma ratio of Compound 1 in the mouse and rat following continuous intravenous infusion dosing.

| Species and dose | Timepoint post infusion onset (h) | Mean plasma concentration (ng/mL) | Mean brain concentration (ng/mL) | Brain to plasma ratio |
|---|---|---|---|---|
| Mouse | 2 | 130 | 83 | 0.66 |
| 2 mg/kg/h | 6 | 134 | 68 | 0.54 |
| | 72 | 206 | 105 | 0.52 |
| Rat 5 mg/kg/h | 72 | 721 | 786 | 1.11 |

Biological Example 4: Activity in an Animal Model of Focal Ischemia

Compound 1 of the invention was assessed for efficacy in a model of focal ischemia in mice achieved using a photothrombotic induced-lesion.

Photothrombosis was induced in male mice (C57BL/6, n=8 each treatment) aged 10-12 weeks via irradiation of the exposed skull with light at 532 nm wavelength for 5 minutes, immediately preceded by injection of rose bengal dye (50 mg/kg) via the tail vein. Thirty minutes post lesion, the mice were delivered with vehicle or a compound of the invention (5 mg/kg/h formulated in 10% DMSO+10% Solutol HS-15+25% PEG300+15% PG, 40% (0.1% Tween80 in 50 mM Carbonate buffer pH 9) for 72 hours via continuous i.v. infusion through jugular vein cannulation. Seventy-two hours post-infusion, the animals were euthanized and transcardially perfused with 4% paraformaldehyde (PFA) to fix the brain tissue. The excised fixed heads were immersed in PBS/0.2% v/v Gadopentetic acid (Gd-DTPA) contrast agent for 14-20 days, then placed into an imaging vial and submerged in PCF oil (FomblinY®) and scanned for T2-weighted and diffusion tensor imaging (DTI) modalities using the 9.4 T Bruker (Karlsruhe, Germany) BioSpec Avance III 94/20 system.

MRI Imaging and Analysis

Imaging was performed on a 9.4 Tesla Bruker BioSpec BioSpec Avance III 94/20 system quadrature volume coils, running Bruker ParaVision 6.0.1 software. The protocol provided stacks of 3D T2-weighted, perfusion and diffusion-weighted images in the axial plane. For T2-weighted images, the TurboRARE method, also called fast spin echo method, was used (TE/TR=36/2500 ms, with field of view=18×18 mm, Resolution 60×60 μm, slice thickness=300 μm, contiguous slices, 21 slices per volume, acquisition time=30 min/Volume (TurboRARE).

For diffusion-weighted imaging, the spin-echo multi-shot echo-planar method was used (TE/TR=22/2,000 ms, Segmented EPI, 4 partitions, field of view=18×18 mm, Resolution 120×120 μm, slice thickness 500 μm, 100 μm slice gap, 9 slices per volume, acquire time=3 h 6 min/map; gradient direction=30 and gradient b-value=1,000 s/mm$^2$).

Figure 3:
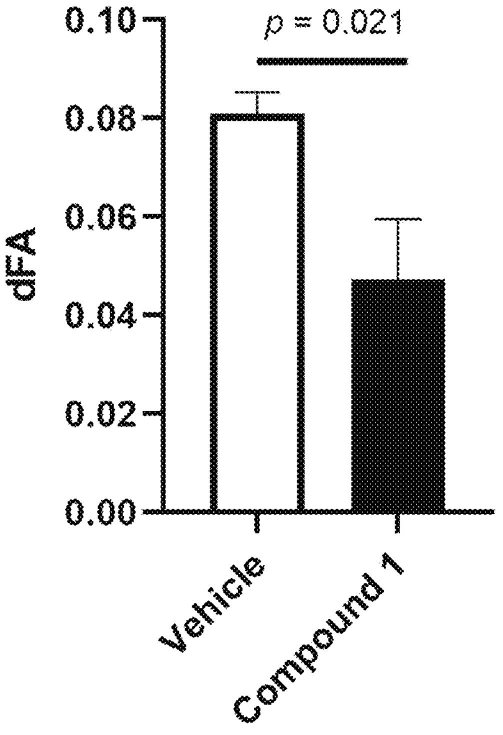
FIG. 3: Bar graph showing the delta FA (dFA) values demonstrating the difference in FA values between uninjured and injured penumbra zones. The dFA is significantly less in the animals treated with Compound 1 (n=8) compared with vehicle treated animals (n=7) (p=0.021, Mann-Whitney Rank Sum test). Data represents mean±standard error of mean.

Diffusion images were post-processed in UNSW provided python script and 3D Slicer 4.11 to calculate the fractional anisotropy values. Damaged tissue has a lower FA value compared to non-damaged tissue. As such, the difference between the FA values were compared between the injured (ipsilateral) and uninjured (contralateral) hemispheres of the brain in 3 zones lying immediately besides the primary injury. The average difference between the FA values (dFA) in the injured and uninjured sides in animals from vehicle treated group were significantly higher than the difference in the Compound 1 treated (5 mg/kg/h) group in zones 1 and 2 (FIG. 3). By zone 3, the difference between the injured and uninjured sides in both treatment groups neared zero, meaning that the secondary injury had not propagated beyond zone 2.

The combination of T2 images and FA values were used to demarcate the core primary injury area, then complete whole brain masking was undertaken to include the Fiducials for standardizing the 3D orientation for mirroring of the lesion to contralateral side (as a normal tissue reference). Following the mirroring of the core lesion, eroding of 240 $\mu m^3$ voxels using DTI traces was undertaken to provided normalized FA values, extending as three zones (2×120 $\mu m^3$ voxels per zone) from the perimeter of the primary infarct core (~1 mm radius) on a slice-by-slice basis. The analysis was performed blinded to the treatment.

Damaged tissue has a lower FA value compared to non-damaged tissue. As such, the difference between the FA values were compared between the injured (ipsilateral) and uninjured (contralateral) hemispheres of the brain in three zones lying immediately besides the primary injury. The average difference between the FA values (dFA) in the injured and injured sides in animals from vehicle treated group were significantly higher than the difference in the Compound 1 treated (5 mg/kg/hour) group in zones 1 and 2 (FIG. 3). By zone 3, the difference between the injured and uninjured sides in both treatment groups neared zero, meaning that the secondary injury had not propagated beyond zone 2.

Biological Example 5: Comparative Examples of TRPC3/6/7 Blocking of Compounds not of this Invention The biological activity of example compounds not of the invention were assessed by the FLIPR assay. Compounds were screened for activity on TRPC6 ion channel (Test 1 & Test 2), and TRPC3, TRPC6 and TRPC7 ion channels (Test 3).

TRPC6 channel activity was tested according to Test 1, where HEK-293 cells stably expressing the human TRPC6 channel (hTRPC6) were seeded at a rate of 15,000 cells/well onto 384 well plate in culture media (Dulbecco's Modified Eagle Medium, 10% Fetal Bovine Serum and 1% G418). Following 16-24 hours of seeding, the media was removed, and cells were incubated with a membrane potential sensitive dye (FLIPR® Membrane Potential Assay Kit (blue), Molecular Devices) in assay buffer (Hank's Balanced Salt Solution, 20 mM and 2% HEPES, pH 7.4) for 30 mins at 37° C., followed by addition of serial dilutions of the compounds (0.5% DMSO) for 15 mins at room temperature. The agonist GSK1702934A was added next at $EC_{80}$ concentration and the change in fluorescence dye was captured using the FTIRP$^{TETRA}$ system. The $IC_{50}$ values for each compound are presented in Table 6.

TRPC6 channel activity was tested according to Test 2, where HEK-293 cells stably expressing the human TRPC6 channel (hTRPC6) were seeded at a rate of 15,000 cells/well onto 384 well plate in culture media (Dulbecco's Modified Eagle Medium, 10% Fetal Bovine Serum and 1% G418). Following 16-24 hours of seeding, the media was removed, and cells were incubated with a membrane potential sensitive dye (FLIPR® Membrane Potential Assay Kit (blue), Molecular Devices) in assay buffer (Hank's Balanced Salt Solution, 20 mM and 2% HEPES, pH 7.4) for 30 mins at 37° C., followed by addition of serial dilutions of the compounds (0.5% DMSO) for 15 mins at room temperature. The agonist carbachol was added next at $EC_{80}$ concentration and the change in fluorescence dye was captured using the FTIRP$^{TETRA}$ system. The $IC_{50}$ values for each compound are presented in Table 6.

TRPC3/6/7 channel activity was tested according to Test 3, where compounds were screened for their ability to block TRPC3, TRPC6 and TRPC7 channels in a membrane potential assay. The experiments were performed using HEK-293 stably transfected with either hTRPC3 or hTRPC6 or hTRPC7. 50,000 cells/well were seeded onto 96 well plate in culture media. Following 24 hours of seeding, the media was removed, and cells were incubated with a membrane potential sensitive dye (FLIPR® Membrane Potential Assay Kit (blue), Molecular Devices) in assay buffer (20 mM Hank's Balanced Salt Solution, HEPES, pH 7.4) for 1 hour at 37° C. Serial dilutions of the compounds were added (0.5% DMSO) were added to the wells and incubated for 15 minutes at room temperature, followed by addition of the agonist carbachol at $EC_{80}$. Change in fluorescence dye was captured using the FLIRP-TETRA system (Molecular Devices). The TRPC3/6/7 ion-channel blocking $IC_{50}$ values of example compounds are presented in Table 6.

Test 4 TK6 cells are of lymphoblastic origin and are routinely used to assess chemically-induced genotoxicity. TK6 cells were seeded at a density of 3000 cells/well in a 384-well plate. Twenty-four hours later, cells were treated with test compound for 48 hours in 3-fold serial dilutions with a top test concentration of 50 μM. After the incubation, CellTiter-Glo reagent was added directly to the wells. The plate was shaken for 5 mins on a plate shaker then incubated at room temperature for a further 10 mins and the luminescence was recorded on a plate reader.

Test 5 HepG2 is a human hepatoma commonly used in drug metabolism and hepatotoxicity studies. HepG2 cells were seeded at a density of 7000 or 8000 cells/well in a 96-well plate. Twenty to twenty-four hours later, cells were treated with test compound for 48 hours in 3-fold serial dilutions with a top test concentration of 50 μM. After the incubation, CellTiter-Glo reagent was added directly to the wells. The plate was shaken for 10 mins on a plate shaker then incubated at room temperature for a further 10 mins minutes to stabilize luminescent signal. Subsequently, 100 μL of the above solution was transferred to a white flat bottom opaque 96 well plate (or opaque-walled clear bottom plates taped with a white bottom seal) and luminescence recorded on a plate reader.

TABLE 6
Results of TRPC3/6/7 ion channel blocking assay and cytotoxicity of comparative compounds not of the invention.
| | | $IC_{50}$ (nM) | | | | | $IC_{50}$ (μM) | |
|---|---|---|---|---|---|---|---|---|
| | Compound Structure | TRPC6 Test 1 | TRPC6 Test 2 | TRPC3 Test 3 | TRPC6 Test 3 | TRPC7 Test 3 | TK6 Test 4 | HepG2 Test 5 |
| A1 | 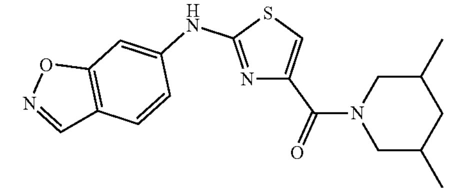 [SMILES: CC1CC(C)CN(C(=O)c2csc(Nc3ccc4cnoc4c3)n2)C1] | >10,000 | | | | | | |
| A2 | 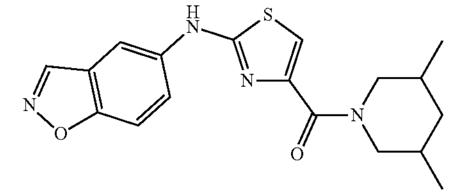 [SMILES: CC1CC(C)CN(C(=O)c2csc(Nc3ccc4oncc4c3)n2)C1] | >10,000 | | | | | | |
| A3 | 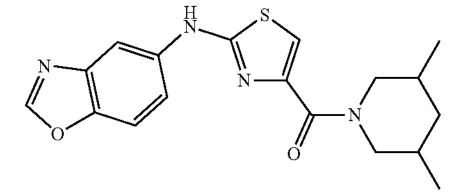 [SMILES: CC1CC(C)CN(C(=O)c2csc(Nc3ccc4ocnc4c3)n2)C1] | 384 | | 3,039 | 1,546 | 62 | | |
| A4 | 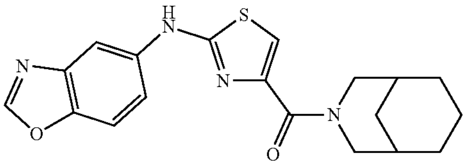 [SMILES: O=C(c1csc(Nc2ccc3ocnc3c2)n1)N1CC2CCCC(C2)C1] | 1,500 | | | | | | |
| A5 | 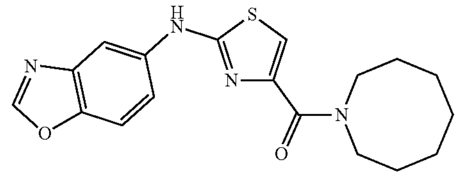 [SMILES: O=C(c1csc(Nc2ccc3ocnc3c2)n1)N1CCCCCCC1] | 739 | | | | | | |
| A6 | 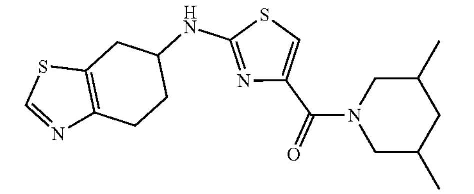 [SMILES: CC1CC(C)CN(C(=O)c2csc(NC3CCc4ncsc4C3)n2)C1] | >10,000 | | | | | | |
| A7 | 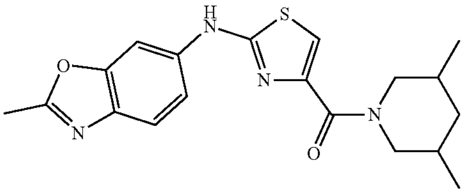 | 56 | 22 | 24 | 1 | 2 | 4.99 | 0.26 |

TABLE 6-continued
Results of TRPC3/6/7 ion channel blocking assay and cytotoxicity of comparative compounds not of the invention.
| | Compound Structure | $IC_{50}$ (nM) | | | | | $IC_{50}$ (μM) | |
|---|---|---|---|---|---|---|---|---|
| | | TRPC6 Test 1 | TRPC6 Test 2 | TRPC3 Test 3 | TRPC6 Test 3 | TRPC7 Test 3 | TK6 Test 4 | HepG2 Test 5 |
| A8 | 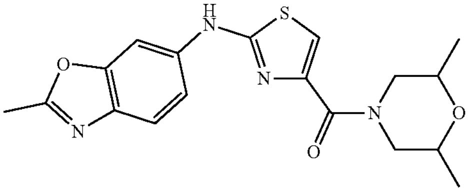 | | 166 | 736 | 119 | 66 | 5.7 | 0.62 |
| A9 | 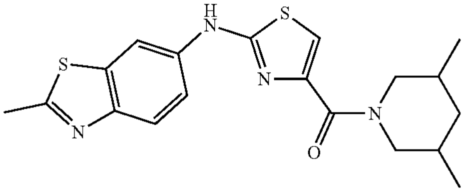 | | 42 | 44 | 9 | 7 | 0.15 | ND |
| A10 | 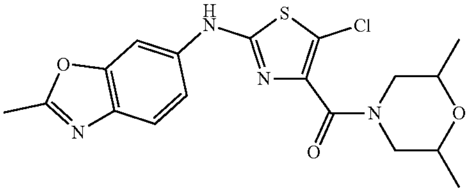 | | 140 | 1,646 | 121 | 46 | 0.81 | 0.098 |
| A11 | 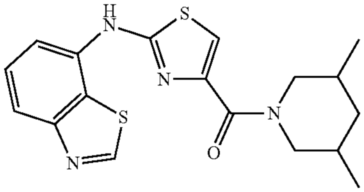 [SMILES: CC1CC(C)CN(C(=O)c2csc(Nc3cccc4ncsc34)n2)C1] | | 1,817 | | | | | |
| A12 | 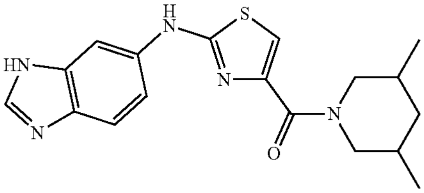 [SMILES: CC1CC(C)CN(C(=O)c2csc(Nc3ccc4nc[nH]c4c3)n2)C1] | >10,000 | ND | | | | | |
| A13 | 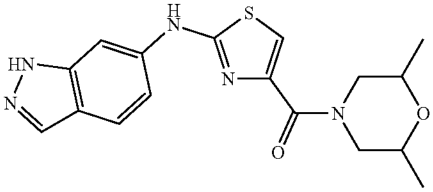 [SMILES: CC1CN(C(=O)c2csc(Nc3ccc4cn[nH]c4c3)n2)CC(C)O1] | | >10,000 | | | | | |
| A14 | 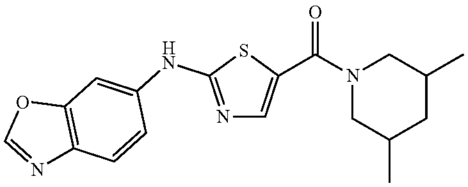 [SMILES: CC1CC(C)CN(C(=O)c2cnc(Nc3ccc4ncoc4c3)s2)C1] | | >10,000 | | | | | |

Examples A1 and A2 contain benzisoxazoles instead of the benzoxazole/thiazole of the compounds of the invention. They display low TRPC3/6/7 ion-channel blocking activity. The differences show that the benzoxazole/thiazole is required for suitable activity against the TRPC3/6/7 ion-channels.

Examples A3, A4 and A5 contain 5-substitution configuration of the benzoxazole/thiazole instead of the 6-substitution of the compounds of the invention. They display low TRPC3/6/7 ion-channel blocking activity. The differences show that the benzoxazole/thiazole is required to be the 6-substitution configuration for suitable activity against the TRPC3/6/7 ion-channels.

Example A6 contains a 4,5,6,7-tetrahydro-1,3-benzothiazole instead of the benzoxazole/thiazole of the compounds of the invention. It displays low TRPC3/6/7 ion-channel blocking activity. The differences show that the benzoxazole/thiazole is required for suitable activity against the TRPC3/6/7 ion-channels.

Examples A7, A8, A9 and A10 contain 2-methyl substitution of the benzoxazole/thiazole instead the unsubstituted benzoxazole/thiazole of the compounds of the invention. They display moderate to high TRPC3/6/7 ion-channel blocking activity but also moderate to high undesired cytotoxicity. The differences show that the unsubstituted benzoxazole/thiazole is required for suitable cytotoxicity properties whilst maintaining TRPC3/6/7 ion-channel blocking activity.

Example A11 contains 7-substitution of the benzoxazole/thiazole instead of the 6-substitution of the benzoxazole/thiazole of the compounds of the invention. It displays low TRPC3/6/7 ion-channel blocking activity. The differences show that the benzoxazole/thiazole is required to be the 6-substitution configuration for suitable activity against the TRPC3/6/7 ion-channels.

Examples A12 and A13 contain benzodiazoles instead of the benzoxazole/thiazole of the compounds of the invention. They display low TRPC3/6/7 ion-channel blocking activity. The differences show that the benzoxazole/thiazole is required for suitable activity against the TRPC3/6/7 ion-channels.

Example A14 contains a 2,5-substituted thiazole instead of the 2,4-substituted thiazole/oxazole of the compounds of the invention. It displays low TRPC3/6/7 ion-channel blocking activity. The differences show that the 2,4-substituted thiazole is required for suitable activity against the TRPC3/6/7 ion-channels.

Compounds of the invention are expected to show improved efficacy compared to any compounds of prior art.

Biological Example 6: Activity in Penetrating Traumatic Brain Injury Model

Compound 1 of the invention was assessed for efficacy in a model of severe traumatic brain injury in rats achieved using a penetrating ballistic brain injury (PTBI) model.

All surgical procedures were performed under isoflurane anesthesia (3-5% for induction and 2% for maintenance) and aseptic conditions with careful monitoring of physiological vital signs in male Sprague-Dawley rats aged 10-12 weeks (300-350 g). Anesthetized rats were placed on a thermal blanket to regulate body temperature (37° C.), and rats' heads secured in the stereotaxic device for insertion of a probe. After a midline scalp incision, a right frontal cranial window (diameter=4 mm) was created using a dental drill to expose the right frontal pole (+4.5 mm AP, +2 mm mediolateral to bregma). The probe was then be advanced through the cranial window into the right hemisphere to a depth of 1.2 cm from the surface of the brain. Once the probe was in place, the pulse generator was activated by a computer to release a pressure pulse calibrated to produce a rapid expansion of the waterfilled elastic tubing (probe) to induce an elliptical shaped balloon (diameter=0.633 mm; duration=40 ms) to a volume equal to 7.5% of total brain volume. After deflation, the probe was manually retracted from the brain, the cranial opening sealed with sterile bone wax, and the skin incision closed with wound clips.

Thirty minutes post injury, the rats were administered with either vehicle of Compound 1 at 5 mg/kg/h (formulated in 10% DMSO+10% Solutol HS-15+25% PEG300+15% PG, 40% (0.1% Tween80 in 50 mM Carbonate buffer pH 9) for 48 hours via an indwelling catheter implanted in the jugular vein one day prior to the PTBI surgery. Forty-eight hours post infusion, the animals were euthanized and transcardially perfused with 4% paraformaldehyde (PFA) to fix the brain tissue. The excised fixed heads were immersed in PBS/0.2% v/v Gadopentetic acid (Gd-DTPA) contrast agent for 14-20 days, then placed into an imaging vial and submerged in PCF oil (FomblinY®) and scanned for T2-weighted and diffusion tensor imaging (DTI) modalities using the 9.4 T Bruker (Karlsruhe, Germany) BioSpec Avance III 94/20 system. MRI imaging and analysis MRI Imaging and Analysis Imaging was performed on a 9.4 Tesla Bruker BioSpec BioSpec Avance III 94/20 system quadrature volume coils, running Bruker ParaVision 6.0.1 software. The protocol provides stacks of 3D T2-weighted, perfusion and diffusion-weighted images in the axial plane. For T2-weighted images, the TurboRARE method, also called fast spin echo method, was used (TE/TR=36/2500 ms, with field of view=18×18 mm, Resolution 60×60 μm, slice thickness=300 μm, contiguous slices, 21 slices per volume, acquisition time=30 min/Volume (TurboRARE).

For diffusion-weighted imaging, the spin-echo multi-shot echo-planar method was used (TE/TR=22/2,000 ms, Segmented EPI, 4 partitions, field of view=18×18 mm, Resolution 120×120 μm, slice thickness 500 μm, 100 μm slice gap, 9 slices per volume, acquire time=3 h 6 min/map; gradient direction=30 and gradient b-value=1000 $s/mm^2$).

Diffusion images were post-processed in UNSW provided python script and 3D Slicer 4.11 to calculate the fractional anisotropy values. Damaged tissue has a lower FA value compared to non-damaged tissue. As such, the difference between the FA values were compared between the injured (ipsilateral) and uninjured (contralateral) hemispheres of the brain in multiple zones lying immediately besides the primary injury.

Figure 4:
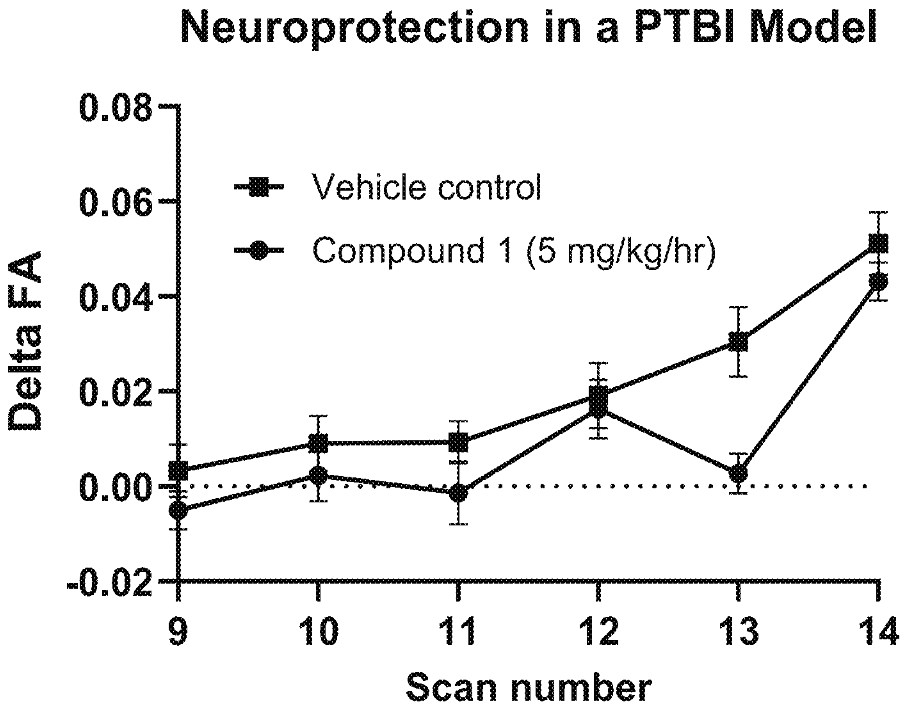
FIG. 4: Assessment of neuroprotection in a PTBI Model. The line graph shows significantly lower mean delta fractional anisotropy (FA) values±standard error of mean (SEM) for six consecutive slices in animals treated with Compound 1 for 48 hours via continuous intravenous infusion at 5 mg/kg/h compared with vehicle control in a penetrating traumatic brain injury (PTBI) model. The mean delta FA was significantly lower in Compound 1 treated animals compared with vehicle-treated animals (p=0.0432, two-way ANOVA, n=13 for vehicle and n=14 for Compound 1).

The average difference between the FA values (dFA) in the injured and uninjured sides in animals from vehicle treated group versus Compound 1 treated (5 mg/kg/h) group are shown in FIG. 4.

Delta FA values (FA value of the uninjured hemisphere minus injured hemisphere) were calculated for ~25 voxels spanning across the horizontal mid-level of six consecutive coronal slice (1 mm apart) in the rostro-caudal plane. A delta FA value of zero denotes that the tissue integrity of the injured hemisphere is similar to that on the uninjured side meaning that the injury is resolved whereas a delta FA value greater than zero denotes injury and loss of issue integrity in the injured hemisphere, with higher delta FA correlating with higher injury. The delta FA values in the six consecutive slices from Compound 1 treated animals was significantly lower than the vehicle-treated animals which confirmed the neuroprotection conferred by Compound 1 treatment (p=0.0432, two-way ANOVA, n=13 for vehicle and n=14 for Compound 1; FIG. 4).

These results show that Compound 1 of the invention is efficacious in a model of severe traumatic brain injury in rats achieved using a penetrating ballistic brain injury (PTBI) model.

Biological Example 7: Activity of Compound 1 in a Model of Acute Myocardial Ischemia (AMI)

Surgical Procedure 1

Compound 1 was assessed for its efficacy to reduce cardiac injury following myocardial ischemia. Male Sprague-Dawley rats aged 6-8 weeks were anesthetized by isoflurane, and the heart was exposed through a thoracotomy performed in the fourth or fifth intercostal space. The suture thread was used to occlude the left anterior descending coronary artery (LAD). The suture thread was released after 30 min. Animals were treated with Compound 1 at 1.25 mg/kg/h (30 mg/kg/day, formulated in 10% DMSO+10% Solutol HS-15+25% PEG300+15% PG, 40% (0.1% Tween80 in 50 mM Carbonate buffer pH 9) or vehicle 5 minutes prior to the end of ischemia (i.e. 5 minutes before reperfusion starts), with continuous intravenous infusion using a catheter implanted 6 days prior to surgery, continuing for 24 h after reperfusion begins.

Echocardiography Measurement

After 24 h of reperfusion, rats were anesthetized by isoflurane. The M-mode image from the parasternal long axis of the LV was carried out using a VINNO system with a probe. Left ventricle (LV) ejection fraction (EF), LV end-diastolic dimensions (LVIDd), LV end-systolic dimensions (LVIDs), LV diastolic posterior wall thickness (LVPWd), LV systolic posterior wall thickness (LVPWs), and fractional shortening (FS) were collected as assessments of cardiac function in Compound 1 versus vehicle treated animals.

Figure 5:
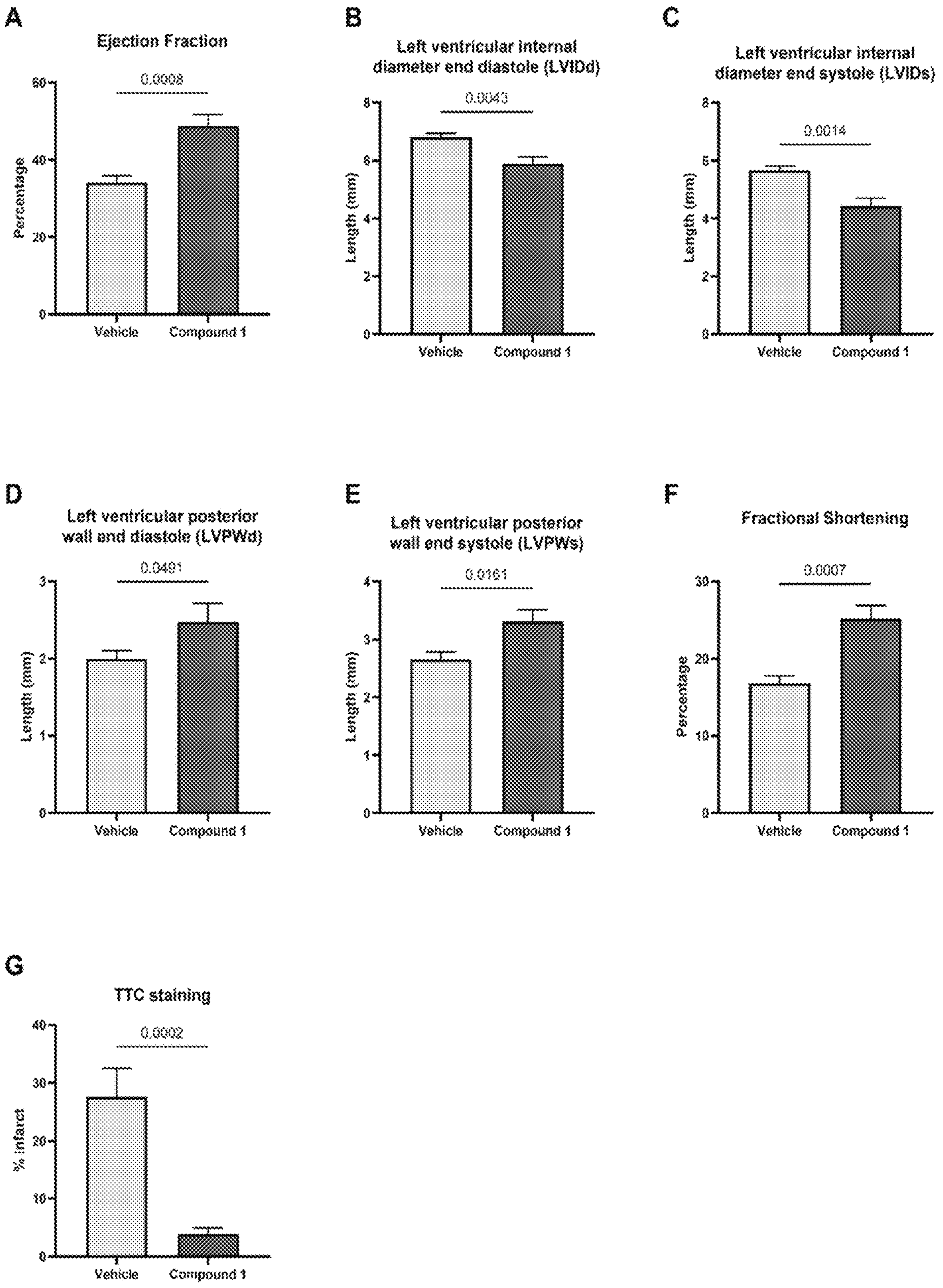
FIG. 5: Assessments of cardiac function in Compound 1 treated animals verses vehicle treated animals following 24 h of Compound 1 (1.25 mg/kg/h) or vehicle exposure. (A) Left ventricle (LV) ejection fraction (EF) (p=0.008)*; (B) LV end-diastolic dimensions (LVIDd) (p=0.0043)*; (C) LV end-systolic dimensions (LVIDs) (p=0.0014)*; (D) LV diastolic posterior wall thickness (LVPWd) (p=0.0491) #; (E) LV systolic posterior wall thickness (LVPWs) (p=0.0161)*; (F) fractional shortening (FS); and (G) injury size (infarct area) in animals with ischemic-reperfusion injury (p=0.0002) #. * unpaired t-test; #Mann-Whitney non-parametric t-test on ranked data, n=8 rats per group. Data represents mean±standard error of mean.

The cardioprotective effects following administration of Compound 1 at 1.25 mg/kg/hour in rats after a myocardial ischemic-reperfusion injury model are presented in FIG. 5. Significant improvements were seen in the functional parameters and tissue loss in hearts from rats treated with Compound 1 compared with vehicle only (A) ejection fraction (p=0.008)*, (B) LVIDd (p=0.0043)*, (C) LVIDs (p=0.0014)*, (D) LVPWd (p=0.0491) #, (E) LVPWs (p=0.0161)*, (F) fractional shortening, (G) infarct area (p=0.0002) #. * unpaired t-test; #Mann-Whitney non-parametric t-test on ranked data, n=8 rats per group.

Blood Sample Collection for Blood Chemistry and ELISA

A 4 and 24 hours post reperfusion initiation, blood samples were collected immediately by orbital vein into 1 mL serum tubes centrifuged at 4° C., 4000 g for 5 minutes. Cardiac troponin I levels were measured in these samples using a commercially available enzyme linked immunosorbent assay. Briefly, the standards and samples were added to the assay plate in duplicate along with the HRP-conjugate and incubated for 60 minutes at room temperature. The plate was washed 5× with wash solution and TMB was added and incubated for 20 minutes at room temperature after which stop solution was added. The absorbance of each well was determined at 450 nm and the protein levels calculated against a standard curve to determine cardiac troponin I levels in Compound 1 versus vehicle treated animals.

Figure 6:
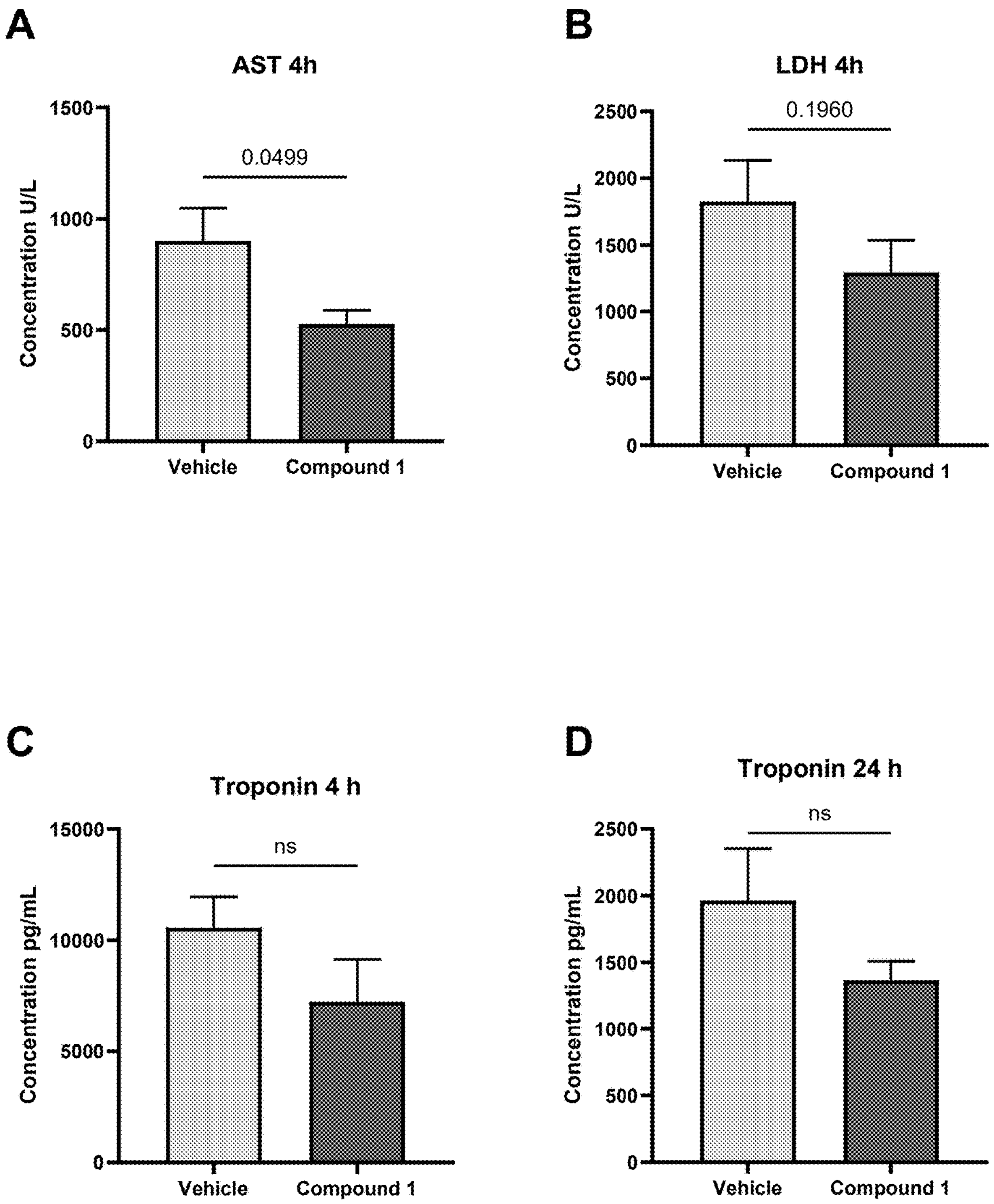
FIG. 6: Assessment of serum biomarkers of injury in Compound 1 treated animals verses vehicle treated animals. (A) Aspartate transferase (AST) (p=0.0499, Mann-Whitney non-parametric t-test on ranked data, n=8 per group); (B) lactic acid dehydrogenase (LDH) (p=0.0285, unpaired t-test, n=8 per group); (C) cardiac troponin I levels at 4 hours or (D) cardiac troponin I levels at 24 hours of Compound 1 (1.25 mg/kg/h) or vehicle exposure. Data represents mean±standard error of mean.

The improvement in serum biomarkers of injury following administration of Compound 1 at 1.25 mg/kg/h in rats after a myocardial ischemic-reperfusion injury model are presented in FIG. 6. There was a significant reduction in the circulating levels of (A) aspartate transferase (AST) (p=0.0499, Mann-Whitney non-parametric t-test on ranked data, n=8), (B) lactic acid dehydrogenase (LDH) (p=0.0285, unpaired t-test, n=8) and a downward trend, although not significant, was seen in troponin I levels at two timepoints (C, D).

2,3,5-Triphenyltetrazolium Chloride (TTC) Staining

TTC staining was used to determine cardiac injury size in animals with ischemic-reperfusion injury following treatment with Compound 1 or vehicle. Briefly, heart tissues were washed with saline 3 times and wiped dry; the hearts were immediately frozen in a refrigerator at −20° C. for 20 min and then cut into 1-2 mm slices. The slices were incubated at 37° C. in 2% solution of TTC (dissolved in phosphate buffer saline, pH 7.4) for 30 min. The infarct size of heart tissue was analyzed by ImageJ software.

A significant reduction in the infarct size was seen in animals that received Compound 1 at 1.25 mg/kg/h (FIG. 5G) confirming that Compound 1 shows efficacy to reduce cardiac injury following myocardial ischemia in rats.

Surgical Procedure 2

The efficacy of Compound 1 was further assessed in a follow-up study in the same AMI model to establish its effect on infarct size and arrhythmia control. Male Sprague Dawley rats (6 to 8-week-old) were subjected to a surgery that involved exposure of the heart through a thoracotomy performed in the fourth intercostal space. A suture thread was used to occlude the left anterior descending (LAD) coronary artery to mimic a myocardial ischemia. The suture thread was released after 1 hour of ischemia, followed by 3 hours of reperfusion. A control ("sham") group that was not subjected to acute myocardial ischemia was incorporated into the study.

Animals were treated with Compound 1 at 3 mg/kg/h (9 mg/kg daily dose, formulated in 10% DMSO+10% Kolliphor® HS-15+25% PEG 300+15% Propylene Glycol (PG)+40% (Tween 80 and 50 mM carbonate buffer, pH 9) or vehicle 35 mins before the initiation of reperfusion (i.e. 25 minutes after the initiation of ischemia by LAD coronary artery occlusion), with continuous IV infusion (via the jugular vein) continuing for 2 h 25 min after the start of reperfusion (i.e. a total IV infusion time of 3 h). Electrocardiography monitoring was performed continuously in each animal. Following the 3 h reperfusion period, animals were euthanised, the heart tissue harvested and then stained with TTC to differentiate between metabolically active (red coloured) versus dead (grey coloured) tissues.

TTC staining delineated the viable tissue from the dead tissue in the injury animals while the sham animals showed even red staining with no signs of injury. A significant reduction of 42% in the mean injury size was observed following 9 mg/kg dosing compared with the vehicle-treated group (p=0.008, one-way ANOVA, Bonferroni t-test post-hoc, n=10, FIG. 7A).

Figure 7:
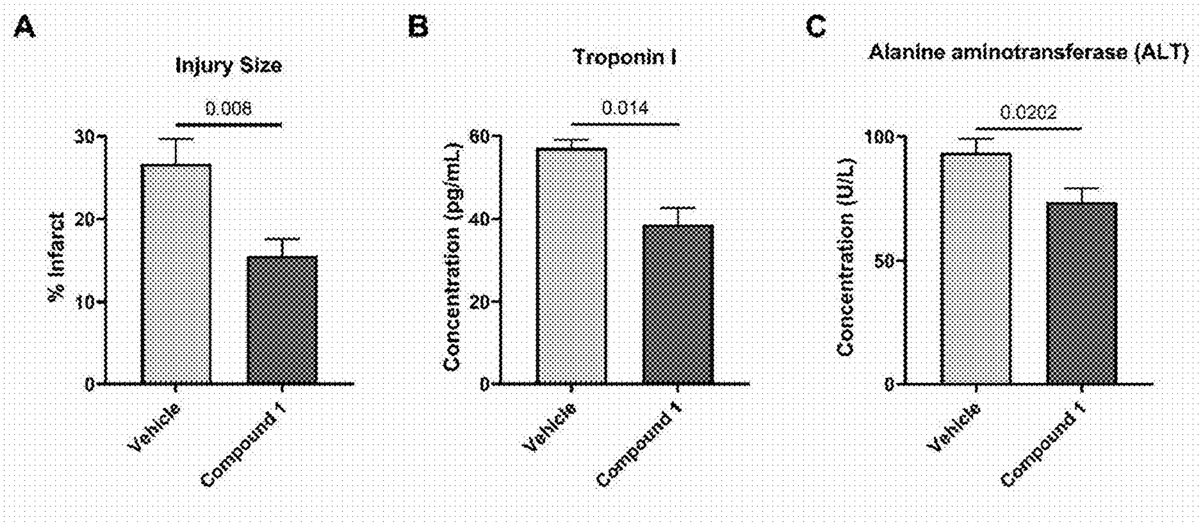
FIG. 7: Bar graphs demonstrating significant reduction in (A) injury size (p=0.008, Bonferroni's t-test, n=10 per group) and injury biomarkers (B) cardiac troponin I (p=0.014, Bonferroni's t-test, n=10 per group) and (C) alanine aminotransferase (ALT) (p=0.01, Bonferroni's t-test, n=9-10 per group) post-treatment treatment with Compound 1 via continuous intravenous infusion at 3 mg/kg/h for 3 hours. Data represents mean±standard error of mean.

Cardiac troponin I (cTnI), a clinically relevant biomarker of cardiac damage, is released into the blood following heart damage. High cTnI levels are correlated with large injury size, worse cardiac function and increased mortality risk. Basal levels of cTnI were detected in the sham animals (16.12±7.80 pg/mL) which increased significantly following injury (p<0.0001, Student's t-test vs I/R+vehicle, n=10 per group) indicative of cardiomyocyte damage following MI injury. There was a significant reduction in cTnI levels at the 9 mg/kg dose compared to vehicle-treated control (32% reduction; p=0.014, one-way ANOVA, Bonferroni t-test post-hoc, n=10; FIG. 7B).

Following ischemia, there is also a characteristic reduction in cardiac output and an ensuing decrease in systemic blood flow to other organs. The biomarker alanine aminotransferase (ALT) elevates due to liver damage resulting from hypoperfusion. Basal levels of ALT were detected in the sham animals (35.86±10.60 U/L) which increased significantly following injury (p<0.0001, Student's t-test vs I/R+vehicle, n=10 per group) confirming a liver injury response following myocardial ischemia. Compound 1 reduced ALT levels in a dose-dependent manner with a significant reduction observed at the 9 mg/kg dose (21% reduction; p=0.0202, Student's t-test, n=10, FIG. 7C).

Figure 8:
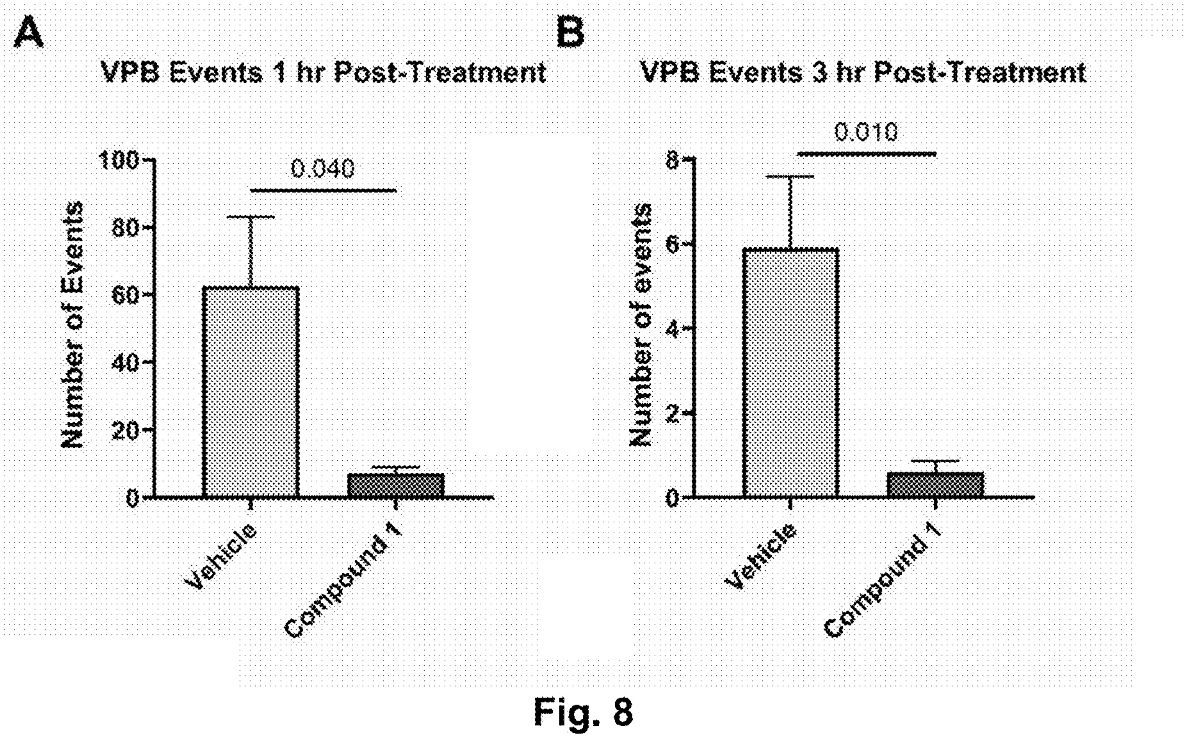
FIG. 8: Bar graph showing significant reduction in ventricular premature beats (VPBs) following (A) 1 hour (p=0.04, Bonferroni's t-test, n=9-10 per group) and (B) 3 hours (p=0.01, Bonferroni's t-test, n=9-10 per group) following treatment with Compound 1 at 3 mg/kg/h. Data represents mean±standard error of mean.

As part of this study, cardiac arrhythmias were monitored via electrocardiogram (ECG). Following myocardial ischemia, ventricular premature beats (VPB) can trigger ventricular tachycardia (VT) and ventricular fibrillation (VF), which are leading causes of sudden cardiac death. A significant reduction in VPB events was noted at the 9 mg/kg dose (88% reduction; p=0.04 at 1 h and 90% reduction; p=0.010 at 3 h versus control, n=9-10, one-way ANOVA, Bonferroni's t-test post-hoc, FIG. 8A-B).

Figure 9:
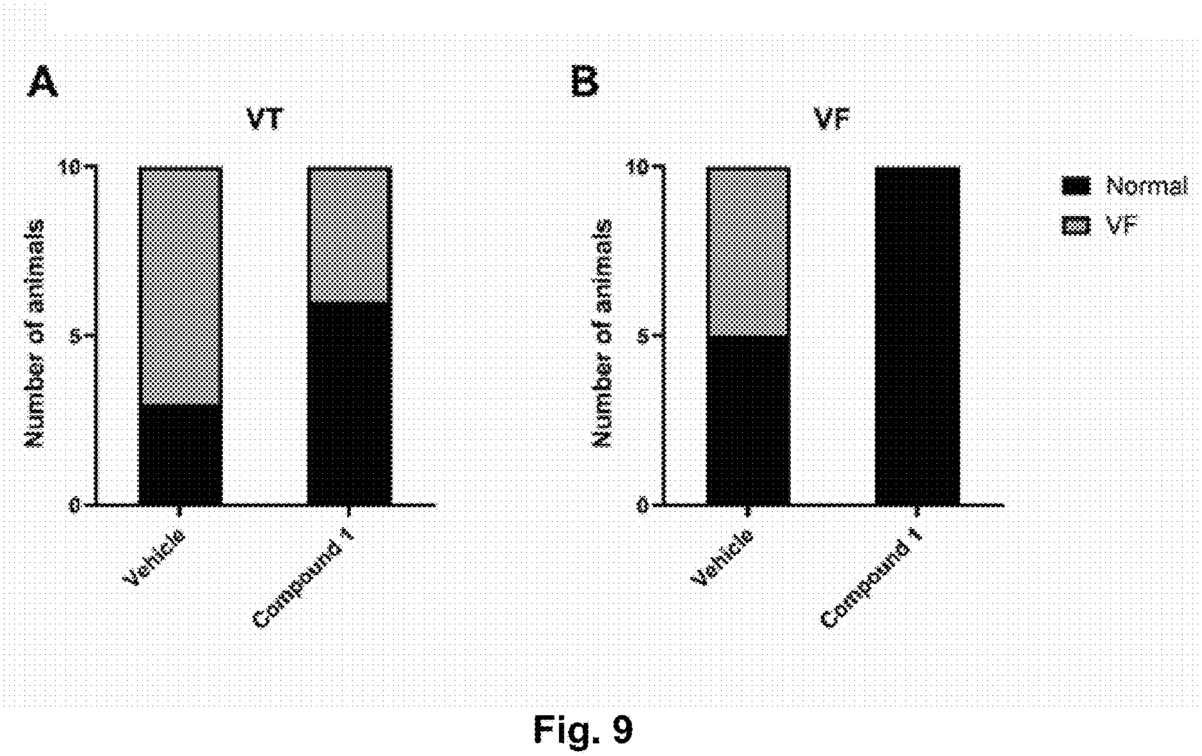
FIG. 9: Graphs showing the number of (A) ventricular tachycardia (VT) and (B) ventricular fibrillation (VF) events following treatment with either vehicle or Compound 1 in a rat myocardial ischemic reperfusion injury model. There was a significant reduction in the number of VF events (p=0.005, chi-square test). Data represents mean±standard error of mean.

In addition, seven incidents of VT were seen in the vehicle treated animals compared to only four observed in animals that received Compound 1 (9 mg/kg). Notably, VF events were completely suppressed in the Compound 1 treated group compared to the vehicle group where five events were observed (p=0.005, chi-square test, n=10; FIG. 9A-B).

Biological Example 8: Activity of Compound 1 in a Rat Model of Pilocarpine-Induced Seizure Compound 1 will be assessed for its efficacy to reduce seizure development in rats following administration of pilocarpine. Male Sprague-Dawley rats will undergo electrode implant surgery in the brain to enable electro encephalogram (EEG) recordings. A positive electrode will be placed over the right frontal cortex (R 2.5 mm, A 3.0 mm) and a negative electrode will be placed over the left hippocampus (L 3.0 mm, P 4.0 mm) with the ground electrode placed over the sinus. Seven days following this surgery, these rats will be implanted with an indwelling catheter in the jugular vein for continuous intravenous infusion of either Compound 1 or vehicle and allowed to recover for two days.

One day prior to seizure induction, the animals will be administered with LiCl (127 mg/kg in sterile water; 5 mL/kg intraperitoneal injection). The following day, EEG will be recorded for 2 hours for baseline measurements, followed by administration of scopolamine (50 mg/kg in PBS; 1 mL/kg intraperitoneal injection). Thirty minutes later, the animals will be administered with pilocarpine (hydrochloride salt, 50 mg/kg in PBS; 5 ml/kg intraperitoneal injection) to induce seizures. Motor behaviour and EEGs will be recorded continuously to establish the onset of status epilepticus following which the animal will be administered with Compound 1 or vehicle and EEG measurements will continue for 300 minutes following the onset of status epilepticus. Animals that do not show any evidence of seizure by EEG or video observation by 40 min after pilocarpine administration will be euthanized at the end of the study and the data will not be analysed.

EEG signals will be fed via a cable to a commutator and then to an amplifier (A-M Systems model 1700) and band pass filtered (0.1-500 Hz for EEG signal). Notch filter of Amplifier should be turned off during data acquisition. The EEG signal is digitized at 512 Hz, and saved in "smr" format with Spike 2. The EEG and EMG signal will also be exported to MATLAB format. Changes of power density after compound administration is normalized to the average of the 1-hour baseline of each rat in each behavioural category. Electrographic seizure is defined as a repetitive epileptiform spiking activity with frequency higher than 5 Hz and amplitude larger than 2 times of baseline. Instantaneous spike probability is determined by calculating the running average of the total number of 3-second bins that contains a spike event in a train of 100 adjacent bins. Cumulative spike probability is determined for each animal by calculating the average of the instantaneous spike probability immediately after compound injection is given.

It is expected that Compound 1 will show efficacy and reduce latency to status epilepticus onset and total spike probability following pilocarpine-induced seizure.

Biological Example 9: Pharmacokinetic (PK) Profile of Compound 1 Following Oral and Subcutaneous Administration The mean plasma concentrations of Compound 1 were assessed following single oral (PO) and single subcutaneous (SC) dose in male C57BL6 mice aged 6-8 weeks (body weight, 20-21 g). Mice were dosed with Compound 1 formulated in 5% DMAC, 5% Solutol HS, 90% saline, either orally (30 mg/kg) or subcutaneously (60 mg/kg) and blood samples were collected at 5 and 15 mins, and at 1, 2, 4, 6 hours via the facial vein.

The plasma samples were mixed with internal standard (diclofenac, 50 ng/ml) in acetonitrile. The mixture was centrifuged (5,800 rpm) and analyzed using LC-MS/MS.

The half-life of Compound 1 following single oral dose was 51 minutes, whereas it was 98.4 minutes following single subcutaneous dose.

TABLE 7

Mean concentration ± standard deviation of Compound 1 following single oral (PO) or subcutaneous (SC) dosing.

| | Concentration (ng/mL) | |
|---|---|---|
| Time (hour) | PO (30 mg/kg) | SC (60 mg/kg) |
| 0.083 | 1,622 ± 1,254 | 4,707 ± 1,072 |
| 0.25 | 2,166 ± 1,172 | 4,560 ± 570 |
| 1.0 | 312 ± 79.3 | 1,750 ± 165 |
| 2.0 | 42.3 ± 2.57 | 610 ± 96.2 |
| 4.0 | 4.98 ± 1.53 | 240 ± 94.9 |
| 6.0 | 2.10 ± 0.69 | 209 ± 81.5 |

The invention claimed is:

1. A compound of Formula I, or a pharmaceutically acceptable salt, solvate or stereoisomer thereof:

Formula I

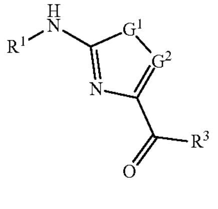

wherein:

$G^1$ is O or S;

$G^2$ is $CR^2$ or N;

$R^1$ is

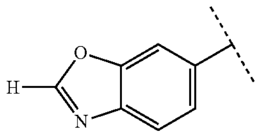

or

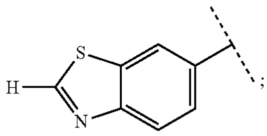

;

$R^2$ is selected from H, D, halo, hydroxy, amino, cyano, and $C_1$-$C_4$alkyl;

$R^3$ is:

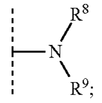

and $R^8$ and $R^9$ together with the N atom between them form an optionally substituted ring; wherein the ring formed by $R^8$ and $R^9$ and the N atom between them comprises 3-9 ring atoms.

2. The compound, or a pharmaceutically acceptable salt, solvate or stereoisomer thereof of claim 1 wherein the ring formed by $R^8$ and $R^9$ together with the N atom between them is selected from

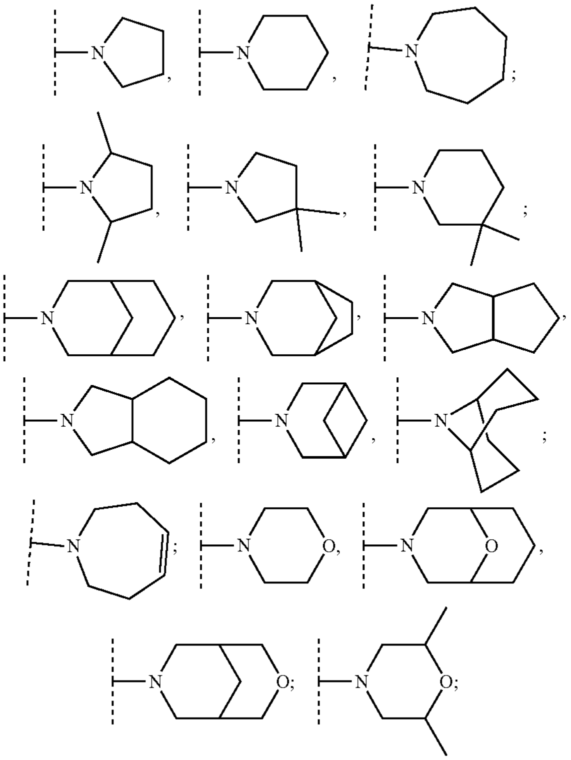

-continued

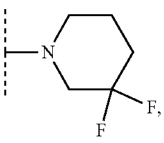

and

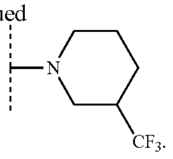

3. The compound or a pharmaceutically acceptable salt, solvate or stereoisomer thereof of claim 1 wherein $R^3$ is 1-piperidine; optionally substituted with 1-4 substituents wherein the substituents are independently selected from D, halo, $C_1$-$C_6$alkyl, $C_1$-$C_6$alkoxy, $C_1$-$C_6$fluoroalkyl, phenyl, cyano, $C_1$-$C_6$thioalkyl, and $C_1$-$C_6$alkylamino.

4. The compound or a pharmaceutically acceptable salt, solvate or stereoisomer thereof of claim 1 wherein $R^3$ is 3,5-dimethylpiperidine or 2,3-dimethylpiperidine.

5. A compound or a pharmaceutically acceptable salt, solvate or stereoisomer thereof of Formula II:

Formula II

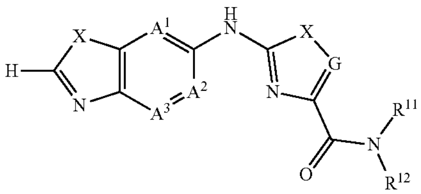

wherein $A^1$, $A^2$ and $A^3$ are selected from N, CH and CF;

X is selected from O and S;

G is selected from N and $CR^{10}$;

$R^{10}$ is H, D, halo, $C_1$-$C_4$alkyl, hydroxy, amino, $C_1$-$C_4$alkyl, $C_1$-$C_4$alkoxy, $C_1$-$C_4$fluoroalkyl, phenyl, cyano, $C_1$-$C_4$thioalkyl, or $C_1$-$C_4$alkylamino;

where $R^{11}$ and $R^{12}$ together with the N atom between them form a ring comprising 3-9 ring atoms.

6. The compound or a pharmaceutically acceptable salt, solvate or stereoisomer thereof of claim 5 wherein the ring formed by $R^{11}$ and $R^{12}$ together with the N atom between them form a mono- or bi-cyclic, saturated or unsaturated, or halo- or hetero-substituted alkyl ring.

7. A compound or a pharmaceutically acceptable salt, solvate or stereoisomer thereof selected from the group consisting of:

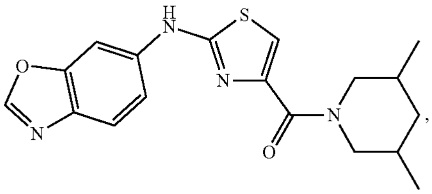

,

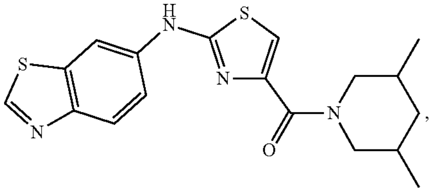

,

-continued
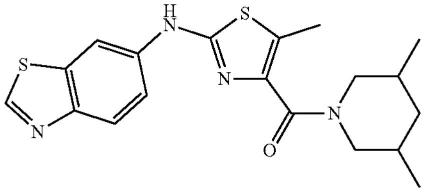,
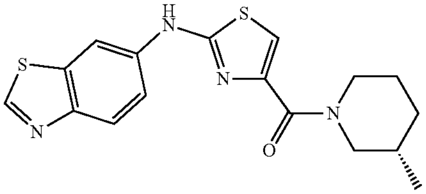,
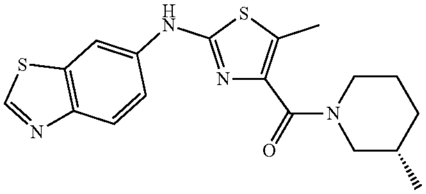,
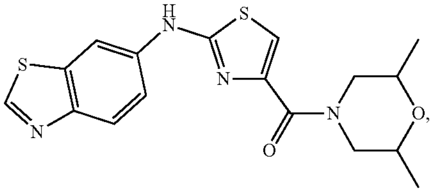,
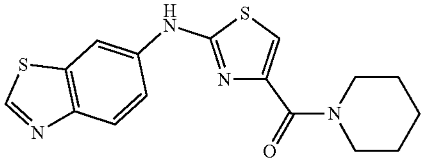,
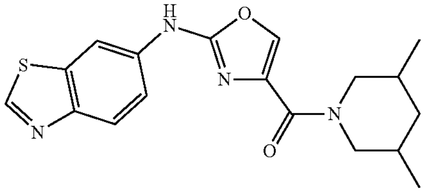,
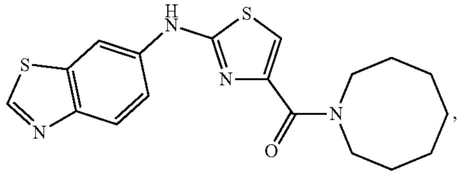,
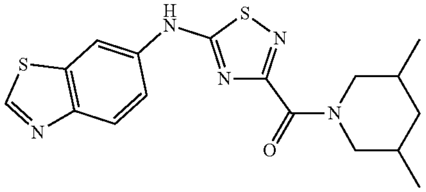,
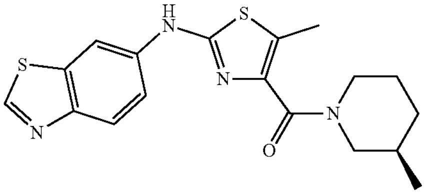,
-continued
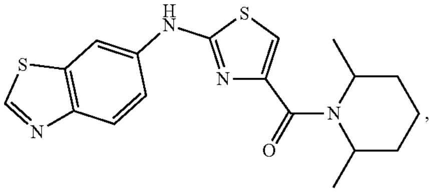,
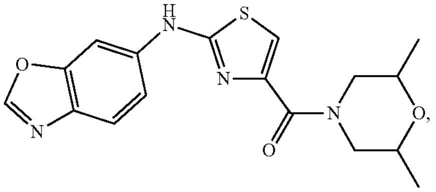,
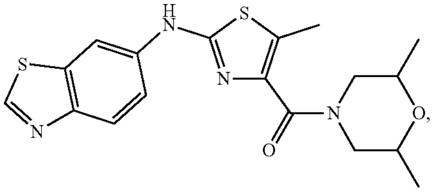,
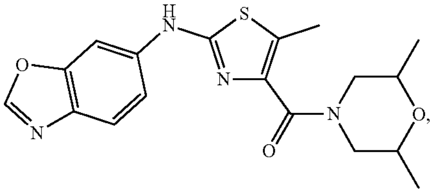,
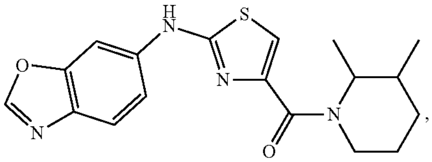,
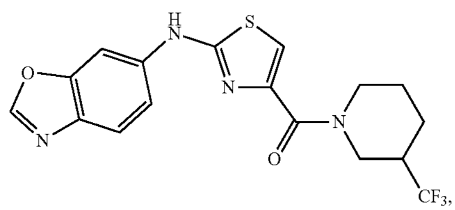,
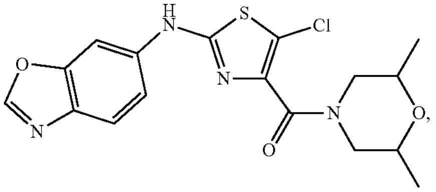,
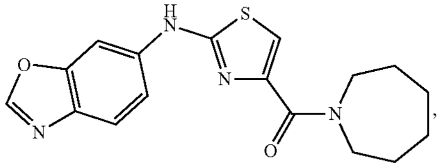,
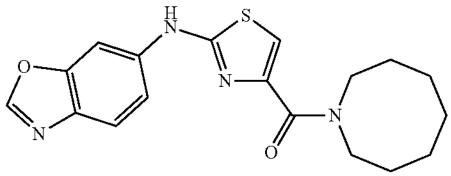, -continued
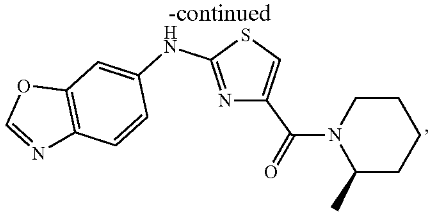
,
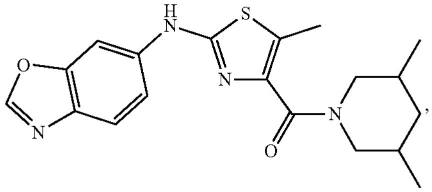
,
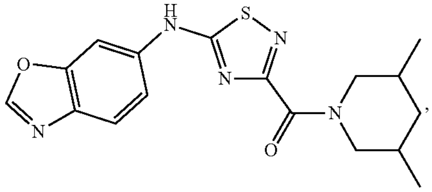
,
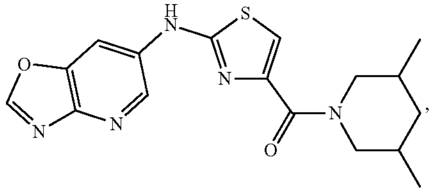
, and
-continued
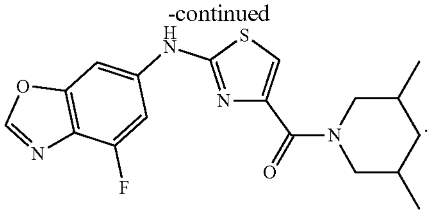
.
8. The compound or a pharmaceutically acceptable salt, solvate or stereoisomer thereof of claim 1 having the structure
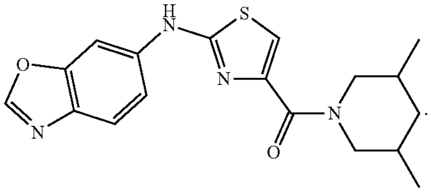 [SMILES: CC1CC(C)CN(C(=O)c2csc(Nc3ccc4ncoc4c3)n2)C1]
.
9. A pharmaceutical composition comprising a compound of Formula I as defined in claim 1, or a pharmaceutically acceptable salt, solvate or stereoisomer thereof, and a pharmaceutically acceptable excipient.
* * * * *